(12) United States Patent
Ameriks et al.

(10) Patent No.: US 7,132,440 B2
(45) Date of Patent: Nov. 7, 2006

(54) SUBSTITUTED BENZIMIDAZOLES AND IMIDAZO-[4,5]-PYRIDINES

(75) Inventors: Michael K. Ameriks, San Diego, CA (US); Kristen L. Arienti, La Mesa, CA (US); Frank U. Axe, Escondido, CA (US); J. Guy Breitenbucher, Escondido, CA (US)

(73) Assignee: Janssen Pharmaceutica, N.V. (BE)

( * ) Notice: Subject to any disclaimer, the term of this patent is extended or adjusted under 35 U.S.C. 154(b) by 13 days.

(21) Appl. No.: 10/825,823

(22) Filed: Apr. 16, 2004

(65) Prior Publication Data

US 2004/0214857 A1 Oct. 28, 2004

Related U.S. Application Data

(60) Provisional application No. 60/463,542, filed on Apr. 17, 2003.

(51) Int. Cl.
*A61K 31/4184* (2006.01)
*C07D 235/18* (2006.01)

(52) U.S. Cl. .................. 514/394; 548/305.1; 548/310.7
(58) Field of Classification Search ............. 548/310.7; 514/394
See application file for complete search history.

(56) References Cited

U.S. PATENT DOCUMENTS

| | | | |
|---|---|---|---|
| 5,059,621 A | | 10/1991 | Shroot et al. |
| 6,310,082 B1 * | | 10/2001 | Griffin et al. ............... 514/394 |
| 2003/0100582 A1 | | 5/2003 | Sircar et al. |
| 2003/0176438 A1 * | | 9/2003 | Arienti et al. ......... 514/252.04 |

FOREIGN PATENT DOCUMENTS

| EP | 0148431 A1 | 7/1985 |
|---|---|---|
| EP | 0209707 A2 | 1/1987 |
| EP | 0719765 A2 | 7/1996 |
| WO | WO 9806703 A1 | 2/1998 |
| WO | WO 9911627 A1 | 3/1999 |
| WO | WO 9930710 A1 | 6/1999 |
| WO | WO 9961019 A1 | 12/1999 |
| WO | WO 9961020 A1 | 12/1999 |
| WO | WO 0100587 A1 | 1/2001 |
| WO | WO 0121771 A2 | 3/2001 |
| WO | WO 0153268 A2 | 7/2001 |
| WO | WO 0174786 A1 | 10/2001 |
| WO | WO 02/072090 | 9/2002 |
| WO | WO 03011219 A2 | 2/2003 |
| WO | WO 03/028724 | 4/2003 |
| WO | WO 03/032984 | 4/2003 |
| WO | WO 0393297 A2 | 11/2003 |
| WO | WO 0411439 A2 | 2/2004 |
| WO | WO 0441209 A2 | 5/2004 |

OTHER PUBLICATIONS

Kim, J. S., et al. Structure-Activity Relationships of Benzimidazoles and Related Heterocycles as Topoisomerase I Poisons, 1996, Bioorg. Med. Chem. 4(4), pp. 621-630.*
White, A.W., et al., "Resistance-modifying agents. 9. Synthesis and biologicalproperties of benzimidazole inhibitors of the DNA repair enzyme poly(ADP-ribose) polymerase", Journal of Medicinal Chemistry, American Chemical Society, Washington, US, vol. 43, No. 2, Nov. 2, 2000, pp. 4084-4097.
PCT International Search Report, dated Aug. 26, 2004, for PCT Int'l Appln. No. PCT/US2004/011775.
Blasina, A. et al. A Human Homologue of the Checkpoint Kinase Cds1 Directly Inhibits Cdc25 Phosphatase. Curr. Biol. (1999) 9(1):1-10.
Buscemi, G. et al. Chk2 Activation Dependence on Nbs1 after DNA Damage. Mol. Cell. Biol. (2001) 21(15):5214-5222.
Falck, J. et al. The ATM-Chk2-Cdc25A Checkpoint Pathway Guards against Radioresistant DNA Synthesis. Nature (London) (2001) 410:842-847.
Hirao, A. et al. Chk2 Is a Tumor Suppressor That Regulates Apoptosis in both an Ataxia Telangiectasia Mutated (ATM)-Dependent and an ATM-Independent Manner. Mol. Cell. Biol. (2002) 22(18):6521-6532.
Kim, J.S. et al. Structure-Activity Relationships of Benzimidazoles and Related Heterocycles as Topoisomerase I Poisons. Bioorg. Med. Chem. (1996) 4(4):621-630.
Lee, J.-S. et al. hCds1-Mediated Phosphorylation of BRCA1 Regulates the DNA Damage Response. Nature (London) (2000) 404:201-204.
Matsuoka, S. et al. Linkage of ATM to Cell Cycle Regulation by the Chk2 Protein Kinase. Science (Washington, D.C.) (1998) 282:1893-1897.
Takai, H. et al. Chk2-Deficient Mice Exhibit Radioresistance and Defective p53-Mediated Transcription. EMBO J. (2002) 21(19):5195-5205.
Tawar, U. et al. Influence of Phenyl Ring Distribution on Bisbenzimidazole and Terbenzimidazole Cytotoxicity: Synthesis and Biological Evaluation as Radioprotectors. J. Med. Chem. (2003) 48(18): 3785-3792.
Tominaga, K. et al. Role of Human Cds1 (Chk2) Kinase in DNA Damage Checkpoint and Its Regulation by p53. J. Biol. Chem. (1999) 274(44):31463-31467.
Arienti, K.L. et al. Checkpoint Kinase Inhibitors: SAR and Radiprotective Properties of a Series of 2-Arylbenzimidazoles. J. Med. Chem. 2005, 48, 1873-1885.

* cited by examiner

*Primary Examiner*—Kamal A. Saeed
*Assistant Examiner*—Nyeemah Grazier

(57) ABSTRACT

2-Aryl substituted benzimidazoles and imidazo[4,5]pyridines are disclosed as inhibitors of Cds1 and useful as adjuvants to chemotherapy or radiation therapy in the treatment of cancer.

17 Claims, No Drawings

SUBSTITUTED BENZIMIDAZOLES AND IMIDAZO-[4,5]-PYRIDINES

This application claims priority to and benefit of U.S. Provisional Application Ser. No. 60/463,542, filed on Apr. 17, 2003.

FIELD OF THE INVENTION

The present invention relates to substituted benzimidazole and imidazo-[4,5]-pyridine compounds, compositions containing them, and methods of using them.

BACKGROUND OF THE INVENTION

The maintenance of an intact genome is of crucial importance to every organism. The individual cell in a multicellular eukaryotic organism possesses sophisticated and intricate mechanisms to properly respond to DNA damage. Such mechanisms repair damaged DNA or trigger programmed cell death (apoptosis). In response to DNA damage, checkpoint kinases are thought to be intimately involved in these processes. These kinases are activated by, upstream proteins, such as ATM (ataxia-telangiectasia mutated) and ATR (ataxia-telangiectasia mutated and rad3-related), and in turn trigger cell cycle arrest by inhibition of proteins such as Cdc25A or Cdc25C. The checkpoint kinases may also modulate the activity of other proteins that are thought to be involved in DNA repair and programmed cell death. Examples of such proteins are BRCA1 and p53.

The checkpoint kinase Cds1 (in man also known as Chk2) is conserved from yeast to man. A human homolog of the *Schizosaccharomyces pombe* Cds1 gene has been described (Tominaga, K. et al. *J. Biol. Chem.* 1999, 274(44):31463–31467; Matsouka, S. et al. *Science* 1998, 282:1893–1897; Blasina, A. et al. *Curr. Biol.* 1999, 9(1): 1–10). Human Cds1 was rapidly activated by phosphorylation in response to DNA damage in both normal cells and in p53-deficient cancer cells. High levels of hCds1 were observed in p53-deficient cells. In human cells Cds1 has been implicated in the regulation by phosphorylation of proteins such as p53, BRCA1, Cdc25A, and Cdc25C (See: Lee, J.-S. et al. *Nature* 2000, 404:201–204; Falck, J. et al. *Nature* 2001, 410:842–847; and Buscemi, G. et al. *Mol. Cell. Biol.* 2001, 21(15):5214–5221). As described below, inhibition of Cds1 offers two strategies for improving the effectiveness of DNA-damaging cancer treatments.

Cancer cells are often deficient in the mechanisms responsible for maintaining an intact genome. In particular, they have often lost proper p53 function, which generally correlates with the progression of a tumor to a more aggressive state, such as the progression from a preinvasive to invasive stage of colon cancer, or from a low grade to a high grade astrocytoma. Between 30% and 70% of all subtypes of tumors have a point mutation in one of the two p53 gene copies and have lost the other allele. P53-deficient cells are generally more resistant to radiation. It is thought that the lack of initiation of programmed cell death in cancer cells may render such cells less sensitive to DNA-damaging cancer treatments. The transcription factor p53 is of importance not only for the initiation of programmed cell death, but also in cell cycle arrest. Loss of p53 function may therefore leave cancer cells with limited protection against insult to the genome. Further disruption of DNA damage repair and cell cycle arrest by inhibition of kinases such as Cds1 could then render cancer cells unable to survive after DNA damage. Therefore inhibition of Cds1 could, by removing the remaining components of DNA damage repair, render the cancer cells more susceptible to treatments such as chemical DNA-damaging agents or ionizing radiation.

Normal cells, on the other hand, have an intact p53 system, and will often undergo apoptosis in response to DNA-damaging treatments at a much lower dose than that required to kill cancer cells. Therefore, in such situations, normal cells will be at a disadvantage compared to cancer cells, and cancer treatments often have to be discontinued due to serious side effects caused by loss of normal cells before the cancer has been eradicated. Inhibition of Cds1, which would prevent this kinase from phosphorylating and thereby stabilizing p53, could therefore protect normal cells from the effects of ionizing radiation or DNA-damaging chemotherapeutics while still allowing these agents to be effective against p53-deficient cancer cells. This would have the effect of increasing the therapeutic potential of these agents. This view is supported by studies of mice deficient in Cds1 (See: Hirao, A. et al. *Mol. Cell. Biol.* 2002, 22(18): 6521–6532; Takai, H. et al. *EMBO J.* 2002, 21(19):5195–5205; WO 01/98465 A1 Chugai Seiyaku Kabushiki Kaisha, Dec. 27, 2001). These animals showed increased resistance to the apoptosis caused by ionizing radiation over their wild-type counterparts. For example, it was shown that these animals were protected from apoptosis of intestinal cells, hair follicle cells, cells of the CNS, and thymus cells relative to their wild-type counterparts when treated with ionizing radiation. Cds1 knockout animals also showed increased survival when exposed to ionizing radiation. It is therefore logical to assume that chemical inhibitors of Cds1 would have therapeutic potential in the protection of patients from the deleterious side effects of radiation or DNA-damaging chemotherapeutics.

Additional examples of cell cycle checkpoint modulators in development include UCN-01 (CAS 112953–11–4), UCN-02, KW-2401, NSC-638850 (Kyowa Hakko/National Cancer Institute) and SB-218078 (CAS 135897–06–2) (SmithKline Beecham).

Additional relevant publications include DE 0148431 (T 7570), WO 01/21771 A2, WO 02/072090 A1, WO 03/011219 A2, and White, A. W. et al. *J. Med. Chem.* 2000, 43(22):4084–4097.

It is an object of the present invention to provide a Cds1-inhibiting adjuvant for use with ionizing radiation in the treatment of cancers.

It is another object of the present invention to provide a Cds1-inhibiting adjuvant for use with DNA-damaging chemotherapeutics in the treatment of cancers.

It is still another object of the present invention to provide a Cds1-inhibiting adjuvant for use with ionizing radiation and/or DNA-damaging chemotherapeutics that promotes the death of cancer cells damaged by such radiation or chemotherapeutics.

It is yet another object of the present invention to provide a Cds1-inhibiting adjuvant for use with ionizing radiation and/or DNA-damaging chemotherapeutics that prevents apoptosis of healthy cells damaged by such radiation or chemotherapeutics.

It is also an object of the present invention to provide a Cds1-inhibiting adjuvant for use with ionizing radiation and/or DNA-damaging chemotherapeutics that both promotes in a patient the death of cancer cells and prevents the apoptosis of healthy cells damaged by such radiation or chemotherapeutics.

It is also another object of the present invention to provide a Cds1-inhibiting adjuvant for use with ionizing radiation and/or DNA-damaging chemotherapeutics in the treatment of p53-deficient cancer cells.

It is an additional object of the present invention to provide a Cds1-inhibiting adjuvant for use with ionizing radiation and/or DNA-damaging chemotherapeutics that both promotes in a patient the death of p53-deficient cancer cells and prevents the apoptosis of healthy cells damaged by such radiation or chemotherapeutics.

It is an object of the present invention to provide a method for the treatment of cancer in a patient comprising exposing the cancer to ionizing radiation and administering a Cds1-inhibiting adjuvant.

It is another object of the present invention to provide a method for the treatment of cancer in a patient comprising administering a DNA-damaging chemotherapeutic and a Cds1-inhibiting adjuvant.

It is still another object of the present invention to provide a method to promote in a patient the death of cancer cells damaged by exposure to ionizing radiation and/or by administration of a DNA-damaging chemotherapeutic comprising the step of administering a Cds1-inhibiting adjuvant in conjunction with such therapies.

It is yet another object of the present invention to provide a method to prevent in a patient the apoptosis of healthy cells damaged by exposure to ionizing radiation and/or by administration of a DNA-damaging chemotherapeutic comprising the step of administering a Cds1-inhibiting adjuvant in conjunction with such therapies.

It is also an object of the present invention to provide a method to both promote in a patient the death of cancer cells and prevent the apoptosis of healthy cells damaged by exposure to ionizing radiation and/or by administration of a DNA-damaging chemotherapeutic comprising the step of administering a Cds1-inhibiting adjuvant in conjunction with such therapies.

It is also another object of the present invention to provide a method for the treatment of p53-deficient cancer cells in a patient comprising exposing the cancer cells to ionizing radiation and/or administering a DNA-damaging chemotherapeutic and administering a Cds1-inhibiting adjuvant.

It is an additional object of the present invention to provide a method to both promote in a patient the death of p53-deficient cancer cells and to prevent the apoptosis of healthy cells damaged by exposure to ionizing radiation and/or by administration of a DNA-damaging chemotherapeutic comprising the step of administering a Cds1-inhibiting adjuvant in conjunction with such therapies.

SUMMARY OF THE INVENTION

The present invention features compounds of formula (I):

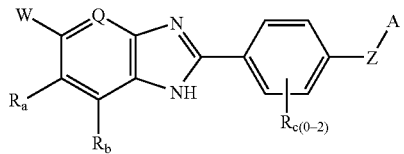

wherein
W is —COOH, —(CO)NH$_2$, or —(SO$_2$)NH$_2$;
Q is N or CH;
R$_a$ and R$_b$ are independently selected from —H and halogen;
R$_c$ is absent or is independently selected from the group consisting of —OH, —CF$_3$, —C$_{1-4}$alkyl, —OC$_{1-4}$alkyl, —NO$_2$ and halo;
Z is selected from the group consisting of
 a) >C=O, >C=CHR$_f$, >CR$_d$R$_d$, >CF$_2$, >CR$_d$OR$_e$, >C(OR$_d$)OR$_e$,
 b) >C(R$_d$)NR$_d$R$_g$,
 c) —SO$_2$NR$_d$C(R$_h$)$_2$—,

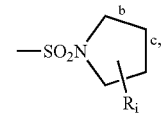

where A is fused at the b or c faces, at a face of A which contains two carbon atoms, which is saturated or unsaturated,

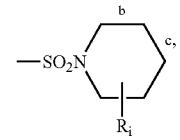

where A is fused at the b or c faces, at a face of A which contains two carbon atoms, which is saturated or unsaturated,
 d) >NC$_{1-4}$alkyl, where the alkyl is optionally substituted with a substituent selected from the group consisting of —NH$_2$, —NHC$_{1-4}$alkyl, —N(C$_{1-4}$alkyl)$_2$, —CONH$_2$, —CONHC$_{1-4}$alkyl, —CON(C$_{1-4}$alkyl)$_2$, —COOH, —COOC$_{1-4}$alkyl, —OH and —OC$_{1-4}$alkyl;
R$_d$ is independently selected from the group consisting of —H and —C$_{1-4}$alkyl;
R$_e$ is independently selected from the group consisting of —H and optionally mono- or di-substituted —C$_{1-4}$alkyl, where the substituent is independently selected from the group consisting of —NH$_2$, —NHC$_{1-4}$alkyl, —N(C$_{1-4}$alkyl)$_2$, —CONH$_2$, —CONHC$_{1-4}$alkyl, —CON(C$_{1-4}$alkyl)$_2$, —COOH, —COOC$_{1-4}$alkyl, —CN, —OH and —OC$_{1-4}$alkyl;
alternatively, R$_d$ and R$_e$ may be taken together with their atoms of attachment to form a 5 to 8 membered heterocyclic ring, with the heterocyclic ring having 0 or 1 unsaturated bonds, having 0, 1 or 2 carbon members which is a carbonyl, having 0 or 1 additional heteroatom members separated from an atom of attachment by at least one carbon member and selected from O, S, —N=, >NH or >NC$_{1-4}$alkyl and having a maximum of two heteroatom ring members;
R$_f$ is independently selected from the group consisting of —H, —CONH$_2$, —CONHC$_{1-4}$alkyl, —CON(C$_{1-4}$alkyl)$_2$, —COOH, —COOC$_{1-4}$alkyl and optionally mono- or di-substituted C$_{1-4}$alkyl, where the substituent is independently selected from the group consisting of —NH$_2$, —NHC$_{1-4}$alkyl, —N(C$_{1-4}$alkyl)$_2$, —CONH$_2$, —CONHC$_{1-4}$alkyl, —CON(C$_{1-4}$alkyl)$_2$, —COOH, —COOC$_{1-4}$alkyl, —CN, —OH and —OC$_{1-4}$alkyl;
R$_g$ is independently selected from the group consisting of —H and optionally mono- or di-substituted —C$_{1-4}$alkyl, where the substituent is independently selected from the group consisting of —NH$_2$, —NHC$_{1-4}$alkyl, —N(C$_{1-4}$ alkyl)$_2$, —CONH$_2$, —CONHC$_{1-4}$alkyl, —CON(C$_{1-4}$ alkyl)$_2$, —COOH, —COOC$_{1-4}$alkyl, —CN, —OH and —OC$_{1-4}$alkyl;

alternatively, R$_d$ and R$_g$ may be taken together with their nitrogen of common attachment to form a 5 to 8 membered heterocyclic ring, with the heterocyclic ring having 0 or 1 unsaturated bonds, having 0, 1 or 2 carbon members which is a carbonyl and having 0 or 1 additional heteroatom members separated from the atom of common attachment by at least one carbon member and selected from O, S, —N=, >NH or >NC$_{1-4}$alkyl;

R$_h$ is independently selected from the group consisting of —H, and optionally mono- or di-substituted C$_{1-4}$alkyl, where the substituent is independently selected from the group consisting of —NH$_2$, —NHC$_{1-4}$alkyl, —N(C$_{1-4}$ alkyl)$_2$, —CN, —OH and —OC$_{1-4}$alkyl; or, alternatively, R$_h$ is —CH$_2$CH$_2$— or —CH$_2$CH$_2$CH$_2$—, optionally substituted with R$_i$, which is bonded to a carbon of A adjacent to the carbon of Z attachment, forming a five- or six-membered carbocyclic ring;

R$_i$ is independently selected from the group consisting of —H, —OH, —OC$_{1-4}$alkyl and optionally mono- or di-substituted C$_{1-4}$alkyl, where the substituent is independently selected from the group consisting of —NH$_2$, —NHC$_{1-4}$alkyl, —N(C$_{1-4}$alkyl)$_2$, —CONH$_2$, —CONHC$_{1-4}$alkyl, —CON(C$_{1-4}$alkyl)$_2$, —COOH, —COOC$_{1-4}$alkyl, —CN, —OH and —OC$_{1-4}$alkyl;

A is selected from the group consisting of:
a) phenyl, optionally mono-, di- or tri-substituted with R$_p$;
R$_p$ is selected from the group consisting of —OH, —C$_{1-6}$alkyl, —OC$_{1-6}$alkyl, —C$_{3-6}$cycloalkyl, —OC$_{3-6}$cycloalkyl, —CN, —NO$_2$, —N(R$_y$)R$_z$ (wherein R$_y$ and R$_z$ are independently selected from —H or —C$_{1-6}$alkyl, or may be taken together with the nitrogen of attachment to form an otherwise aliphatic hydrocarbon ring, said ring having 5 to 7 members, optionally having one carbon replaced with >O, =N—, >NH or >N(C$_{1-4}$alkyl) and optionally having one or two unsaturated bonds in the ring), —(C=O)N(R$_y$)R$_z$, —(N—R$_t$)COR$_t$ (wherein R$_t$ is independently —H or —C$_{1-6}$alkyl), —(N—R$_t$)SO$_2$C$_{1-6}$alkyl, —(C=O)C$_{1-6}$alkyl, —(S=(O)$_n$)—C$_{1-6}$alkyl (wherein n is selected from 0, 1 or 2), —SO$_2$N(R$_y$)R$_z$, —SCF$_3$, halo, —CF$_3$, —OCF$_3$, —COOH, —C$_{1-6}$alkylCOOH, —COOC$_{1-6}$alkyl and —C$_{1-6}$alkylCOOC$_{1-6}$alkyl;
b) phenyl, attached at two adjacent ring members to a C$_{3-5}$alkyl moiety to form a fused 5 to 7 membered ring, said fused ring optionally having a second unsaturated bond, said fused ring optionally having one or two members replaced with =N—, >O, >NH or >N(C$_{1-4}$ alkyl) except that no such replacement is permitted where the fused ring is 5 membered and has a second unsaturated bond, and said fused ring optionally having one carbon member replaced with >C=O, the fused rings optionally mono-, di- or tri-substituted with R$_p$;
c) a monocyclic aromatic hydrocarbon group having six ring carbon atoms, having a carbon atom which is the point of attachment, having one or two carbon atoms replaced by N, and optionally mono- or di-substituted with R$_p$;
d) a monocyclic aromatic hydrocarbon group having six ring carbon atoms, having a carbon atom which is the point of attachment, having zero, one or two carbon atoms replaced by N, and having attachment at two adjacent carbon ring members to a three membered hydrocarbon moiety to form a fused five membered aromatic ring, which moiety has one carbon atom replaced by >O, >S, >NH or >N(C$_{1-4}$alkyl) and which moiety has up to one additional carbon atom optionally replaced by N, the fused rings optionally mono-, di- or tri-substituted with R$_p$;
e) a monocyclic aromatic hydrocarbon group having six ring carbon atoms, having a carbon atom which is the point of attachment, having zero, one or two carbon atoms replaced by N, and having attachment at two adjacent carbon ring members to a four membered hydrocarbon moiety to form a fused six membered aromatic ring, which moiety has zero, one or two carbon atoms replaced by N, the fused rings optionally mono-, di- or tri-substituted with R$_p$;
f) a monocyclic aromatic hydrocarbon group having five ring carbon atoms, having a carbon atom which is the point of attachment, having one carbon atom replaced by >O, >S, >NH or >N(C$_{1-4}$alkyl), having up to one additional carbon atom optionally replaced by N, and optionally mono- or di-substituted with R$_p$;
g) a monocyclic aromatic hydrocarbon group having five ring carbon atoms, having a carbon atom which is the point of attachment, having one carbon atom replaced by >O, >S, >NH or >N(C$_{1-4}$alkyl), and having attachment at two adjacent carbon ring members to a four membered hydrocarbon moiety to form a fused six membered aromatic ring, which moiety has zero, one or two carbon atoms replaced by N, the fused rings optionally mono-, di- or tri-substituted with R$_p$;
h) a 4–7 membered aliphatic or heterocyclic ring said heterocyclic ring having a carbon atom which is the point of attachment, having 0 or 1 heteroatom members selected from O, S, —N=, >NH or >NR$_p$, having 0, 1 or 2 unsaturated bonds, having 0, 1 or 2 carbon members which is a carbonyl and having 0, 1 or 2 substituents R$_p$,
i) a benzo fused 4–7 membered aliphatic or heterocyclic ring said heterocyclic ring having a carbon atom which is the point of attachment, having 0 or 1 additional heteroatom members selected from O, S, —N=, >NH or >NR$_p$, having 0 or 1 additional unsaturated bonds, having 0, 1 or 2 carbon members which is a carbonyl, having 0, 1, 2, or 3 halo substituents on the benzene ring only and having 0, 1 or 2 substituents R$_p$, and enantiomers, diastereomers and pharmaceutically acceptable salts, esters or amides thereof.

In one aspect, the invention provides a method for treating a subject suffering from cancer, said method comprising administering to said subject a therapeutically effective amount of a pharmaceutical composition comprising a compound of formula (I). According to one aspect, the cancer is p-53 deficient.

In another aspect, the invention provides a method for treating a subject suffering from a p53-deficient tumor, said method comprising (a) administering to said subject a therapeutically effective amount of a pharmaceutical composition comprising a compound of formula (I) and (b) damaging the DNA of said subject, for example, by administration of a DNA-damaging treatment or agent, such as ionizing radiation or a chemical agent that causes DNA damage. In one aspect, the DNA damaging treatment is provided such that administration of the compound of formula (I) provides effective serum levels of the compound of formula (I) during the treatment and 12 hours to 5 days thereafter, for example, 1–2 days thereafter. In a further aspect, the method of treatment further includes administration of one or more additional anti-cancer agents, to provide in total three or four (or more) agents, to be administered in an effective anti-cancer amount. Multiple or combination therapies may allow use of lower amounts of one or more of the individual agents, when compared with monotherapy, and thereby reducing the incidence or degree of adverse effects.

Examples of such DNA-damaging chemical agents are compounds that cause DNA strand breaks directly such as bleomycin. DNA damage may also be caused by alkylating agents such as hexamethylamine, busulfan, carboplatin, carmustine, cisplatinum, cyclophosphamide, dacarbazine, ifosfamide, lomustine, mechlorethamine, melphalan, procarbazine, streptozocin or thiotepa, or combinations thereof. DNA damage may also be caused indirectly by topoisomerase inhibitors such as etoposide, irinotecan, teniposide, topotecan, and doxorubicin or by antimetabolites such as cladribine, cytarabine, floxuridine, 5-fluorouracil, gemcitibine, hydroxyurea, mercaptopurine, methotreaxate, pentostatin, thioguanine, and triemtrexate. Enhancement of DNA damaging effects and improved therapeutic responses can be obtained by combining anticancer agents such as those exemplified above.

A third aspect of the invention provides the use, or the use for the manufacture of a medicament, of a disclosed compound for treating a tumor, in particular, a p53 deficient tumor, and more in particular, a tumor selected from lung, prostate, colon, brain, head and neck, and breast. Other tumors include tumors of the stomach, liver, and ovary. A p-53 deficient tumor is a tumor wherein the functions mediated by p53 are lacking or suppressed due to genetic mutations in the gene encoding p53 or through deficiencies or disregulation of proteins that modulate p53 expression levels and function. Examples of such proteins are MDM2 and p14(ARF). A further aspect of the invention includes the treatment of a late-stage, e.g., stage 3 or stage 4, tumor.

The invention also features anti-cancer pharmaceutical compositions comprising as active ingredient an effective amount of a disclosed compound of formula (I), and a pharmaceutically acceptable carrier. The active ingredient can be formulated in any manner suitable for the particular tumor, including aerosol, oral, injectable and topical formulations, and time-release formulations thereof.

Additional features and advantages of the invention will become apparent from the detailed description and examples below, and the appended claims.

DETAILED DESCRIPTION OF THE INVENTION

Preferably, W is —(CO)NH$_2$.
Preferably, Q is CH.
Preferably, R$_a$ and R$_b$ are —H, —Cl or —F.
More preferably, R$_a$ is —H and R$_b$ is —Cl or —F.
Most preferably, R$_a$ and R$_b$ are —H.
Preferably, R$_c$ is absent or is selected from the group consisting of —OH, —CH$_3$, —CH$_2$CH$_3$, —F, —Cl, —Br, —I, —CF$_3$ and —OCH$_3$.
Most preferably, R$_c$ is selected from the group consisting of —F, —Cl, —CH$_3$ and —OCH$_3$.
Most preferably, R$_c$ is absent.
Preferably, R$_d$ is selected from the group consisting of —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$ and —C(CH$_3$)$_3$.
Most preferably, R$_d$ is selected from the group consisting of —H, —CH$_3$ and —CH$_2$CH$_3$.
Preferably, R$_e$ is selected from the group consisting of —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$ and —C(CH$_3$)$_3$, where the alkyl members are optionally mono- or di-substituted. Preferably the optional substituent is independently selected from the group consisting of —NH$_2$, —NHCH$_3$, —NHCH$_2$CH$_3$, —N(CH$_3$)$_2$, —N(CH$_2$CH$_3$)$_2$, —CONH$_2$, —CONHCH$_3$, —CONHCH$_2$CH$_3$, —CON(CH$_3$)$_2$, —CON(CH$_2$CH$_3$)$_2$, —COOH, —COOCH$_3$, —COOCH$_2$CH$_3$, —CN, —OH, —OCH$_3$, —OCH$_2$CH$_3$ and —OCH$_2$CH$_2$CH$_3$.

Most preferably, R$_e$ is selected from the group consisting of —H, —CH$_3$ and —CH$_2$CH$_3$, where the alkyl members are optionally mono- or di-substituted. Most preferably the optional substituent is independently selected from the group consisting of —NH$_2$, —NHCH$_3$, —N(CH$_3$)$_2$, —CONH$_2$, —CONHCH$_3$, —CON(CH$_3$)$_2$, —COOH, —COOCH$_3$, —CN, —OH and —OCH$_3$.

Most preferably, R$_e$ is —H or —CH$_3$.

Preferably, R$_d$ and R$_e$ taken together with their atoms of attachment form a heterocyclic ring selected from the group consisting of

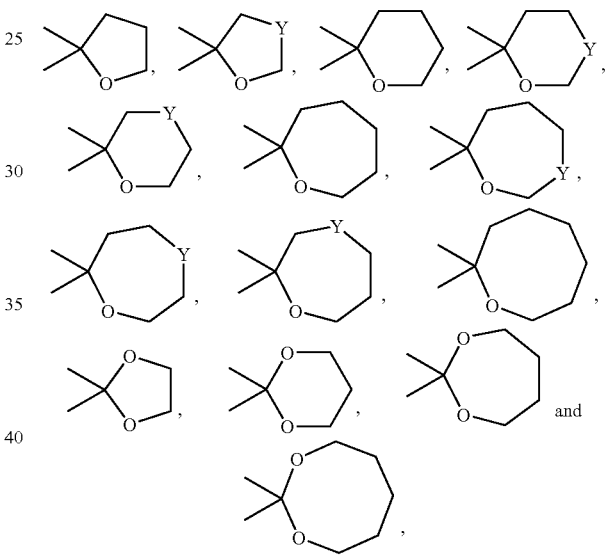

said heterocyclic ring having 0 or 1 unsaturated bonds and having 0, 1 or 2 carbon members which is a carbonyl, where Y is selected from O, S, —N=, >NH or >NC$_{1-4}$alkyl.

More preferably, R$_d$ and R$_e$ taken together with their atoms of attachment form a heterocyclic ring selected from the group consisting of

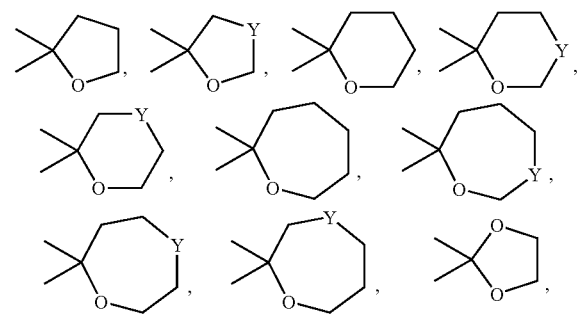

-continued

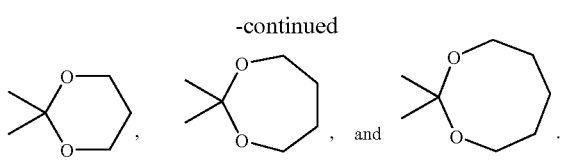

where Y is selected from O, >NH or >NC$_{1-4}$alkyl.

More preferably, R$_d$ and R$_e$ taken together with their atoms of attachment form a heterocyclic ring selected from the group consisting of

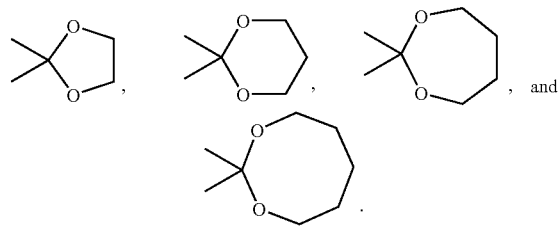

Most preferably, R$_d$ and R$_e$ taken together with their atoms of attachment form a heterocyclic ring selected from the group consisting of

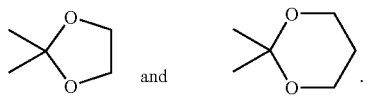

Preferably, R$_f$ is selected from the group consisting of —H, —CONH$_2$, —CONHCH$_3$, —CONHCH$_2$CH$_3$, —CON(CH$_3$)$_2$, —CON(CH$_2$CH$_3$)$_2$, —COOH, —COOCH$_3$, —COOCH$_2$CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$ and —C(CH$_3$)$_3$, where the alkyl members are optionally mono- or di-substituted. Preferably, the optional substituents are independently selected from the group consisting of —NH$_2$, —NHCH$_3$, —NHCH$_2$CH$_3$, —N(CH$_3$)$_2$, —N(CH$_2$CH$_3$)$_2$, —CONH$_2$, —CONHCH$_3$, —CONHCH$_2$CH$_3$, —CON(CH$_3$)$_2$, —CON(CH$_2$CH$_3$)$_2$, —COOH, —COOCH$_3$, —COOCH$_2$CH$_3$, —CN, —OH, —OCH$_3$, —OCH$_2$CH$_3$ and —OCH$_2$CH$_2$CH$_3$.

More preferably, R$_f$ is selected from the group consisting of —H, —CONH$_2$, —CONHCH$_3$, —CON(CH$_3$)$_2$, —COOH, —COOCH$_3$, —CH$_3$ and —CH$_2$CH$_3$, where the alkyl members are optionally mono- or di-substituted. Most preferably, the optional substituent is independently selected from the group consisting of —NH$_2$, —NHCH$_3$, —N(CH$_3$)$_2$, —CONH$_2$, —CONHCH$_3$, —CON(CH$_3$)$_2$, —COOH, —COOCH$_3$, —CN, —OH and —OCH$_3$.

Most preferably, R$_f$ is selected from the group consisting of —H and —CH$_3$.

Preferably, R$_g$ is selected from the group consisting of —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$ and —C(CH$_3$)$_3$, where the alkyl moieties are optionally mono- or di-substituted. Preferably, the optional substituent is independently selected from the group consisting of —NH$_2$, —NHCH$_3$, —NHCH$_2$CH$_3$, —N(CH$_3$)$_2$, —N(CH$_2$CH$_3$)$_2$, —CONH$_2$, —CONHCH$_3$, —CONHCH$_2$CH$_3$, —CON(CH$_3$)$_2$, —CON (CH$_2$CH$_3$)$_2$, —COOH, —COOCH$_3$, —COOCH$_2$CH$_3$, —CN, —OH, —OCH$_3$, —OCH$_2$CH$_3$ and —OCH$_2$CH$_2$CH$_3$.

Most preferably, R$_g$ is selected from the group consisting of —H, —CH$_3$ and —CH$_2$CH$_3$ where the alkyl members are optionally mono- or di-substituted. Most preferably the optional substituent is independently selected from the group consisting of —NH$_2$, —NHCH$_3$, —N(CH$_3$)$_2$, —CONH$_2$, —CONHCH$_3$, —CON(CH$_3$)$_2$, —COOH, —COOCH$_3$, —CN, —OH and —OCH$_3$.

Preferably, R$_d$ and R$_g$ taken together with their nitrogen of attachment to form a heterocyclic ring are selected from the group consisting of

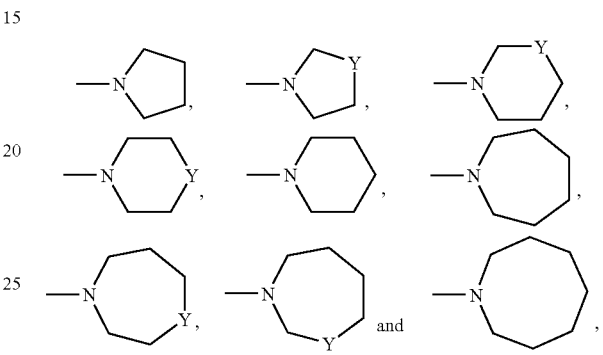

the heterocyclic ring having 0 or 1 unsaturated bonds and having 0, 1 or 2 carbon members which is a carbonyl, where Y is selected from O, S, —N=, >NH or >NC$_{1-4}$alkyl.

More preferably, R$_d$ and R$_g$ taken together with their atoms of attachment to form a heterocyclic ring are selected from the group consisting of

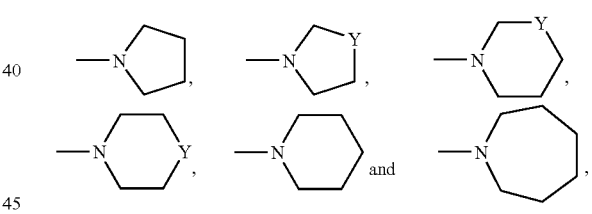

where Y is selected from O, S, >NH or >NC$_{1-4}$alkyl.

Most preferably, R$_d$ and R$_g$ taken together with their atoms of attachment to form a heterocyclic ring are selected from the group consisting of

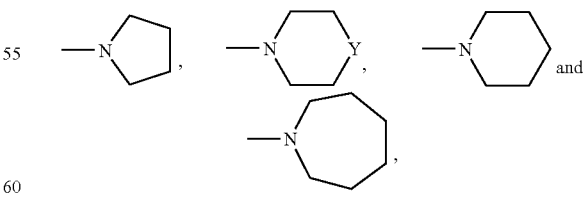

where Y is selected from O, S, >NH or >NC$_{1-4}$alkyl.

Preferably, R$_h$ is selected from the group consisting of —H, —CONH$_2$, —CONHCH$_3$, —CONHCH$_2$CH$_3$, —CON(CH$_3$)$_2$, —CON(CH$_2$CH$_3$)$_2$, —COOH, —COOCH$_3$, —COOCH$_2$CH$_3$, —CH$_3$, —CH$_2$CH$_3$, —CH$_2$CH$_2$CH$_3$, —CH(CH₃)₂, —CH₂CH₂CH₂CH₃, —CH(CH₃)CH₂CH₃ and —C(CH₃)₃, where the alkyl members are optionally mono- or di-substituted. Preferably the optional substituent is independently selected from the group consisting of —NH₂, —NHCH₃, —NHCH₂CH₃, —N(CH₃)₂, —N(CH₂CH₃)₂, —CONH₂, —CONHCH₃, —CONHCH₂CH₃, —CON(CH₃)₂, —CON(CH₂CH₃)₂, —COOH, —COOCH₃, —COOCH₂CH₃, —CN, —OH, —OCH₃, —OCH₂CH₃ and —OCH₂CH₂CH₃. Alternatively, $R_h$ is —CH₂CH₂— or —CH₂CH₂CH₂—, which is bonded to a carbon of A adjacent to the carbon of Z attachment, forming a five- or six-membered carbocyclic ring.

More preferably, $R_h$ is selected from the group consisting of —H, —CONH₂, —CONHCH₃, —CON(CH₃)₂, —COOH, —COOCH₃, —CH₃ and —CH₂CH₃, where the alkyl members are optionally mono- or di-substituted. Most preferably, the optional substituent is independently selected from the group consisting of —NH₂, —NHCH₃, —N(CH₃)₂, —CONH₂, —CONHCH₃, —CON(CH₃)₂, —COOH, —COOCH₃, —CN, —OH and —OCH₃. Alternatively, $R_h$ is —CH₂CH₂— or —CH₂CH₂CH₂—, which taken together with A forms indanyl or 1,2,3,4-tetrahydronaphthalenyl.

Most preferably, $R_h$ is selected from the group consisting of —H, —CH₃ and —CH₂CH₃.

Preferably, $R_i$ is selected from the group consisting of —H, —OH, —OCH₃, —OCH₂CH₃, —OCH₂CH₂CH₃, —CH₃, —CH₂CH₃, —CH₂CH₂CH₃, —CH(CH₃)₂, —CH₂CH₂CH₂CH₃, —CH(CH₃)CH₂CH₃ and —C(CH₃)₃, where the directly attached alkyl members are optionally mono- or di-substituted. Preferably the optional substituent is independently selected from the group consisting of —NH₂, —NHCH₃, —NHCH₂CH₃, —N(CH₃)₂, —N(CH₂CH₃)₂, —CONH₂, —CONHCH₃, —CONHCH₂CH₃, —CON(CH₃)₂, —CON(CH₂CH₃)₂, —COOH, —COOCH₃, —COOCH₂CH₃, —CN, —OH, —OCH₃, —OCH₂CH₃ and —OCH₂CH₂CH₃.

Most preferably, $R_i$ is selected from the group consisting of —H, —OH, —OCH₃, —CH₃ and —CH₂CH₃, where the directly attached alkyl members are optionally mono- or di-substituted. Most preferably, the optional substituent is independently selected from the group consisting of —NH₂, —NHCH₃, —N(CH₃)₂, —CONH₂, —CONHCH₃, —CON(CH₃)₂, —COOH, —COOCH₃, —CN, —OH and —OCH₃.

Preferably Z is selected from the group consisting of
a) >C=O, >C=CH₂, >CH₂, >CHC₁₋₄alkyl, >CF₂, >CHOH, >CHOC₁₋₄alkyl,

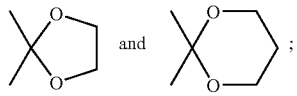

b) >CHN$R_d$$R_g$;
c) —SO₂N$R_d$CH($R_h$)—,

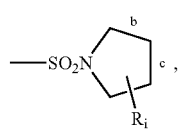

where A is fused at the c face, at a face of A which contains two carbon atoms, which is saturated or unsaturated,

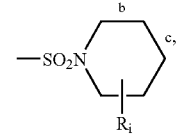

where A is fused at the c face, at a face of A which contains two carbon atoms, which is saturated or unsaturated,
d) >NCH₃, >NCH₂CH₃, >NCH₂CH₂CH₃, >NCH(CH₃)₂, >NCH₂CH₂CH₂CH₃, and >NCH(CH₃)CH₂CH₃, where the alkyl attached to >N is optionally substituted with a substituent selected from the group consisting of —NH₂, —NHCH₃, —NHCH₂CH₃, —N(CH₃)₂, —N(CH₂CH₃)₂, —CONH₂, —CONHCH₃, —CONHCH₂CH₃, —CON(CH₃)₂, —CON(CH₂CH₃)₂, —COOH, —COOCH₃, —COOCH₂CH₃, —OH, —OCH₃, —OCH₂CH₃ and —OCH₂CH₂CH₃.

Most preferably, Z is selected from the group consisting of
a) >C=O, >C=CH$R_f$, >CH$R_d$, >CF₂, >CHO$R_e$,

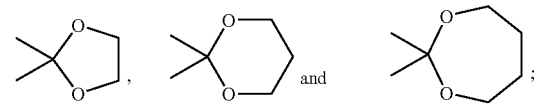

b) >CHNH$R_g$, >CHNCH₃$R_g$,

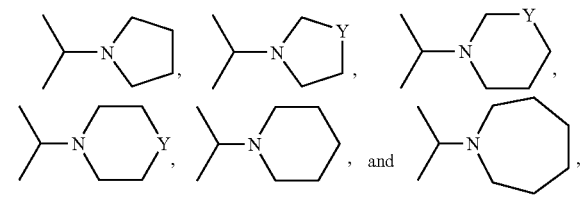

where Y is selected from O, S, —N=, >NH or >NC₁₋₄alkyl;
c) —SO₂NHCH₂—, —SO₂NCH₃CH₂—,

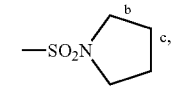

where A is fused at the c face, at a face of A which contains two carbon atoms, which is saturated or unsaturated,

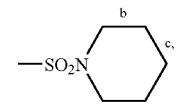

where A is fused at the c face, at a face of A which contains two carbon atoms, which is saturated or unsaturated,
d) >NCH₃, >NCH₂CH₃, >NCH₂CH₂CH₃, >NCH(CH₃)₂, where the alkyl attached to >N is optionally substituted with a substituent selected from the group consisting of —NH$_2$, —NHCH$_3$, —NHCH$_2$CH$_3$, —N(CH$_3$)$_2$, —N(CH$_2$CH$_3$)$_2$, —CONH$_2$, —CONHCH$_3$, —CONHCH$_2$CH$_3$, —CON(CH$_3$)$_2$, —CON(CH$_2$CH$_3$)$_2$, —COOH, —COOCH$_3$, —COOCH$_2$CH$_3$, —OH, —OCH$_3$, —OCH$_2$CH$_3$ and —OCH$_2$CH$_2$CH$_3$.

Preferably, A, optionally substituted with R$_p$, is selected from the group consisting of:
a) phenyl,
b) tetralin-5, 6, 7 or 8-yl, chroman-5, 6, 7 or 8-yl, benzo-1,2-pyran-5, 6, 7 8-yl, benzo-2,3-pyron-5, 6, 7 or 8-yl, coumarin-5, 6, 7 or 8-yl, isocoumarin-5, 6, 7 or 8-yl, benzo-1,3,2-benzoxazin-5, 6, 7 or 8-yl, benzo-1,4-dioxan-5, 6, 7 or 8-yl, 1,2,3,4-tetrahydroquinolin-5, 6, 7 or 8-yl, 1,2,3,4-tetrahydroquinoxalin-5, 6, 7 or 8-yl, thiochroman-5, 6, 7 or 8-yl, 2,3-dihydrobenzo[1,4]dithiin-5, 6, 7 or 8-yl, 1,2,3,4-tetrahydroisoquinolin-5, 6, 7 or 8-yl, indene-4, 5, 6, or 7-yl, 1,2,3,4-tetrahydronapth-5, 6, 7, or 8 yl, 1,2-dihydroisoindolo-4, 5, 6, or 7-yl, 2,3-dihydroindene-4, 5, 6, or 7-yl, benzo-1,3-dioxol-4, 5, 6 or 7-yl, 2,3-dihydroindol-4, 5, 6 or 7-yl, 2,3-dihydrobenzofuran-4, 5, 6 or 7-yl, 2,3-dihydrobenzothiophen-4, 5, 6 or 7-yl, 2,3-dihydrobenzoimidazol-4, 5, 6 or 7-yl,
c) pyridinyl, pyrazinyl, pyrimidinyl, pyridazinyl,
d) benzoxazol-4, 5, 6 or 7-yl, benzothiophen-4, 5, 6 or 7-yl, benzofuran-4, 5, 6 or 7-yl, indol-4, 5, 6 or 7-yl, benzthiazol-4, 5, 6 or 7-yl, benzimidazo-4, 5, 6 or 7-yl, indazol-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, purin-2-yl,
e) isoquinolin-5, 6, 7 or 8-yl, quinolin-5, 6, 7 or 8-yl, quinoxalin-5, 6, 7 or 8-yl, quinazolin-5, 6, 7 or 8-yl, naphthyridinyl,
f) furanyl, oxazolyl, isoxazolyl, thiophenyl, thiazolyl, isothiazolyl, pyrrolyl, imidazolyl, pyrazolyl, and
g) benzoxazol-2-yl, benzothiophen-2 or 3-yl, benzofuran-2 or 3-yl, indol-2 or 3yl, benzthiazol-2-yl, benzimidazo-2-yl, indazol-3-yl, 1H-pyrrolo[2,3-b]pyridin-2 or 3-yl, 1H-pyrrolo[3,2-c]pyridin-2 or 3-yl, 1H-pyrrolo[2,3-c]pyridin-2 or 3-yl, 1H-pyrrolo[3,2-b]pyridin-2 or 3-yl, purin-8-yl.

More preferably, A, optionally substituted with R$_p$, is selected from the group consisting of:
a) phenyl,
b) coumarin-5, 6, 7 or 8-yl, benzo-1,4-dioxan-5, 6, 7 or 8-yl, 1,2,3,4-tetrahydroquinolin-5, 6, 7 or 8-yl, 1,2,3,4-tetrahydroisoquinolin-5, 6, 7 or 8-yl, indene-4, 5, 6, or 7-yl, 1,2,3,4-tetrahydronapth-5, 6, 7, or 8 yl, 1,2-dihydroisoinrdolo-4, 5, 6, or 7-yl, 2,3-dihydroindene-4, 5, 6, or 7-yl, benzo-1,3-dioxol-4, 5, 6 or 7-yl, 2,3-dihydroindol-4, 5, 6 or 7-yl, 2,3-dihydrobenzofuran-4, 5, 6 or 7-yl, 2,3-dihydrobenzothiophen-4, 5, 6 or 7-yl,
c) pyridinyl, pyrazinyl, pyrimidinyl, pyridazinyl,
d) benzothiophen-4, 5, 6 or 7-yl, benzofuran-4, 5, 6 or 7-yl, indol-4, 5, 6 or 7-yl,
e) isoquinolin-5, 6, 7 or 8-yl, quinolin-5, 6, 7 or 8-yl,
f) furanyl, oxazolyl, isoxazolyl, thiophenyl, thiazolyl, isothiazolyl, pyrrolyl, imidazolyl, pyrazolyl, and
g) benzoxazol-2-yl, benzothiophen-2 or 3-yl, benzofuran-2 or 3-yl, indol-2 or 3-yl.

Most preferably A, optionally substituted with R$_p$, is selected from the group consisting of: phenyl, benzo-1,4-dioxan-5, 6, 7 or 8-yl, indene-4, 5, 6, or 7-yl, 1,2,3,4-tetrahydronapth-5, 6, 7, or 8 yl, 2,3-dihydroindene-4, 5, 6, or 7-yl, benzo-1,3-dioxol-4, 5, 6 or 7-yl, 2,3-dihydroindol-4, 5, 6 or 7-yl, 2,3-dihydrobenzofuran-4, 5, 6 or 7-yl, 2,3-dihydrobenzothiophen-4, 5, 6 or 7-yl, pyridinyl, benzothiophen-4, 5, 6 or 7-yl, benzofuran-4, 5, 6 or 7-yl, indol-4, 5, 6 or 7-yl, furanyl, thiophenyl, pyrrolyl, pyrazolyl, and benzothiophen-2 or 3-yl, benzofuran-2 or 3-yl and indol-2 or 3-yl.

A specific A, including the R$_p$ substituent, is selected from the group consisting of pyridyl, phenyl, naphthyl, quinolinyl, cyclohexyl, 4-chloro phenyl, 4-methyl-3-chloro phenyl, 4-chloro-3-trifluoromethyl phenyl, 3,4-dichloro phenyl, 3-chloro-4-fluoro phenyl, 2-fluoro-5-trifluoromethyl, 4-chloro-3-fluoro phenyl, 3,4-dimethyl phenyl, 2-napthyl, 4-trifluoromethyl phenyl, 4-bromo phenyl, 4-fluoro-3-methyl phenyl, 3-chloro phenyl, tetrahydronapthyl, 5-chloro-2-methyl phenyl, 3-trifluoromethyl phenyl, 4-methoxy phenyl, 4-methyl phenyl, 3,4-dimethyl phenyl, 2-fluoro-3-trifluoromethyl phenyl, 2-chloro-4-methyl phenyl, 4-ethyl phenyl, 4-fluoro phenyl, 3,4-dimethoxy phenyl, 3,4-dimethoxy-5-bromo phenyl, 3-(dimethylamino) phenyl, 4-nitro phenyl, 4-cyano phenyl, 2-methoxy-4-methyl phenyl, 4-trifluoromethoxy phenyl, 2-chloro phenyl, 4-morpholino phenyl, 3-chloro phenyl, 2,3-dichloro phenyl benzo[1,3]dioxolyl, benzo[1,4]dioxinyl, 4-amino phenyl, 4-hydroxy phenyl, 4-bromo-3-hydroxy phenyl, 4-chloro-2-hydroxy phenyl, 4-chloro-3-hydroxy phenyl, 2,4-dichloro phenyl, 4-bromo-3-methoxy phenyl and 4-iodo phenyl.

A specific A, including the R$_p$ substituent, is selected from the group consisting of phenyl, 4-chlorophenyl, 4-methylphenyl, 4-methoxyphenyl, 2-naphthalenyl, 4-chloro-3-trifluoromethylphenyl, 3-bromo-4,5-dimethoxyphenyl, 3,4-dichlorophenyl, 3,4-dimethylphenyl, 4-ethylphenyl, benzo[1,3]dioxolyl, 2,3-dihydro-benzo[1,4]dioxinyl, 3-quinolinyl, 4-pyridyl, cyclohexyl, 4-tetrahydropyranyl, 2-thiophenyl, 6-chloro-benzo[1,3]dioxolyl, 2-chlorophenyl, 2,4-dichlorophenyl, 2-methoxyphenyl, 2-methylphenyl, 3-methylphenyl, and 2-furanyl.

Preferably R$_p$ is selected from the group consisting of —OH, —CH$_3$, —CH$_2$CH$_3$, —OCH$_3$, —OCH$_2$CH$_3$, —OCH(CH$_3$)$_2$, cyclopropyl, cyclobutyl, cyclopentyl, cyclohexyl, -Ocyclopentyl, -Ocyclohexyl, —CN, —NO$_2$, —C(O)NH$_2$, —C(O)N(CH$_3$)$_2$, —C(O)NH(CH$_3$), —NHCOCH$_3$, —NCH$_3$COCH$_3$, —NHSO$_2$CH$_3$, —NCH$_3$SO$_2$CH$_3$, —C(O)CH$_3$, —SOCH$_3$, —SO$_2$NH$_2$, —SO$_2$NHCH$_3$, —SO$_2$N(CH$_3$)$_2$, —SCF$_3$, —F, —Cl, —Br, I, —CF$_3$, —OCF$_3$, —COOH, —COOCH$_3$, —COOCH$_2$CH$_3$, —NH$_2$, —NHCH$_3$, —N(CH$_3$)$_2$, —N(CH$_2$CH$_3$)$_2$, —NCH$_3$(CH(CH$_3$)$_2$), imidazolidin-1-yl, 2-imidazolin-1-yl, pyrazolidin-1-yl, piperidin-1-yl, 2- or 3-pyrrolin-1-yl, 2-pyrazolinyl, morpholin-4-yl, thiomorpholin-4-yl, piperazin-1-yl, pyrrolidin-1-yl, homopiperidin-1-yl.

Most preferably R$_p$ is selected from the group consisting of —H, —OH, —OCH$_3$, —OCF$_3$, —CH$_3$, —CH$_2$CH$_3$, —CF$_3$, —F, —Cl, —Br, —I, —NH$_2$, —N(CH$_3$)$_2$, morpholin-4-yl, —NO$_2$, —CN, —C(O)NH$_2$, —COOH, —NHSO$_2$CH$_3$, —SO$_2$NH$_2$.

The invention features pharmaceutically active, substituted benzimidazole compounds as disclosed in the Summary section above.

A. Terms

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond (sp$^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 4 and 7 ring atoms, or between 5 and 6 ring atoms; there may be between 1 and 5 heteroatoms or heteroatom moieties in the ring, and preferably between 1 and 3. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazolyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably chloro or bromo as a substituent.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts (e.g., $C_{1-8}$ alkyl, $C_{3-8}$ cycloalkyl, aryl, $C_{2-10}$ heteroaryl, or $C_{2-10}$ non-aromatic heterocyclic) amino acid addition salts, esters, and amides that are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1–19, which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl ($C_{1-6}$)alkyl esters. Preferred esters include methyl esters.

"Patient" or "subject" includes mammals such as humans and animals (dogs, cats, horses, rats, rabbits, mice, nonhuman primates) in need of observation, experiment, treatment or prevention in connection with the relevant disease or condition. Preferably, the patient or subject is a human.

"Composition" includes a product comprising the specified ingredients in the specified amounts as well as any product that results directly or indirectly from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the condition or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is Z in formula (I), which links X and A.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent radicals such as alkylene, alkenylene, phenylene, and so on. Heterocarbyls include monovalent and divalent radicals containing carbon, hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, perfluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$ alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an NR'R" group, and R can be an alkenyl group, the double bond is at least one carbon removed from the nitrogen to avoid enamine formation. Similarly, where a dashed line is an optional $sp^2$ bond, if it is absent, the appropriate hydrogen atom(s) is (are) included.

Compounds of the invention are further described in the next section.

B. Compounds

The invention features the treatment, or inhibition of onset or progression, of cancer using one or more Cds1 inhibitors as described in the Summary section.

Preferred compounds are made according to the synthetic methods outlined in Schemes 1–9, have demonstrated Cds1 inhibitory activity, and are selected from the group consisting of:

| EX | Compound Name |
|---|---|
| 1 | 2-[4-(2-Phenyl-[1,3]dioxolan-2-yl)-phenyl]-1H-benzoimidazole-5-carboxylic acid amide; |
| 2 | 2-{4-[2-(4-Chloro-phenyl)-[1,3]dioxolan-2-yl]-phenyl}-1H benzoimidazole-5-carboxylic acid amide; |
| 3 | 2-(4-Benzoyl-phenyl)-1H-benzoimidazole-5-carboxylic acid amide; |
| 4 | 2-[4-(4-Chloro-benzoyl)-phenyl]-1H-benzoimidazole-5-carboxylic acid amide; |
| 5 | 2-[4-(4-Methyl-benzoyl)-phenyl]-1H-benzoimidazole-5-carboxylic acid amide; |
| 6 | 2-[4-(4-Methoxy-benzoyl)-phenyl]-1H-benzoimidazole-5-carboxylic acid amide; |
| 7 | 2-[4-(Naphthalene-2-carbonyl)-phenyl]-1H-benzoimidazole-5-carboxylic acid amide; |
| 8 | 2-[4-(4-Chloro-3-trifluoromethyl-benzoyl)-phenyl]-1H-benzoimidazole-5-carboxylic acid amide; |
| 9 | 2-[4-(3-Bromo-4,5-dimethoxy-benzoyl)-phenyl]-1H-benzoimidazole-5-carboxylic acid amide; |
| 10 | 2-[4-(3,4-Dichloro-benzoyl)-phenyl]-1H-benzoimidazole-5-carboxylic acid amide; |
| 11 | 2-[4-(3,4-Dimethyl-benzoyl)-phenyl]-1H-benzoimidazole-5-carboxylic acid amide; |
| 12 | 2-[4-(4-Ethyl-benzoyl)-phenyl]-1H-benzoimidazole-5-carboxylic acid amide; |
| 13 | 2-[4-(Benzo[1,3]dioxole-5-carbonyl)-phenyl]-1H-benzoimidazole-5-carboxylic acid amide; |
| 14 | 2-[4-(2,3-Dihydro-benzo[1,4]dioxine-6-carbonyl)-phenyl]-1H-benzoimidazole-5-carboxylic acid amide; |
| 15 | 2-[4-(Quinoline-3-carbonyl)-phenyl]-1H-benzoimidazole-5-carboxylic acid amide; |
| 16 | 2-[4-(Pyridine-4-carbonyl)-phenyl]-1H-benzoimidazole-5-carboxylic acid amide; |
| 17 | 2-(4-Cyclohexanecarbonyl-phenyl)-1H-benzoimidazole-5-carboxylic acid amide; |
| 18 | 2-[4-(4-Chloro-benzoyl)-phenyl]-1H-benzoimidazole-5-sulfonic acid amide; |
| 19 | 2-[4-(Hydroxy-phenyl-methyl)-phenyl]-1H-benzoimidazole-5-carboxylic acid amide; |
| 20 | 2-{4-[(4-Chloro-phenyl)-hydroxy-methyl]-phenyl}-1H-benzoimidazole-5-carboxylic acid amide; |
| 21 | 2-[4-(Hydroxy-p-tolyl-methyl)-phenyl]-1H-benzoimidazole-5-carboxylic acid amide; |
| 22 | 2-{4-[Hydroxy-(4-methoxy-phenyl)-methyl]-phenyl}-1H-benzoimidazole-5-carboxylic acid amide; |
| 23 | 2-[4-(Hydroxy-naphthalen-2-yl-methyl)-phenyl]-1H-benzoimidazole-5-carboxylic acid amide; |
| 24 | 2-{4-[(4-Chloro-3-trifluoromethyl-phenyl)-hydroxy-methyl]-phenyl}-1H-benzoimidazole-5-carboxylic acid amide; |
| 25 | 2-{4-[(3-Bromo-4,5-dimethoxy-phenyl)-hydroxy-methyl]-phenyl}-1H-benzoimidazole-5-carboxylic acid amide; |
| 26 | 2-{4-[(3,4-Dichloro-phenyl)-hydroxy-methyl]-phenyl}-1H-benzoimidazole-5-carboxylic acid amide; |
| 27 | 2-{4-[(3,4-Dimethyl-phenyl)-hydroxy-methyl]-phenyl}-1H-benzoimidazole-5-carboxylic acid amide; |
| 28 | 2-{4-[(4-Ethyl-phenyl)-hydroxy-methyl]-phenyl}-1H-benzoimidazole-5-carboxylic acid amide; |
| 29 | 2-[4-(Benzo[1,3]dioxol-5-yl-hydroxy-methyl)-phenyl]-1H-benzoimidazole-5-carboxylic acid amide; |
| 30 | 2-{4-[(2,3-Dihydro-benzo[1,4]dioxin-6-yl)-hydroxy-methyl]-phenyl}-1H-benzoimidazole-5-carboxylic acid amide; |
| 31 | 2-[4-(Hydroxy-quinolin-3-yl-methyl)-phenyl]-1H-benzoimidazole-5-carboxylic acid amide; |
| 32 | 2-[4-(Hydroxy-pyridin-4-yl-methyl)-phenyl]-1H-benzoimidazole-5-carboxylic acid amide; |
| 33 | 2-[4-(Cyclohexyl-hydroxy-methyl)-phenyl]-1H-benzoimidazole-5-carboxylic acid amide; |
| 34 | 2-[4-(Methoxy-phenyl-methyl)-phenyl]-1H-benzoimidazole-5-carboxylic acid amide; |
| 35 | 2-[4-(4-Chloro-benzyl)-phenyl]-1H-benzoimidazole-5-carboxylic acid amide; |
| 36 | 2-(4-Naphthalen-2-ylmethyl-phenyl)-1H-benzoimidazole-5-carboxylic acid amide; |

| EX | Compound Name |
|---|---|
| 37 | 2-[4-(3,4-Dimethyl-benzyl)-phenyl]-1H-benzoimidazole-5-carboxylic acid amide; |
| 38 | 2-[4-(4-Ethyl-benzyl)-phenyl]-1H-benzoimidazole-5-carboxylic acid amide; |
| 39 | 2-[4-(2,3-Dihydro-benzo[1,4]dioxin-6-ylmethyl)-phenyl]-1H-benzoimidazole-5-carboxylic acid amide; |
| 40 | 2-(4-Cyclohexylmethyl-phenyl)-1H-benzoimidazole-5-carboxylic acid amide; |
| 41 | 2-{4-[1-(4-Chloro-phenyl)-vinyl]-phenyl}-1H-benzoimidazole-5-carboxylic acid amide; |
| 42 | 2-{4-[1-(4-Chloro-phenyl)-ethyl]-phenyl}-1H-benzoimidazole-5-carboxylic acid amide; |
| 43 | 2-{4-[(4-Chloro-phenyl)-piperazin-1-yl-methyl]-phenyl}-1H-benzoimidazole-5-carboxylic acid amide; |
| 44 | 2-(4-{(4-Chloro-phenyl)-[methyl-(2-methylamino-ethyl)-amino]-methyl}-phenyl)-1H-benzoimidazole-5-carboxylic acid amide; |
| 45 | 2-[4-(Methyl-phenyl-amino)-phenyl]-1H-benzoimidazole-5-carboxylic acid amide; |
| 46 | 2-(4-Benzylsulfamoyl-phenyl)-1H-benzoimidazole-5-carboxylic acid amide; |
| 47 | 2-[4-(4-Methyl-benzylsulfamoyl)-phenyl]-1H-benzoimidazole-5-carboxylic acid amide; |
| 48 | 2-[4-(4-Methoxy-benzylsulfamoyl)-phenyl]-1H-benzoimidazole-5-carboxylic acid amide; |
| 49 | 2-[4-(4-Chloro-benzylsulfamoyl)-phenyl]-1H-benzoimidazole-5-carboxylic acid amide; |
| 50 | 2-[4-(3,4-Dichloro-benzylsulfamoyl)-phenyl]-1H-benzoimidazole-5-carboxylic acid amide; |
| 51 | 2-[4-(Benzyl-methyl-sulfamoyl)-phenyl]-1H-benzoimidazole-5-carboxylic acid amide; |
| 52 | 2-[4-(Tetrahydro-pyran-4-carbonyl)-phenyl]-1H-benzoimidazole-5-carboxylic acid amide; |
| 53 | 2-[4-(Thiophene-2-carbonyl)-phenyl]-1H-benzoimidazole-5-carboxylic acid amide; |
| 54 | 2-[4-(6-Chloro-benzo[1,3]dioxole-5-carbonyl)-phenyl]-1H-benzoimidazole-5-carboxylic acid amide; |
| 55 | 2-[4-(2-Chloro-benzoyl)-phenyl]-1H-benzoimidazole-5-carboxylic acid amide; |
| 56 | 2-[4-(2,4-Dichloro-benzoyl)-phenyl]-1H-benzoimidazole-5-carboxylic acid amide; |
| 57 | 2-[4-(2-Methoxy-benzoyl)-phenyl]-1H-benzoimidazole-5-carboxylic acid amide; |
| 58 | 2-[4-(2-Methyl-benzoyl)-phenyl]-1H-benzoimidazole-5-carboxylic acid amide; |
| 59 | 2-{4-[Hydroxy-(tetrahydro-pyran-4-yl)-methyl]-phenyl}-1H-benzoimidazole-5-carboxylic acid amide; |
| 60 | 2-[4-(Hydroxy-thiophen-2-yl-methyl)-phenyl]-1H-benzoimidazole-5-carboxylic acid amide; |
| 61 | 2-{4-[(6-Chloro-benzo[1,3]dioxol-5-yl)-hydroxy-methyl]-phenyl}-1H-benzoimidazole-5-carboxylic acid amide; |
| 62 | 2-{4-[(2-Chloro-phenyl)-hydroxy-methyl]-phenyl}-1H-benzoimidazole-5-carboxylic acid amide; |
| 63 | 2-{4-[(2,4-Dichloro-phenyl)-hydroxy-methyl]-phenyl}-1H-benzoimidazole-5-carboxylic acid amide; |
| 64 | 2-{4-[Hydroxy-(2-methoxy-phenyl)-methyl]-phenyl}-1H-benzoimidazole-5-carboxylic acid amide; |
| 65 | 2-[4-(Hydroxy-o-tolyl-methyl)-phenyl]-1H-benzoimidazole-5-carboxylic acid amide; |
| 66 | 2-[4-(6-Chloro-benzo[1,3]dioxol-5-ylmethyl)-phenyl]-1H-benzoimidazole-5-carboxylic acid amide; |
| 67 | 2-[4-(2-Methoxy-benzyl)-phenyl]-1H-benzoimidazole-5-carboxylic acid amide; |
| 68 | 2-[4-(2-Methyl-benzyl)-phenyl]-1H-benzoimidazole-5-carboxylic acid amide; |
| 69 | 2-[4-(2-Methyl-benzylsulfamoyl)-phenyl]-1H-benzoimidazole-5-carboxylic acid amide; |
| 70 | 2-[4-(3-Methyl-benzylsulfamoyl)-phenyl]-1H-benzoimidazole-5-carboxylic acid amide; |
| 71 | 2-[4-(1,3-Dihydro-isoindole-2-sulfonyl)-phenyl]-1H-benzoimidazole-5-carboxylic acid amide; |
| 72 | 2-[4-(2,3-Dihydro-indole-1-sulfonyl)-phenyl]-1H-benzoimidazole-5-carboxylic acid amide; |
| 73 | (±)-2-[4-(1-Phenyl-ethylsulfamoyl)-phenyl]-1H-benzoimidazole-5-carboxylic acid amide; |
| 74 | (±)-2-[4-(1,2,3,4-Tetrahydro-naphthalen-1-ylsulfamoyl)-phenyl]-1H-benzoimidazole-5-carboxylic acid amide; |
| 75 | 2-{4-[(Thiophen-2-ylmethyl)-sulfamoyl]-phenyl}-1H-benzoimidazole-5-carboxylic acid amide; |
| 76 | 2-{4-[(Furan-2-ylmethyl)-sulfamoyl]-phenyl}-1H-benzoimidazole-5-carboxylic acid amide; |
| 77 | 2-{4-[(Pyridin-4-ylmethyl)-sulfamoyl]-phenyl}-1H-benzoimidazole-5-carboxylic acid amide; and |
| 78 | 2-[4-(S)-Indan-1-ylsulfamoyl)-phenyl]-1H-benzoimidazole-5-carboxylic acid amide. |

Also preferred are compounds selected from the group consisting of: 2-{4-[1-(4-Chloro-phenyl)-vinyl]-phenyl}-1H-imidazo[4,5-b]pyridine-5-carboxylic acid amide; 2-{4-[(2,4-Dichloro-phenyl)-hydroxy-methyl]-phenyl}-1H-benzoimidazole-5-carboxylic acid amide; 2-[4-(3,4-Dihydro-1H-isoquinoline-2-sulfonyl)-phenyl]-1H-benzoimidazole-5-carboxylic acid amide; 2-(4-Thiophen-2-ylmethyl-phenyl)-1H-benzoimidazole-5-carboxylic acid amide; 2-[4-(Furan-3-carbonyl)-phenyl]-1H-benzoimidazole-5-carboxylic acid amide; 2-[4-(Furan-3-yl-hydroxy-methyl)-phenyl]-1H-benzoimidazole-5-carboxylic acid amide; 2-(4-Furan-3-ylmethyl-phenyl)-1H-benzoimidazole-5-carboxylic acid amide; 2-[4-(1-Methyl-1H-imidazole-2-carbonyl)-phenyl]-1H-benzoimidazole-5-carboxylic acid amide; 2-{4-[Hydroxy-(1-methyl-1H-imidazol-2-yl)-methyl]-phenyl}-1H-benzoimidazole-5-carboxylic acid amide; 2-[4-(1-Methyl-1H-imidazol-2-ylmethyl)-phenyl]-1H-benzoimidazole-5-carboxylic acid amide; 2-[4-(5-Chloro-thiophene-2-carbonyl)-phenyl]-1H-benzoimidazole-5-carboxylic acid amide; 2-{4-[(5-Chloro-thiophen-2-yl)-hydroxy-methyl]-phenyl}-1H-benzoimidazole-5-carboxylic acid amide; 2-[4-(5-Chloro-thiophen-2-ylmethyl)-phenyl]-1H-benzoimidazole-5-carboxylic acid amide; 2-[4-(Piperidine-4-carbonyl)-phenyl]-1H-benzoimidazole-5-carboxylic acid amide; 2-[4-(Hydroxy-piperidin-4-yl-methyl)-phenyl]-1H-benzoimidazole-5-carboxylic acid amide; 2-(4-Piperidin-4-ylmethyl-phenyl)-1H-benzoimidazole-5-carboxylic acid amide; 2-[4-(Tetrahydro-thiopyran-4-carbonyl)-phenyl]-1H-benzoimidazole-5-carboxylic acid amide; 2-{4-[Hydroxy-(tetrahydro-thiopyran-4-yl)-methyl]-phenyl}-1H-benzoimidazole-5-carboxylic acid amide; 2-[4-(Tetrahydro-thiopyran-4-ylmethyl)-phenyl]-1H-benzoimidazole-5-carboxylic acid amide; 2-[4-(Tetrahydro-pyran-4-ylmethyl)-phenyl]-1H-benzoimidazole-5-carboxylic acid amide; [[4-(5-Carbamoyl-1H-benzoimidazol-2-yl)-phenyl]-(4-chloro-phenyl)-methoxy]-acetic acid; 2-{4-[(2-Amino-ethoxy)-(4-chloro-phenyl)-methyl]-phenyl}-1H-benzoimidazole-5-carboxylic acid amide; 2-{4-[(4-Chloro-phenyl)-difluoro-methyl]-phenyl}-1H-benzoimidazole-5-carboxylic acid amide; 2-[4-(Benzo[1,3]dioxol-5-yl-difluoro-methyl)-phenyl]-1H-benzoimidazole-5-carboxylic acid amide; 2-{4-[1-(4-Chloro-phenyl)-1-methyl-ethyl]-phenyl}-1H-benzoimidazole-5-carboxylic acid amide; 2-{4-[(4-Chloro-phenyl)-cyano-methyl]-phenyl}-1H-benzoimidazole-5-carboxylic acid amide; 2-[4-((S)-1-Hydroxymethyl-1,3-dihydro-isoindole-2-sulfonyl)-phenyl]-1H-benzoimidazole-5-carboxylic acid amide; 2-[4-(R)-1-Hydroxymethyl-1,3-dihydro-isoindole-2-sulfonyl)-phenyl]-1H-benzoimidazole-5-carboxylic acid amide; 2-[4-((1R,2S)-2-Hydroxy-indan-1-ylsulfamoyl)-phenyl]-1H-benzoimidazole-5-carboxylic acid amide; 2-[4-((S)-2-Hydroxy-1-phenyl-ethylsulfamoyl)-phenyl]-1H-benzoimidazole-5-carboxylic acid amide; 2-[4-((R)-2-Hydroxy-1-phenyl-ethylsulfamoyl)-phenyl]-1H-benzoimidazole-5-carboxylic acid amide; and 2-{4-[(Pyridin-2-ylmethyl)-sulfamoyl]-phenyl}-1H-benzoimidazole-5-carboxylic acid amide.

More preferred are compounds selected from the group consisting of: 2-[4-(4-Methyl-benzoyl)-phenyl]-1H-benzoimidazole-5-carboxylic acid amide; 2-[4-(Naphthalene-2-carbonyl)-phenyl]-1H-benzoimidazole-5-carboxylic acid amide; 2-[4-(4-Chloro-3-trifluoromethyl-benzoyl)-phenyl]-1H-benzoimidazole-5-carboxylic acid amide; 2-[4-(3-Bromo-4,5-dimethoxy-benzoyl)-phenyl]-1H-benzoimidazole-5-carboxylic acid amide; 2-[4-(3,4-Dichloro-benzoyl)-phenyl]-1H-benzoimidazole-5-carboxylic acid amide; 2-[4-(3,4-Dimethyl-benzoyl)-phenyl]-1H-benzoimidazole-5-carboxylic acid amide; 2-[4-($^4$-Ethyl-benzoyl)-phenyl]-1H-benzoimidazole-5-carboxylic acid amide; 2-(4-Cyclohexanecarbonyl-phenyl)-1H-benzoimidazole-5-carboxylic acid amide; 2-[4-(Hydroxy-phenyl-methyl)-phenyl]-1H-benzoimidazole-5-carboxylic acid amide; 2-{4-[(4-Chloro-phenyl)-hydroxy-methyl]-phenyl}-1H-benzoimidazole-5-carboxylic acid amide; 2-[4-(Hydroxy-p-tolyl-methyl)-phenyl]-1H-benzoimidazole-5-carboxylic acid amide; 2-{4-[Hydroxy-(4-methoxy-phenyl)-methyl]-phenyl}-1H-benzoimidazole-5-carboxylic acid amide; 2-[4-(Hydroxy-naphthalen-2-yl-methyl)-phenyl]-1H-benzoimidazole-5-carboxylic acid amide; 2-{4-[(4-Chloro-3-trifluoromethyl-phenyl)-hydroxy-methyl]-phenyl}-1H-benzoimidazole-5-carboxylic acid amide; 2-{4-[(3,4-Dichloro-phenyl)-hydroxy-methyl]-phenyl}-1H-benzoimidazole-5-carboxylic acid amide; 2-{4-[(3,4-Dimethyl-phenyl)-hydroxy-methyl]-phenyl}-1H-benzoimidazole-5-carboxylic acid amide; 2-{4-[(4-Ethyl-phenyl)-hydroxy-methyl]-phenyl}-1H-benzoimidazole-5-carboxylic acid amide; 2-[4-(Benzo[1,3]dioxol-5-yl-hydroxy-methyl)-phenyl]-1H-benzoimidazole-5-carboxylic acid amide; 2-[4-(Hydroxy-quinolin-3-yl-methyl)-phenyl]-1H-benzoimidazole-5-carboxylic acid amide; 2-[4-(4-Chloro-benzyl)-phenyl]-1H-benzoimidazole-5-carboxylic acid amide; 2-(4-Naphthalen-2-ylmethyl-phenyl)-1H-benzoimidazole-5-carboxylic acid amide; 2-[4-(3,4-Dimethyl-benzyl)-phenyl])-1H-benzoimidazole -5-carboxylic acid amide; 2-[4-(4-Ethyl-benzyl)-phenyl]-1H-benzoimidazole-5-carboxylic acid amide; 2-[4-(2,3-Dihydro-benzo[1,4]dioxin-6-ylmethyl)-phenyl]-1H-benzoimidazole-5-carboxylic acid amide; 2-{4-[1-(4-Chloro-phenyl)-vinyl]-phenyl}-1H-benzoimidazole-5-carboxylic acid amide; 2-{4-[1-(4-Chloro-phenyl)-ethyl]-phenyl}-1H-benzoimidazole-5-carboxylic acid amide; 2-[4-(1,3-Dihydro-isoindole-2-sulfonyl)-phenyl]-1H-benzoimidazole-5-carboxylic acid amide; 2-[4-(2,3-Dihydro-indole-1-sulfonyl)-phenyl]-1H-benzoimidazole-5-carboxylic acid amide; (±)-2-[4-(1,2,3,4-Tetrahydro-naphthalen-1-ylsulfamoyl)-phenyl]-1H-benzoimidazole-5-carboxylic acid amide; 2-{4-[(Thiophen-2-ylmethyl)-sulfamoyl]-phenyl}-1H-benzoimidazole-5-carboxylic acid amide; and 2-[4-(Indan(S)-1-ylsulfamoyl)-phenyl]-1H-benzoimidazole-5-carboxylic acid amide.

Most preferred are compounds selected from the group consisting of: 2-[4-(Naphthalene-2-carbonyl)-phenyl]-1H-benzoimidazole-5-carboxylic acid amide; 2-[4-(3,4-Dichloro-benzoyl)-phenyl]-1H-benzoimidazole-5-carboxylic acid amide; 2-{4-[(4-Chloro-phenyl)-hydroxy-methyl]-phenyl}-1H-benzoimidazole-5-carboxylic acid amide; 2-[4-(Hydroxy-naphthalen-2-yl-methyl)-phenyl]-1H-benzoimidazole-5-carboxylic acid amide; 2-{4-[(4-Chloro-3-trifluoromethyl-phenyl)-hydroxy-methyl]-phenyl}-1H-benzoimidazole-5-carboxylic acid amide; 2-{4-[(3,4-Dichloro-phenyl)-hydroxy-methyl]-phenyl}-1H-benzoimidazole-5-carboxylic acid amide; 2-{4-[(3,4-Dimethyl-phenyl)-hydroxy-methyl]-phenyl}-1H-benzoimidazole-5-carboxylic acid amide; 2-[4-(Hydroxy-quinolin-3-yl-methyl)-phenyl]-1H-benzoimidazole-5-carboxylic acid amide; 2-[4-(4-Chloro-benzyl)-phenyl]-1H-benzoimidazole-5-carboxylic acid amide; 2-(4-Naphthalen-2-ylmethyl-phenyl)-1H-benzoimidazole-5-carboxylic acid amide; 2-[4-(3,4-Dimethyl-benzyl)-phenyl]-1H-benzoimidazole-5-carboxylic acid amide; 2-{4-[1-(4-Chloro-phenyl)-vinyl]-phenyl}-1H-benzoimidazole-5-carboxylic acid amide; 2-{4-[1-(4-Chloro-phenyl)-ethyl]-phenyl}-1H-benzoimidazole-5-carboxylic acid amide; 2-[4-(1,3-Dihydro-isoindole-2-sulfonyl)-phenyl]-1H-benzoimidazole-5-carboxylic acid amide; and 2-[4-(S)-Indan-1-ylsulfamoyl)-phenyl]-1H-benzoimidazole-5-carboxylic acid amide.

Most preferred are compounds selected from the group consisting of: 2-[4-(Hydroxy-phenyl-methyl)-phenyl]-1H-benzoimidazole-5-carboxylic acid amide; 2-{4-[(4-Chloro-phenyl)-hydroxy-methyl]-phenyl}-1H-benzoimidazole-5-carboxylic acid amide; 2-[4-(Hydroxy-p-tolyl-methyl)-phenyl]-1H-benzoimidazole-5-carboxylic acid amide; 2-{4-[Hydroxy-(4-methoxy-phenyl)-methyl]-phenyl}-1H-benzoimidazole-5-carboxylic acid amide; 2-[4-(Hydroxy-naphthalen-2-yl-methyl)-phenyl]-1H-benzoimidazole-5-carboxylic acid amide; 2-{4-[(4-Chloro-3-trifluoromethyl-pheny)-hydroxy-methyl]-phenyl}-1H-benzoimidazole-5-carboxylic acid amide; 2-{4-[(3-Bromo-4,5-dimethoxy-phenyl)-hydroxy-methyl]-phenyl}-1H-benzoimidazole-5-carboxylic acid amide; 2-{4-[(3,4-Dichloro-phenyl)-hydroxy-methyl]-phenyl}-1H-benzoimidazole-5-carboxylic acid amide; 2-{4-[(3,4-Dimethyl-phenyl)-hydroxy-methyl]-phenyl}-1H-benzoimidazole-5-carboxylic acid amide; 2-{4-[(4-Ethyl-phenyl)-hydroxy-methyl]-phenyl}-1H-benzoimidazole-5-carboxylic acid amide; 2-[4-(Benzo[1,3]dioxol-5-yl-hydroxy-methyl)-phenyl]-1H-benzoimidazole-5-carboxylic acid amide; 2-{4-[(2,3-Dihydro-benzo[1,4]dioxin-6-yl)-hydroxy-methyl]-phenyl}-1H-benzoimidazole-5-carboxylic acid amide; 2-[4-(Hydroxy-quinolin-3-yl-methyl)-phenyl]-1H-benzoimidazole-5-carboxylic acid amide; 2-[4-(Hydroxy-pyridin-4-yl-methyl)-phenyl]-1H-benzoimidazole-5-carboxylic acid amide; 2-[4-(Cyclohexyl-hydroxy-methyl)-phenyl]-1H-benzoimidazole-5-carboxylic acid amide; 2-{4-[Hydroxy-(tetrahydro-pyran-4-yl)-methyl]-phenyl}-1H-benzoimidazole-5-carboxylic acid amide; 2-[4-(Hydroxy-thiophen-2-yl-methyl)-phenyl]-1H-benzoimidazole-5-carboxylic acid amide; 2-{4-[(6-Chloro-benzo[1,3]dioxol-5-yl)-hydroxy-methyl]-phenyl}-1H-benzoimidazole-5-carboxylic acid amide; 2-{4-[(2-Chloro-phenyl)-hydroxy-methyl]-phenyl}-1H-benzoimidazole-5-carboxylic acid amide; 2-{4-[(2,4-Dichloro-phenyl)-hydroxy-methyl]-phenyl}-1H-benzoimidazole-5-carboxylic acid amide; 2-{4-[Hydroxy-(2-methoxy-phenyl)-methyl]-phenyl}-1H-benzoimidazole-5-carboxylic acid amide; 2-[4-(Hydroxy-o-tolyl-methyl)-phenyl]-1H-benzoimidazole-5-carboxylic acid amide; and 2-{4-[(2,4-Dichloro-phenyl)-hydroxy-methyl]-phenyl}-1H-benzoimidazole-5-carboxylic acid amide.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{11}$C, or $^{18}$F for use as a molecular probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, Protective Groups in Organic Synthesis, 3$^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

C. Synthetic Methods

The invention provides methods of making the disclosed compounds according to traditional organic synthetic methods as well as matrix or combinatorial synthetic methods. Schemes 1 through 9 describe suggested synthetic routes. Using these Schemes, the guidelines below, and the examples, a person of skill in the art may develop analogous or similar methods for a given compound that are within the invention.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Examples of the described synthetic routes include Synthetic Examples 1 through 78. Compounds analogous to the target compounds of these examples can be, and in many cases, have been, made according to similar routes. The disclosed compounds are useful in basic research and as pharmaceutical agents as described in the next section.

Broadly, compounds of formula I may be made according to Scheme 1. Aldehyde (III) can be condensed with diamine (II) in the presence of an oxidizing agent such as $Na_2S_2O_5$ to provide benzimidazoles (I). This reaction takes place in a solvent, such as DMA or DMF, with the application of heat. Better yields might be obtained where the reaction is heated to a temperature of from 80° C. to 100° C. However in the case that Z is a carbonyl, better yields are obtained at a reaction temperature of 60° C. Compounds where Z contains an alcohol form a dimer in this reaction, which must be hydrolyzed in the presence of water and an acid at elevated temperatures. Improved yields for compounds where Z is an alcohol may be obtained as described below for Scheme 6.

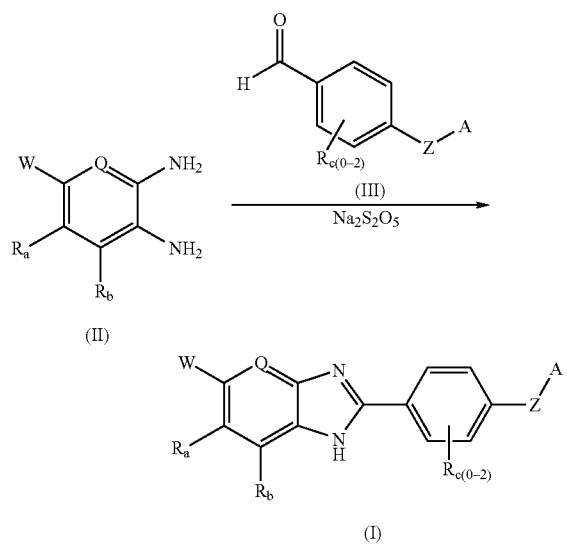

Schemes 2, 3, 4 and 5 show the formation of various aldehyde (III) subtypes. Referring to Scheme 2, a ketone (IV) may be protected to form, for example, a dioxolane. Lithium halogen exchange of the bromide with a suitable alkyllithium reagent such as n-BuLi, followed by a DMF quench will produce aldehyde (IIIa). Other protecting groups amenable to lithium halogen exchange chemistry may also be employed. In this regard, reference is made to "Protective Groups in Organic Synthesis", John Wiley & Sons, 1991. Deprotection of the ketone protecting group, in this case with a suitable acid such as perchloric acid, affords aldehyde (IIIb). Other functional groups in A or in $R_c$ that are sensitive to chemistry utilizing butyl lithium should be protected. For example, a carbonyl group should be protected as the ketal as described for Z.

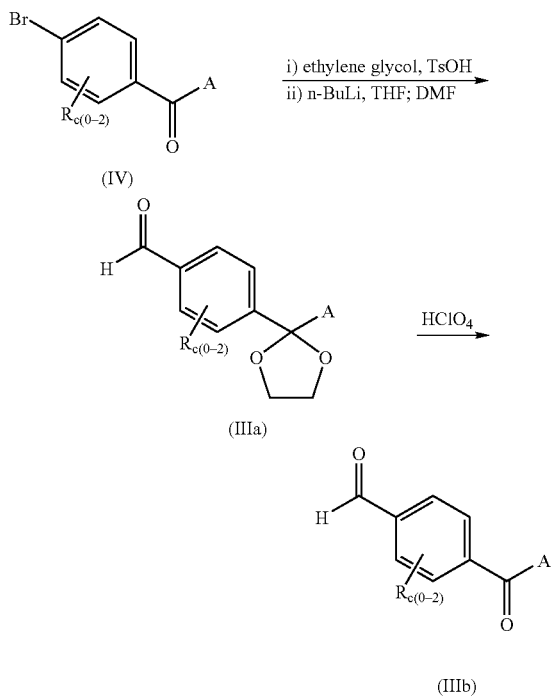

Referring to Scheme 3, anilines (V) may be halogenated in the para position by treatment with a brominating agent such as N-bromosuccinimide. Lithium halogen exchange as described above followed by a DMF quench can be used to produce aldehydes of type (IIIc). Groups in A or in $R_c$ that are sensitive to chemistry utilizing butyl lithium should be protected. For example, a carbonyl group should be protected as the ketal as described for Z. In one alternative to Scheme 3, a phenyl alkyl amine may be cross-coupled with 4-bromobenzaldehyde in the presence of a palladium catalyst to produce aldehyde (IIIc).

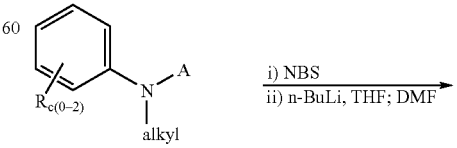

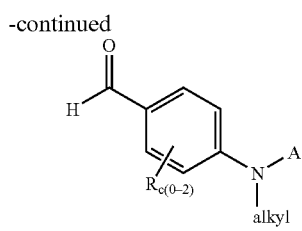

(IIIc)

Referring to Scheme 4, an aldehyde/ketone (VI) undergoes a Grignard reaction with an appropriate Grignard reagent (VII) that contains a masked aldehyde to produce bicyclic alcohol (VIII). Where $X_1$ is hydrogen, alcohol (VII) is oxidized and deprotected to the aldehyde (IIIb). Where there are groups in A or $R_c$ that are sensitive to oxidation, mild oxidation conditions should be employed such as TEMPO or PDC or an appropriate protecting group should be employed. Where $X_1$ is alkyl, alcohol (VII) is exposed to perchloric acid, allowing for deprotection of the aldehyde in addition to dehydration of the alcohol to form aldehyde (IIId). Hydrogenation of the double bond in compounds of formula (I) derived from (IIId) can lead to alternative embodiments of formula (I) in which Z is $>CR_dR_d$. Where there are groups in A or $R_c$ that are sensitive to oxidation, mild deprotection conditions should be employed conc. HCl in THF. Where $X_1$ is hydrogen, alcohol (VII) is exposed to a protic acid which deprotects to form aldehyde (IIIe). Where there are groups in A or $R_c$ that are sensitive to oxidizing conditions, non-oxidizing acids should be used for the deprotection such as HCl.

Referring to Scheme 5, substituted amine (X) is sulfonylated with a formylated benzene sulfonyl chloride derivative (IX) to produce aldehyde (IIIf). In the case that $X_1$, $R_c$ or A contains a primary alcohol then this alcohol should be protected with an acid sensitive protecting group, such as a silyl ether. The bicyclic A fused sulfonamides may be produced in Scheme 5 where the depicted cyclic substituted amine is replaced with an amine of the formula

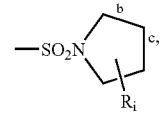

where A is fused at the a or b faces, or

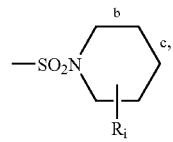

where A is fused at the a or b faces.

Scheme 4

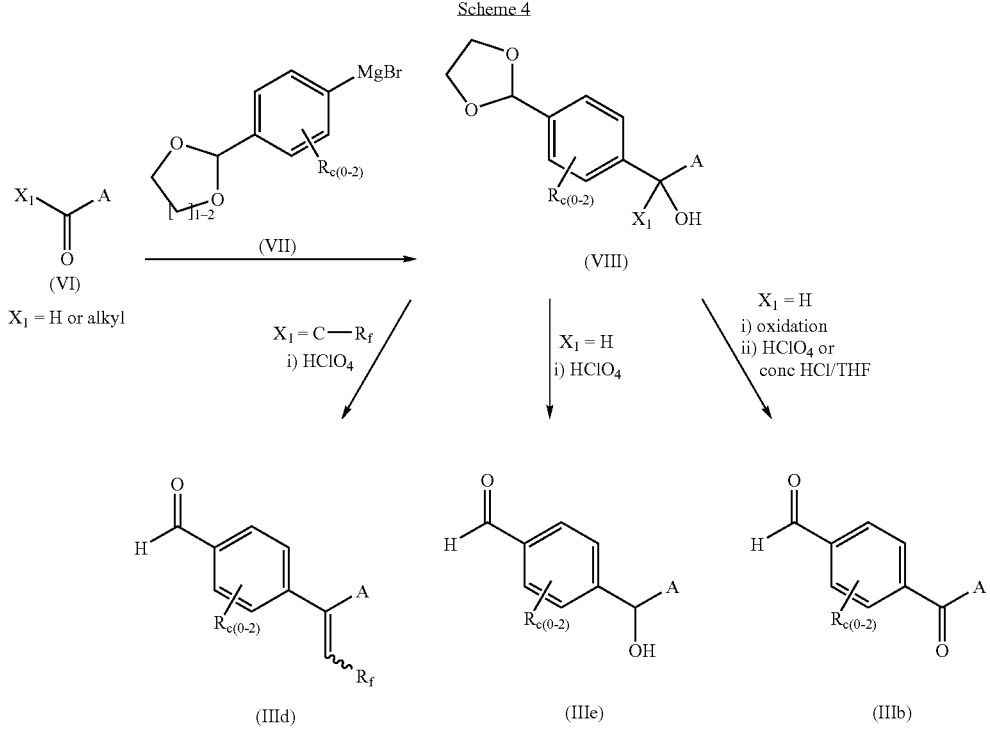

Scheme 5

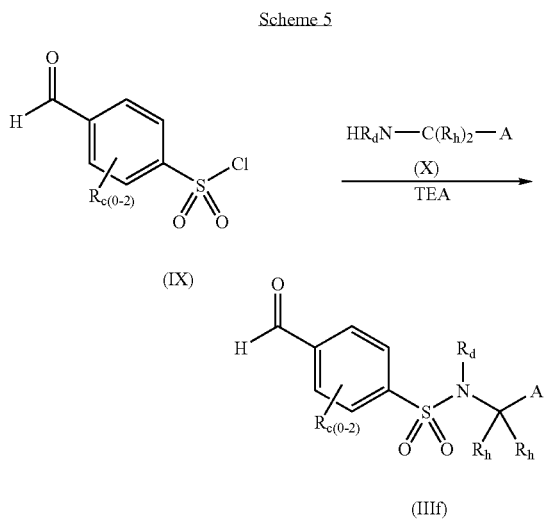

Referring to Scheme 6, compounds of formula (XIb) can be obtained by reducing compounds of formula (XIa) with NaBH$_4$, LiBH$_4$, Na(OAc)$_3$BH, DIBAL-H or other reducing agent. Compounds of formula (XIb) may be further reduced with reducing agents, including NaBH$_4$, triethylsilylhydride, TES-Cl or TMS-Cl to obtain compounds of formula (XIc). Compounds of formula (XIb) may be alkylated to form compounds of formula (XId) by various methods. In the depicted method, the alcohol is converted to a good leaving group, such as a chloride, using either HCl or SOCl$_2$, and the resulting benzyl chloride may be displaced with a variety of alcohols to produce the corresponding ether (XId). In another method, a base, such as NaH, is used with an alkylating agent, such as MeI, to form a methyl ether. The desired R$_e$ may be obtained with various alkylating agents. Compounds of formula (XIb) may be aminated to form compounds of formula (XIe) by first forming the chloride with chlorinating agents such as SOCl$_2$ or HCl and subsequently displacing the chloride with the appropriate amine.

Scheme 6

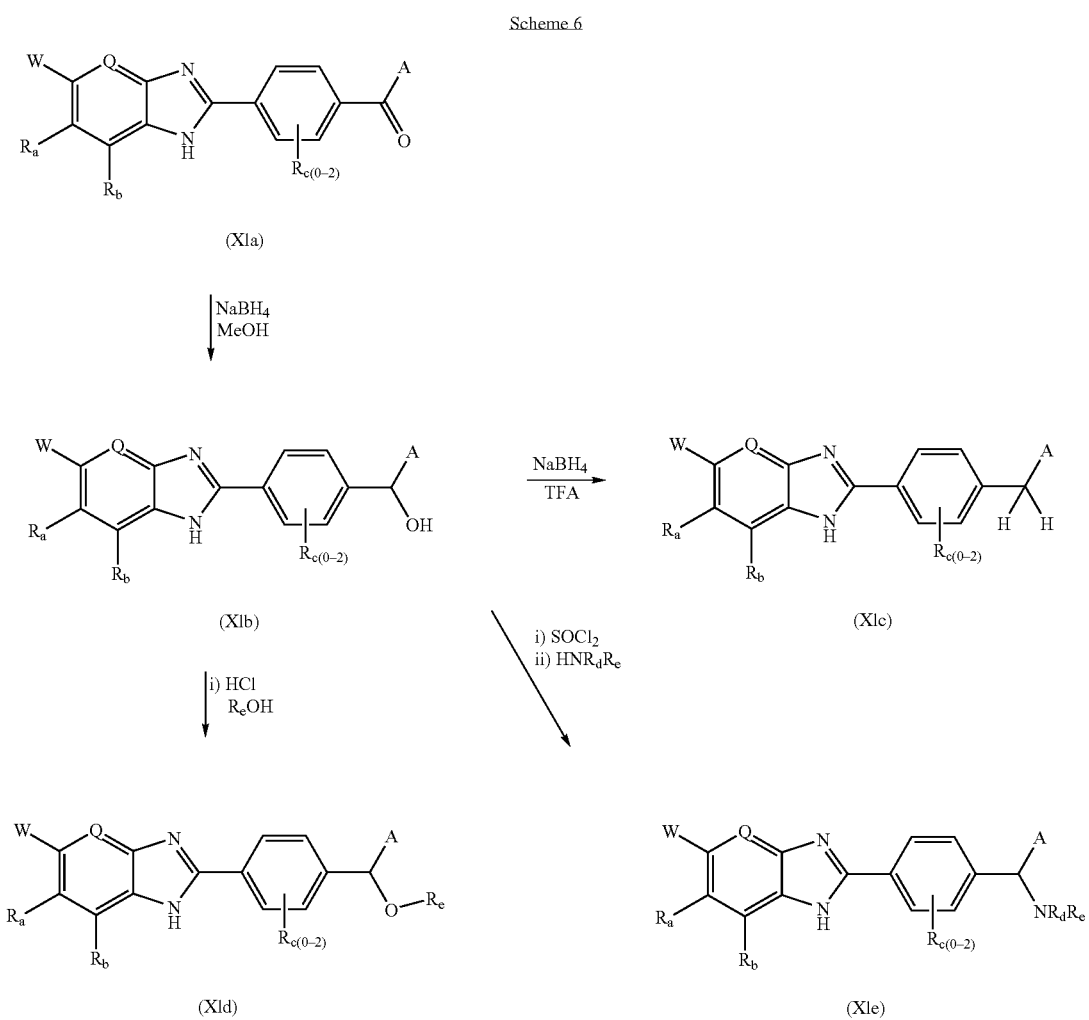

Referring to Scheme 7, compounds of formula (XIg) can be obtained by nucleophilic addition of an appropriate Grignard or lithium reagent to compound (XIa). The resulting tertiary alcohol may then be converted to ethers or amines of type (XIh) or (XIj) using the methods described in Scheme 6. Compounds of formula (XIg) can also be converted into analogs of formula (IIId) in Scheme 4 by treatment with perchloric acid. The resulting double bond can be hydrogenated to access alternative embodiments of formula (I) in which Z is >$CR_dR_d$.

$(NH_4)_2CO_3$ provides 2-aminopyridine (XV). Removal of the methyl group in (XV) with hydrobromic acid and acetic acid, followed by conversion to the bromide using a nucleophilic bromide source such as $(C_4H_9)_4N^+Br^-$, in the presence of $P_2O_5$, gives compound (XVI). Treatment of the bromide with a metallic cyanide such as CuCN then results in the formation of compound (XVII). Reduction of the nitro group of (XVII) using $H_2$ and Pd or other reducing agent, followed by condensation with an aryl aldehyde of type (III) in the presence of an oxidizing agent such as $Na_2S_2O_5$

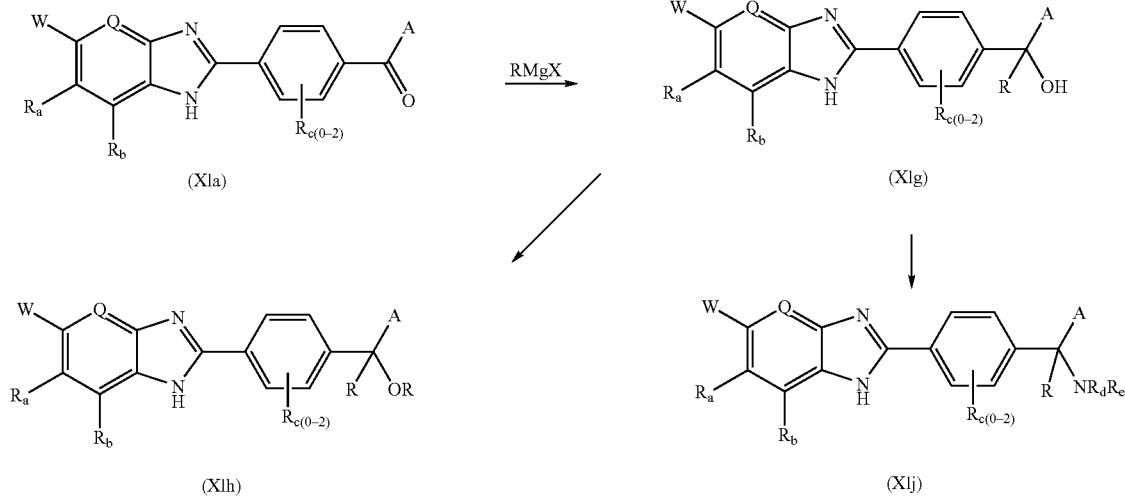

Referring to Scheme 8, the carboxylic acid of formula (XII) can be converted to an amide by treatment with 1,1'-carbonyldiimidazole (CDI), or other similar activating agent, followed by a nucleophilic amine to provide compounds of formula (XIII). Standard peptide coupling conditions known to one skilled in the art are also applicable.

provides imidazopyridines of general formula (XVIII). The cyano group of (XVIII) can then be converted to an amide of formula (XIX) by hydrolysis with $BF_3$ in acetic acid.

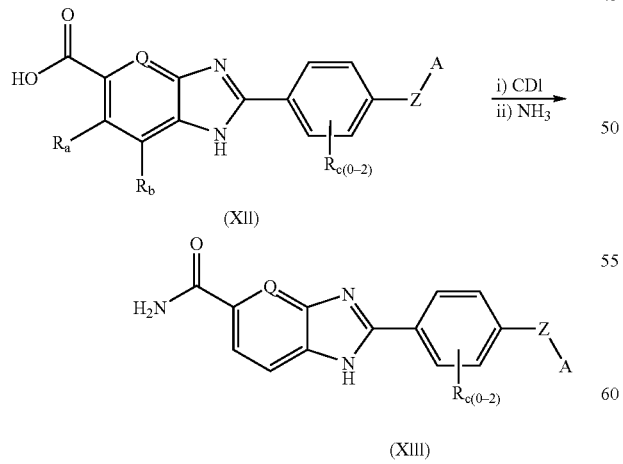

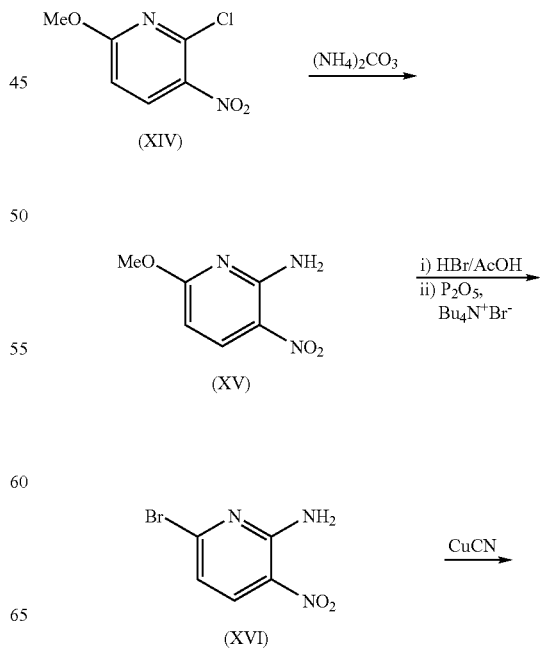

Compounds of general formula (XIX) can be synthesized using the methods outlined in Scheme 9. Treatment of pyridine (XIV) with an ammonium equivalent such as

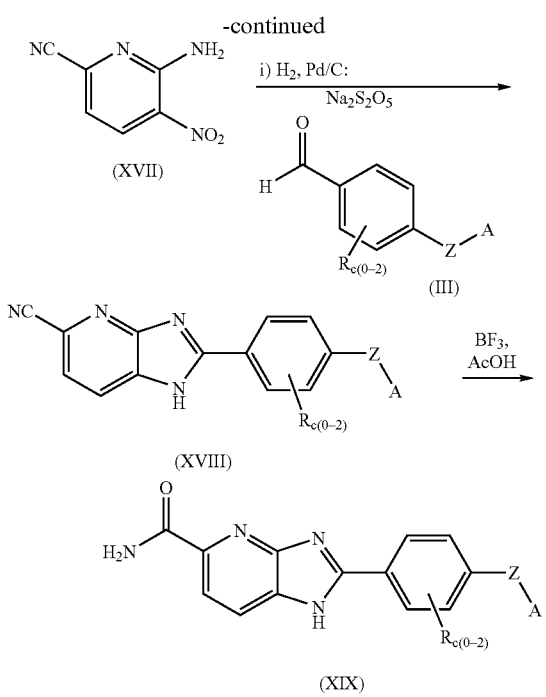

D. Formulation and Administration

The present compounds inhibit the checkpoint modulator Cds1 and therefore are useful as a medicine especially in methods for treating patients suffering from disorders or conditions that are modulated or regulated by Cds1, such as cancer.

The invention features a method for treating a subject with cancer, said method comprising administering to the subject a therapeutically effective amount of a pharmaceutical composition comprising a compound of the invention. The invention also provides a method for inhibiting Cds1 activity in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration, intravenous injection or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salt forms that the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates that the disclosed compounds, as well as the salts thereof, are able to form. Such solvates are for example hydrates, alcoholates and the like. Conversely the salt form can be converted by treatment with alkali into the free base form.

"Stereoisomeric forms" defines all the possible isomeric forms that the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention. For example, the present invention includes

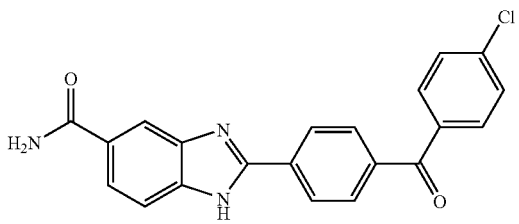

2-[4-(4-Chloro-benzoyl]-1H-benzoimidazole-5-carboxylic acid amide as well as

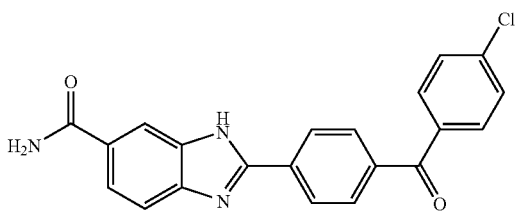

2-[4-(4-Chloro-benzoyl]-3H-benzoimidazole-5-carboxylic acid amide.

Those of skill in the treatment of disorders or conditions mediated by the Cds1 enzyme could easily determine the effective daily amount from the test results presented hereinafter and other information. In general it is contemplated that a therapeutically effective dose would be from 0.001 mg/kg to 100 mg/kg body weight, more preferably from 1 mg/kg to 50 mg/kg body weight. It may be appropriate to administer the therapeutically effective dose as two, three, four or more sub-doses at appropriate intervals throughout the day. Said sub-doses may be formulated as unit dosage forms, for example, containing 1 mg to 2000 mg, and in particular 10 to 500 mg of active ingredient per unit dosage form. Examples include 10 mg, 25 mg, 50 mg, 100 mg, 150 mg, 250 mg, and 500 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds.

E. EXAMPLES

General Experimental:

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Mass spectra were obtained on an Agilent series 1100 MSD using electrospray ionization (ESI) in either positive or negative mode as indicated.

HPLC retention times are reported in minutes, using the methods and conditions reported below.

| Method A: | |
|---|---|
| Instrument: | Agilent HP-1100 |
| Solvent: | Acetonitrile (0.05% trifluoroacetic acid, TFA)/ $H_2O$ (0.05% TFA) |
| Flow rate: | 0.75 mL/min |
| Gradient: | 1 min at 1% $H_2O$; 7 min linear ramp to 99% $H_2O$; 4 min at 99% $H_2O$. |
| Column: | ZORBAX Eclipse XDB-C8 (5 um, 4.6 × 150 mm) |
| Temperature: | 35° C. |
| Wavelength: | Duel detection at 220 and 254 nM. |
| Method B: | |
| Instrument: | Agilent HP-1100 |
| Solvent: | Acetonitrile (0.05% trifluoroacetic acid, TFA)/ $H_2O$ (0.05% TFA) |
| Flow rate: | 1.5 mL/min |
| Gradient: | 1 min at 1% $H_2O$; 3.5 min linear ramp to 99% $H_2O$; 1.5 min at 99% $H_2O$ |
| Column: | XTerra® RP$_{18}$ (4.6 × 50 mm) |
| Temperature: | 35° C. |
| Wavelength: | Duel detection at 220 and 254 nM. |
| Method C: | |
| Instrument: | Agilent HP-1100 |
| Solvent: | Acetonitrile (0.05% TFA)/$H_2O$ (0.05% TFA) |
| Flow rate: | 1.0 mL/min |
| Gradient: | 10% Acetonitrile; 5 min linear ramp to 100% Acetonitrile; 5 min at 100% Acetonitrile. |
| Column: | Phenomenex Luna® C18 (5 um, 4.6 × 150 mm) |
| Temperature: | 24° C. |
| Wavelength: | Detection at 230, 254 and 280 nM. |

Example 1

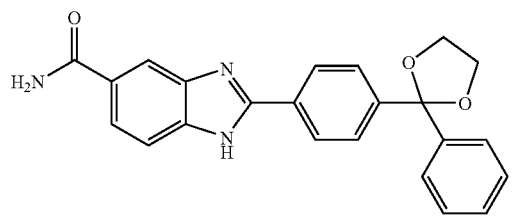

2-[4-(2-Phenyl-[1,3]dioxolan-2-yl)-phenyl]-1H-benzoimidazole-5-carboxylic acid amide A. 2-(4-Bromo-phenyl)-2-phenyl-[1,3]dioxolane. To a solution of (4-bromo-phenyl)-phenyl-methanone (5.0 g, 19.1 mmol) in anhydrous toluene under $N_2$ was added ethylene glycol (5.32 mL, 95.5 mmol). The reaction mixture was heated to reflux for 10 h under a Dean-Stark trap. The mixture was cooled to room temperature (RT), washed with 1 N sodium hydroxide (100 mL) and $H_2O$ (100 mL), and dried (MgSO$_4$). Solvent was removed under reduced pressure, yielding the title compound as a solid (2.89 g, 49%).

B. 4-(2-Phenyl-[1,3]dioxolan-2-yl)-benzaldehyde. To a solution of 2-(4-bromo-phenyl)-2-phenyl-[1,3]dioxolane (500 mg, 1.6 mmol) cooled to −78° C. in anhydrous tetrahydrofuran (THF) (100 mL) under $N_2$ was added n-butyllithium (1.1 mL of 1.6 M in hexanes, 1.7 mmol) dropwise. The reaction mixture was stirred at −78° C. for 30 min, then dimethylformamide (DMF) (0.135 mL, 1.7 mmol) was added dropwise, and the mixture was allowed to warm to RT. The mixture was poured into saturated aqueous $NH_4Cl$, and the resulting mixture was extracted with diethyl ether ($Et_2O$) (2×100 mL). The combined extracts were washed with brine (100 mL) and dried ($Na_2SO_4$). The solvent was removed under reduced pressure. The title compound was obtained as an oil (350 mg, 84%). $^1$H NMR (400 MHz, $CDCl_3$): δ 9.99 (s, 1H), 7.84 (d, J=8.5 Hz, 2H), 7.71 (d, J=8.2 Hz, 2H), 7.52–7.49 (dd, J=8.4, 1.5 Hz, 2H), 7.36–7.29 (m, 4H), 4.12–4.04 (m, 4H).

C. 2-[4-(2-Phenyl-[1,3]dioxolan-2-yl)-phenyl]-1H-benzoimidazole-5-carboxylic acid amide. To a solution of 3,4-diamino-benzamide (100 mg, 0.6 mmol) in anhydrous DMF was added 4-(2-phenyl-[1,3]dioxolan-2-yl)-benzaldehyde (168 mg, 0.6 mmol) and sodium metabisulfite (164 mg, 0.86 mmol). The mixture was heated to 90° C. under $N_2$ for 16 h. The reaction mixture was cooled and added dropwise to ice/$H_2O$. The resulting solids were filtered and washed with $H_2O$ (50 mL) then hexanes (2×50 mL). Purification by chromatography (silica gel, 1% methanol saturated with ammonia/9% methanol/$CH_2Cl_2$) afforded 160 mg (63%) of the title compound. TLC (silica, 1% methanol saturated with ammonia/9% methanol/$CH_2Cl_2$): $R_f$=0.3. HPLC (Method A): $R_t$=7.02. MS (ESI+): mass calculated for $C_{23}H_{19}N_3O_3$, 385.1; m/z found, 386.1 [M+H]$^+$. $^1$H NMR (400 MHz, $CD_3OD$): δ 8.13 (br s, 1H), 8.04 (d, J=8.4 Hz, 2H), 7.77 (d, J=8.5 Hz, 1H), 7.64 (d, J=8.4 Hz, 2H), 7.58 (br s, 1H), 7.49–7.47 (dd, J=8.4. 1.5 Hz, 2H), 7.32–7.23 (m, 3H), 4.03 (s, 4H).

Example 2

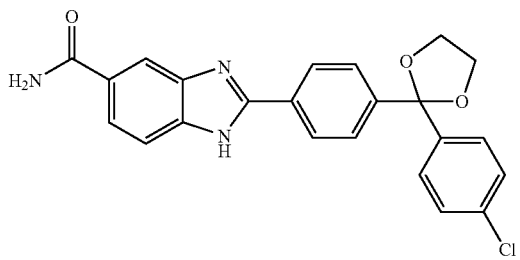

2-{4-[2-(4-Chloro-phenyl)-[1,3]dioxolan-2-yl]-phenyl}-1H-benzoimidazole-5-carboxylic acid amide A. 2-(4-Bromo-phenyl)-2-(4'-chloro-phenyl)-[1,3]dioxolane. This compound was prepared as described in Example 1 substituting (4-bromo-phenyl)-(4-chloro-phenyl)-methanone (750 mg, 2.5 mmol) for (4-bromo-phenyl)-phenyl-methanone in Step A. The title compound was recrystallized from ethanol to afford 680 mg (85%) of white plates. $^1$H NMR (400 MHz, $CDCl_3$): δ 7.45 (d, J=8.7 Hz, 2H), 7.41 (d, J=8.7 Hz, 2H), 7.35 (d, J=8.7 Hz, 2H), 7.29 (d, J=8.7 Hz, 2H), 4.04 (m, 4H).

B. 4-[2-(4-Chloro-phenyl)-[1,3]dioxolan-2-yl]-benzaldehyde. This compound was prepared as described in Example 1 substituting 2-(4-bromo-phenyl)-2-(4-chloro-phenyl)-[1,3]dioxolane (300 mg, 0.8 mmol) for 2-(4-bromo-phenyl)-2-phenyl-[1,3]dioxolane in Step B. Purification by chromatography (silica gel, $CH_2Cl_2$) afforded 100 mg (39%) of the title compound. $^1$H NMR (400 MHz, $CDCl_3$): δ 10.00 (s, 1H), 7.85 (d, J=8.4 Hz, 2H), 7.67 (d, J=8.3 Hz, 2H), 7.45 (d, J=8.6 Hz, 2H), 7.30 (d, J=8.6 Hz, 2H), 4.07 (m, 4H).

C. 2-{4-[2-(4-Chloro-phenyl)-[1,3]dioxolan-2-yl]-phenyl}-1H-benzoimidazole-5-carboxylic acid. This compound was prepared as described in Example 1 Step C from 4-[2-(4-chloro-phenyl)-[1,3]dioxolan-2-yl]-benzaldehyde (100 mg, 0.34 mmol) and 3,4-diamino-benzoic acid (53 mg, 0.34 mmol). The title compound was obtained as a tan solid 135 mg (92%). MS (ESI): mass calculated for $C_{23}H_{17}ClN_2O_4$, 420.1; m/z found, 421.1 [M+H]$^+$, 419.1 [M−H]$^−$. HPLC (Method B): $R_t$=2.43.

D. 2-[4-(2-Phenyl-[1,3]dioxolan-2-yl)-phenyl]-1H-benzoimidazole-5-carboxylic acid amide. To a solution of 2-{4-[2-(4-chloro-phenyl)-[1,3]dioxolan-2-yl]-phenyl}-1H-benzoimidazole-5-carboxylic acid (135 mg, 0.32 mmol) in anhydrous DMF was added carbonyldiimidazole (118 mg, 0.73 mmol). The reaction mixture was stirred under $N_2$ for 30 min and then cooled to 0° C., and ammonium bicarbonate (140 mg, 1.4 mmol) was added. The resulting mixture was allowed to warm to RT and was stirred for 16 h. The mixture was added dropwise to saturated aqueous $NH_4Cl$. The resulting precipitate was collected by filtration and washed with $H_2O$ (100 mL) then hexanes (100 mL). The product was dried under vacuum overnight to give the title compound (102 mg, 76%). TLC (silica, 1% methanol saturated with ammonia/9% methanol/$CH_2Cl_2$): $R_f$=0.33. HPLC (Method A): $R_t$=7.42. MS (ESI+): mass calculated for $C_{23}H_{18}ClN_3O_3$, 419.1; m/z found, 420.1 [M+H]$^+$. $^1$H NMR (400 MHz, $CD_3OD$): δ 8.09 (s, 1H), 8.00 (d, J=8.4 Hz, 2H), 7.75–7.72 (dd, J=8.5, 1.5 Hz, 1H), 7.59 (d, J=8.4 Hz, 2H), 7.56 (br d, J=8.7 Hz, 1H), 7.43 (d, J=8.5 Hz, 2H), 7.27 (d, J=8.6 Hz, 2H), 3.99 (s, 4H).

Example 3

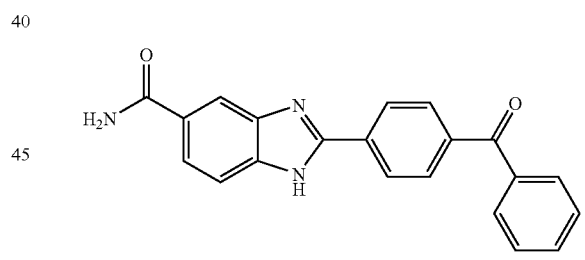

2-(4-Benzoyl-phenyl)-1H-benzoimidazole-5-carboxylic acid amide

A. 4-Benzoyl-benzaldehyde. To a cooled (ice/acetone) solution of 4-(2-phenyl-[1,3]dioxolan-2-yl)-benzaldehyde (145 mg, 0.57 mmol) in $CH_2Cl_2$ was added dropwise perchloric acid (70%, 0.38 mL). The reaction mixture was stirred at RT for 2 h, and then was poured into saturated aqueous $NaHCO_3$ (75 mL). The aqueous layer was extracted with $CH_2Cl_2$. The combined organic layers were washed with $H_2O$ (2×50 mL) and dried ($Na_2SO_4$). The solvent was removed under reduced pressure to provide 100 mg (83%) of the title compound. $^1$H NMR (400 MHz, $CDCl_3$): δ 10.14 (s, 1H), 8.01 (d, J=8.4 Hz, 2H), 7.93 (d, J=8.2 Hz, 2H), 7.83–7.80 (dd, J=8.4, 1.3 Hz, 2H), 7.63 (d, J=7.4 Hz, 1H), 7.52 (t, J=7.6 Hz, 2H).

B. 2-(4-Benzoyl-phenyl)-1H-benzoimidazole-5-carboxylic acid. This compound was prepared as described in Example 1 using 4-benzoyl-benzaldehyde (100 mg, 0.47 mmol) and 3,4-diamino-benzoic acid (72 mg, 0.47 mmol) in Step C. The title compound was obtained as a tan solid (135 mg, 85%). MS (ESI): mass calculated for $C_{21}H_{14}N_2O_3$, 342.1; m/z found, 342.9 $[M+H]^+$. HPLC (Method A): $R_t$=7.17.

C. 2-(4-Benzoyl-phenyl)-1H-benzoimidazole-5-carboxylic acid amide. This compound was prepared as described in Example 2 using 2-(4-benzoyl-phenyl)-1H-benzoimidazole-5-carboxylic acid (138 mg. 0.4 mmol) in Step D. The title compound was obtained as a tan solid (54 mg, 39%). TLC (silica, 1% methanol saturated with ammonia/9% methanol/$CH_2Cl_2$): $R_f$=0.31. HPLC (Method A): $R_t$=6.75. MS (ESI+): mass calculated for $C_{21}H_{15}N_3O_2$, 341.1; m/z found, 342.1 $[M+H]^+$. $^1$H NMR (400 MHz, $CD_3OD$): δ 8.19 (d, J=8.2 Hz, 2H), 8.16 (br s, 1H), 7.87 (d, J=8.3 Hz, 2H), 7.80–7.78 (dd, J=8.5, 1.6 Hz, 1H), 7.76 (d, J=8.4 Hz, 2H), 7.62–7.60 (m, 2H), 7.49 (t, J=7.5 Hz, 2H), 7.00 (s, 1H).

Example 4

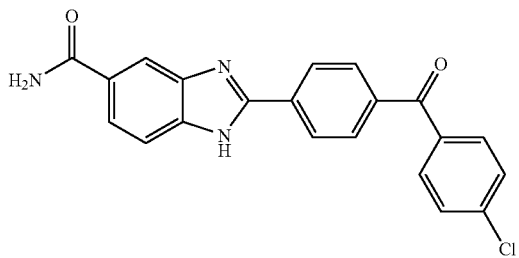

2-[4-(4-Chloro-benzoyl)-phenyl]-1H-benzoimidazole-5-carboxylic acid amide

A. (4-Chloro-phenyl)-(4-[1,3]dioxolan-2-yl-phenyl)-methanol. To a solution of 4-chloro-benzaldehyde (1.98 g, 14.0 mmol) in anhydrous THF, cooled to –78° C., was added 4-(1,3-dioxolan-2-yl)phenylmagnesium bromide (60 mL, 0.25 M in THF) dropwise. The reaction mixture was stirred 1 h at –78° C. then quenched with saturated aqueous $NH_4Cl$ (50 mL). The resulting mixture was extracted with $Et_2O$ (2×100 mL). The combined extracts were washed with $H_2O$ (100 mL) then brine (100 mL), and dried ($MgSO_4$). Solvent was removed under reduced pressure, and the residue was purified by chromatography (silica gel, 50% ethyl acetate/hexanes) to afford the title compound (3.25 g, 79%). TLC (silica, 50% ethyl acetate/hexanes): $R_f$=0.4. $^1$H NMR (500 MHz, $CDCl_3$): δ 7.45 (d, J=8.2 Hz, 2H), 7.36 (d, J=8.1 Hz, 2H), 7.29 (s, 4H), 5.82 (d, J=3.3 Hz, 1H), 4.14–4.08 (m, 2H), 4.06–4.01 (m, 2H).

B. (4-Chloro-phenyl)-(4-[1,3]dioxolan-2-yl-phenyl)-methanone. (4-Chloro-phenyl)-(4-[1,3]dioxolan-2-yl-phenyl)-methanol (250 mg, 0.85mmol) was dissolved in ethyl acetate (1.5 mL) and treated with a solution of sodium bromide (88 mg, 0.85 mmol) in saturated aqueous $NaHCO_3$ (2.3 mL). The reaction mixture was cooled to 0° C. and stirred for 30 min. Free radical 2,2,6,6-tetramethyl-1-piperidinyloxy (TEMPO) (1.3 mg, 0.008 mmol) and then aqueous sodium hypochlorite solution (1.25 mL, 0.67 M) were added, and the resulting mixture was stirred for 2 h. Ethyl acetate (100 mL) and brine (100 mL) were added, and the mixture was stirred 5 min. The organic layer was washed with brine (2×75 mL) and then dried ($Na_2SO_4$). Solvent was removed under reduced pressure yielding the title compound as an off-white solid (247 mg, 99%). TLC (silica, 50% ethyl acetate/hexanes): $R_f$=0.5. HPLC (Method A): $R_t$=9.99. MS (ESI+): mass calculated for $C_{16}H_{13}ClO_3$, 288.0; m/z found, 289.0 $[M+H]^+$. $^1$H NMR (500 MHz, $CDCl_3$): δ 7.78 (d, J=8.3 Hz, 2H), 7.75 (d, J=8.6 Hz, 2H), 7.61(d, J=8.1 Hz, 2H), 7.46 (d, J=8.6 Hz, 1H), 5.89 (s, 1H), 4.16–4.12 (m, 2H), 4.11–4.06 (m, 2H).

C. 4-(4-Chloro-benzoyl)-benzaldehyde. This compound was prepared as described in Example 3 using (4-chloro-phenyl)-(4-[1,3]dioxolan-2-yl-phenyl)-5 methanone in Step A. TLC (silica, 50% ethyl acetate/hexanes): $R_f$=0.6. HPLC (Method A): $R_t$=9.93. MS (ESI+): mass calculated for $C_{14}H_9ClO_2$, 244.0; m/z found, 245.0 $[M+H]^+$. $^1$H NMR (500 MHz, $CDCl_3$): δ 10.13 (s, 1H), 8.01 (d, J=8.4 Hz, 2H), 7.90 (d, J=8.2 Hz, 2H), 7.76 (d, J=8.6 Hz, 2H), 7.49 (d, J=8.6 Hz, 2H).

D. 2-[4-(4-Chloro-benzoyl)-phenyl]-1H-benzoimidazole-5-carboxylic acid amide. To a solution of 3,4-diamino-benzamide (92 mg, 0.6 mmol) in anhydrous dimethylacetamide (DMA) (10 mL) was added 4-(4-chloro-benzoyl)-benzaldehyde (150 mg, 0.6 mmol) and sodium metabisulfite (151 mg, 0.79 mmol). The mixture was heated to 60° C. under $N_2$ for 16 h. The reaction mixture was cooled and added dropwise to ice/$H_2O$. The resulting solids were filtered and washed with $H_2O$ (50 mL) then hexanes (2×50 mL). Purification by chromatography (silica gel, 1% methanol saturated with ammonia/9% methanol/$CH_2Cl_2$) afforded 71 mg (31%) of the title compound. TLC (silica, 1% methanol saturated with ammonia/9% methanol/$CH_2C_2$): $R_f$=0.3. HPLC (Method A): $R_t$=7.53. MS (ESI+): mass calculated for $C_{21}H_{14}ClN_3O_2$, 375.1; m/z found, 376.0, $[M+H]^+$. $^1$H NMR (500 MHz, DMSO-$d_6$): δ 13.35 (br s, 1H), 8.38 (d, J=8.3 Hz, 2H), 8.01 (br s, 1H), 7.94 (d, J=8.3 Hz, 2H), 7.82 (d, J=8.4 Hz, 3H), 7.67 (d, J=8.4 Hz, 3H), 7.30 (br s, 1H).

Example 5

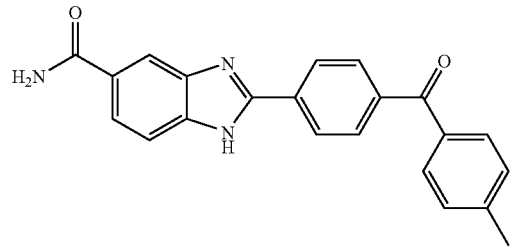

2-[4-(4-Methyl-benzoyl)-phenyl]-1H-benzoimidazole-5-carboxylic acid amide

The title compound was prepared as described in Example 4 substituting 4-methyl-benzaldehyde for 4-chloro-benzaldehyde in Step A. TLC (silica, 1% methanol saturated with ammonia/9% methanol/$CH_2Cl_2$): $R_f$=0.29. HPLC (Method A): $R_t$=7.36. MS (ESI+): mass calculated for $C_{22}H_{17}N_3O_2$, 355.1; m/z found, 356.1 $[M+H]^+$. $^1$H NMR (500 MHz, $CD_3OD$): δ 8.26 (d, J=8.5 Hz, 2H), 8.25 (br s, 1H), 7.93 (d, J=8.5 Hz, 2H), 7.85 (d, J=8.4 Hz, 1H), 7.74 (d, J=8.2 Hz, 2H), 7.69 (br s, 1H), 7.38 (d, J=7.8 Hz, 2H), 2.46 (s, 3H).

Example 6

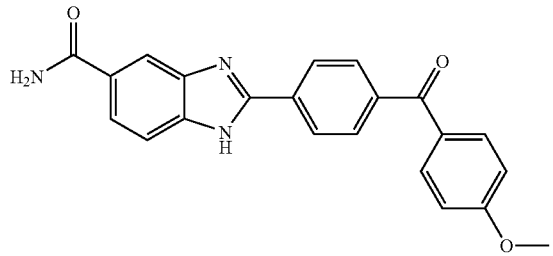

2-[4-(4-Methoxy-benzoyl)-phenyl]-1H-benzoimidazole-5-carboxylic acid amide

The title compound was prepared as described in Example 4 substituting 4-methoxy-benzaldehyde for 4-chloro-benzaldehyde in Step A. TLC (silica, 1% methanol saturated with ammonia/9% methanol/CH$_2$Cl$_2$): R$_f$=0.27. HPLC (Method A): R$_t$=7.09. MS (ESI+): mass calculated for C$_{22}$H$_{17}$N$_3$O$_3$, 371.1; m/z found, 372.1 [M+H]$^+$. $^1$H NMR (500 MHz, CD$_3$OD): δ 8.25 (d, J=8.4 Hz, 3H), 7.89 (d, J=8.4 Hz, 2H), 7.84 (d, J=8.9 Hz, 3H), 7.68 (br s, 1H), 7.07 (d, J=8.9 Hz, 2H), 3.90 (s, 3H).

Example 7

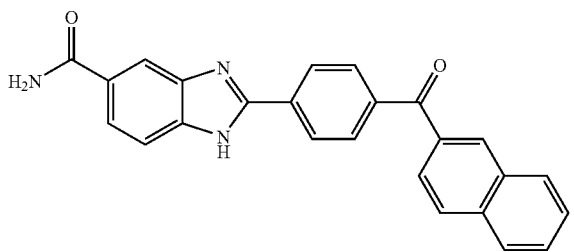

2-[4-(Naphthalene-2-carbonyl)-phenyl]-1H-benzoimidazole-5-carboxylic acid amide

The title compound was prepared as described in Example 4 substituting naphthalene-2-carbaldehyde for 4-chloro-benzaldehyde in Step A. TLC (silica, 1% methanol saturated with ammonia/9% methanol/CH$_2$Cl$_2$): R$_f$=0.25. HPLC (Method A): R$_t$=7.74. MS (ESI+): mass calculated for C$_{25}$H$_{17}$N$_3$O$_2$, 391.1; m/z found, 392.1 [M+H]$^+$. $^1$H NMR (500 MHz, CD$_3$OD): δ 8.30 (s, 1H), 8.27 (d, J=8.4 Hz, 2H), 8.23 (br s, 1H), 8.02–7.95 (m, 5H), 7.92–7.90 (dd, J=8.5, 1.6 Hz, 1H), 7.85 (br d, J=7.8 Hz, 1H), 7.68 (br s, 1H), 7.66–7.62 (td, J=7.5, 1.1 Hz, 1H), 7.59–7.56 (td, J=7.5, 1.1 Hz, 1H).

Example 8

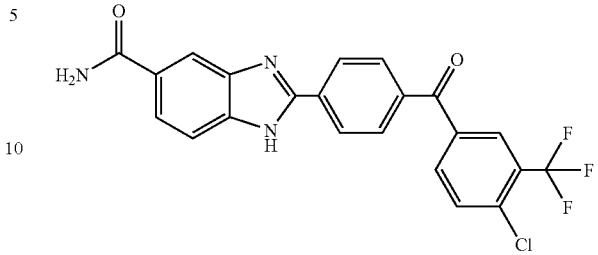

2-[4-(4-Chloro-3-trifluoromethyl-benzoyl)-phenyl]-1H-benzoimidazole-5-carboxylic acid amide The title compound was prepared as described in Example 4 substituting 4-chloro-3-trifluoromethyl-benzaldehyde for 4-chloro-benzaldehyde in Step A. TLC (silica, 1% methanol saturated with ammonia/9% methanol/CH$_2$Cl$_2$): R$_f$=0.25. HPLC (Method A): R$_t$=8.20. MS (ESI–): mass calculated for C$_{22}$H$_{13}$ClF$_3$N$_3$O$_2$, 443.1; m/z found, 442.5 [M–H]$^-$. $^1$H NMR (500 MHz, CD$_3$OD): δ 8.30 (d, J=8.5 Hz, 2H), 8.23 (br s, 1H), 8.20 (d, J=1.9 Hz, 1H), 8.05–8.03 (dd, J=8.2, 2.0 Hz, 1H), 7.99 (d, J=8.6 Hz, 2H), 7.86 (br d, J=8.3 Hz, 1H), 7.83 (d, J=8.3 Hz, 1H), 7.69 (br s, 1H).

Example 9

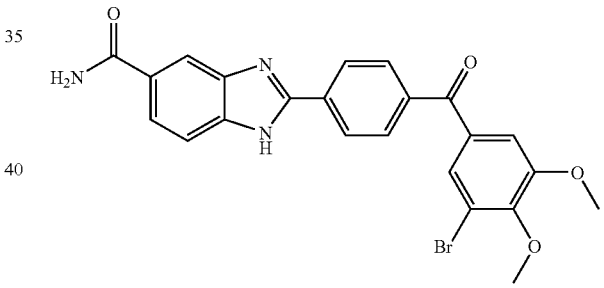

2-[4-(3-Bromo-4,5-dimethoxy-benzoyl)-phenyl]-1H-benzoimidazole-5-carboxylic acid amide A. (3,4-Dimethoxy-phenyl)-(4-[1,3]dioxolan-2-yl-phenyl)-methanol. This compound was prepared as described in Example 4 substituting 3,4-dimethoxy-benzaldehyde for 4-chloro-benzaldehyde in Step A. HPLC (Method A): R$_t$=8.01. $^1$H NMR (500 MHz, CDCl$_3$): δ 7.46 (d, J=8.2 Hz, 2H), 7.40 (d, J=8.1 Hz, 2H), 6.90 (d, J=1.9 Hz, 1H), 6.87–6.85 (dd, J=8.3, 1.9 Hz, 1H), 6.81 (d, J=8.2 Hz, 1H), 5.81 (d, J=3.5 Hz, 1H), 5.80 (s, 1H), 4.13–4.09 (m, 2H), 4.06–4.01 (m, 2H), 3.86 (s, 3H), 3.84 (s, 3H), 2.17–2.04 (m, 1H).

B. (3-Bromo-4,5-dimethoxy-phenyl)-(4-[1,3]dioxolan-2-yl-phenyl)-methanone. To a solution of (3,4-dimethoxy-phenyl)-(4-[1,3]dioxolan-2-yl-phenyl)-methanol (600 mg, 1.8 mmol) in ethyl acetate (5.0 mL) was added a solution of sodium bromide (253 mg, 2.4 mmol) in saturated aqueous NaHCO$_3$ (5.25 mL). The reaction mixture was cooled to 0° C. TEMPO (3.0 mg, 0.018 mmol) and then aqueous sodium hypochlorite solution (2.9 mL, 0.67 M) were added, and the resulting mixture was stirred for 2 h. Ethyl acetate (100 mL) and brine (100 mL) were added, and the mixture was stirred 5 min. The organic layer was washed with brine (2×75 mL) and then dried (Na$_2$SO$_4$). The solvent was removed under reduced pressure. Purification by chromatography (silica gel, 50% ethyl acetate/hexanes) afforded 312 mg (42%) of the title compound. MS (ESI+): mass calculated for C$_{18}$H$_{17}$BrO$_5$, 392.0; m/z found, 394.0 [M+H]$^+$. $^1$H NMR (500 MHz, CDCl$_3$): δ 7.83 (d, J=8.3 Hz, 2H), 7.58 (d, J=8.3 Hz, 2H), 7.08 (s, 1H), 6.87 (s, 1H), 5.86 (s, 1H), 4.16–4.10 (m, 2H), 4.09–4.03 (m, 2H), 3.94 (s, 3H), 3.84 (s, 3H).

C. 4-(3-Bromo-4,5-dimethoxy-benzoyl)-benzaldehyde. This compound was prepared as described in Example 3 substituting (3-bromo-4,5-dimethoxy-phenyl)-(4-[1,3]dioxolan-2-yl-phenyl)-methanone (300 mg, 0.7 mmol) for 4-(2-phenyl-[1,3]dioxolan-2-yl)-benzaldehyde in Step A. Purification by chromatography (silica gel, 50% ethyl acetate/hexanes) afforded 210 mg (79%) of the title compound. TLC (silica, 50% ethyl acetate/hexanes): R$_f$=0.47. $^1$H NMR (500 MHz, CDCl$_3$): δ 10.12 (s, 1H), 8.01–7.91 (m, 4H), 7.09 (s, 1H), 6.94 (s, 1H), 3.95 (s, 3H), 3.87 (s, 3H).

D. 2-[4-(3-Bromo-4,5-dimethoxy-benzoyl)-phenyl]-1H-benzoimidazole-5-carboxylic acid amide. This compound was prepared as described in Example 4 substituting 4-(3-bromo-4,5-dimethoxy-benzoyl)-benzaldehyde (210 mg, 0.5 mmol) for 4-(4-chloro-benzoyl)-benzaldehyde in Step D. Purification by chromatography (silica gel, 1% methanol saturated with ammonia/9% methanol/CH$_2$Cl$_2$) afforded 236 mg (53%) of the title compound. TLC (silica, 1% methanol saturated with ammonia/9% methanol/CH$_2$Cl$_2$): R$_f$=0.45. HPLC (Method A): R$_t$=7.45. MS (ESI+): mass calculated for C$_{23}$H$_{18}$BrN$_3$O$_4$, 479.0; m/z found, 480.0/482.0 [M+H]$^+$. $^1$H NMR (500 MHz, CD$_3$OD): δ 8.21 (br s, 1H), 8.20 (d, J=8.5 Hz, 2H), 7.91 (d, J=8.5 Hz, 2H), 7.84–7.82 (dd, J=8.5, 1.7 Hz, 1H), 7.65 (d, J=8.3 Hz, 1H), 7.21 (s, 1H), 7.04 (s, 1H), 3.90 (s, 3H), 3.82 (s, 3H).

Example 10

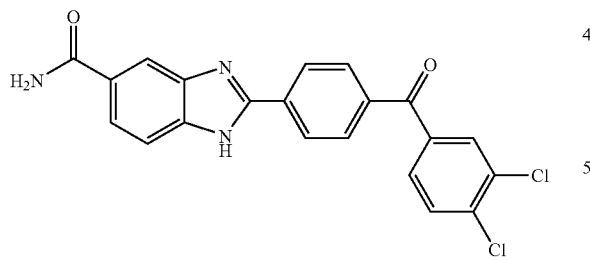

2-[4-(3,4-Dichloro-benzoyl)-phenyl]-1H-benzoimidazole-5-carboxylic acid amide

The title compound was prepared as described in Example 4 substituting 3,4-dichloro-benzaldehyde for 4-chloro-benzaldehyde in Step A. TLC (silica, 1% methanol saturated with ammonia/9% methanol/CH$_2$Cl$_2$): R$_f$=0.32. MS (ESI+): mass calculated for C$_{21}$H$_{13}$Cl$_2$N$_3$O$_2$, 409.0; m/z found, 409.9/411.9 [M+H]$^+$. $^1$H NMR (500 MHz, CD$_3$OD): δ 8.20 (d, J=8.5 Hz, 2H), 8.19 (br s, 1H), 7.89 (s, 1H), 7.88 (d, J=8.7 Hz, 2H), 7.82–7.80 (dd, J=8.5, 1.6 Hz, 1H), 7.68–7.62 (m, 3H).

Example 11

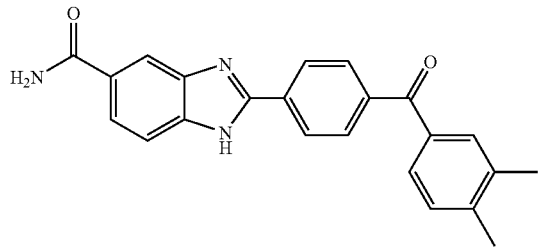

2-[4-(3,4-Dimethyl-benzoyl)-phenyl]-1H-benzoimidazole-5-carboxylic acid amide

The title compound was prepared as described in Example 4 substituting 3,4-dimethyl-benzaldehyde for 4-chloro-benzaldehyde in Step A. TLC (silica, 1% methanol saturated with ammonia/9% methanol/CH$_2$Cl$_2$): R$_f$=0.28. HPLC (Method A): R$_t$=7.53. MS (ESI+): mass calculated for C$_{23}$H$_{19}$N$_3$O$_2$, 369.1; m/z found, 370.1 [M+H]$^+$. $^1$H NMR (500 MHz, CD$_3$OD): δ 8.25 (d, J=8.4 Hz, 2H), 8.22 (s, 1H), 7.91 (d, J=8.3 Hz, 2H), 7.86–7.84 (dd, J=8.5, 1.6 Hz, 1H), 7.68 (br d, J=8.4 Hz, 1H), 7.60 (s, 1H), 7.53 (br d, J=7.7 Hz, 1H), 7.30 (d, J=7.7 Hz, 1H), 2.37 (s, 3H), 2.34 (s, 3H).

Example 12

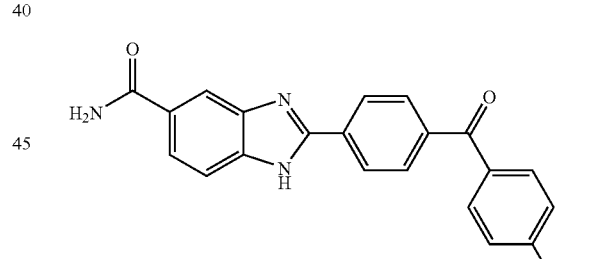

2-[4-(4-Ethyl-benzoyl)-phenyl]-1H-benzoimidazole-5-carboxylic acid amide

The title compound was prepared as described in Example 4 substituting 4-ethyl-benzaldehyde for 4-chloro-benzaldehyde in Step A. TLC (silica, 1% methanol saturated with ammonia/9% methanol/CH$_2$Cl$_2$): R$_f$=0.29. HPLC (Method A): R$_t$=7.67. MS (ESI+): mass calculated for C$_{23}$H$_{19}$N$_3$O$_2$, 369.1; m/z found, 370.1 [M+H]$^+$. $^1$H NMR (500 MHz, CD$_3$OD): δ 8.24 (d, J=8.5 Hz, 2H), 8.22 (s, 1H), 7.91 (d, J=8.6 Hz, 2H), 7.85–7.83 (dd, J=8.5, 1.6 Hz, 1H), 7.74 (d, J=8.2 Hz, 2H), 7.67 (d, J=8.4 Hz, 1H), 7.39 (d, J=8.1 Hz, 2H), 2.77–2.73 (q, J=7.6 Hz, 2H), 1.28 (t, J=7.6 Hz, 3H).

Example 13

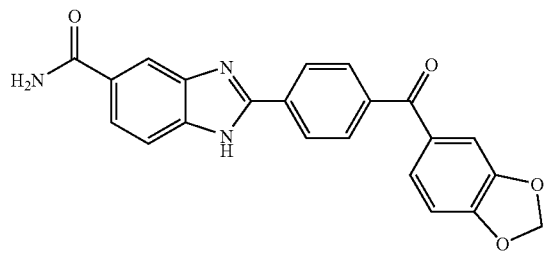

2-[4-(Benzo[1,3]dioxole-5-carbonyl)-phenyl]-1H-benzoimidazole-5-carboxylic acid amide The title compound was prepared as described in Example 4 substituting benzo[1,3]dioxole-5-carbaldehyde for 4-chloro-benzaldehyde in Step A. TLC (silica, 1% methanol saturated with ammonia/9%. methanol/$CH_2Cl_2$): $R_f$=0.28. HPLC (Method A): $R_t$=7.08. MS (ESI+): mass calculated for $C_{22}H_{15}N_3O_4$, 385.1; m/z found, 386.1 [M+H]+. 1H NMR (500 MHz, $CD_3OD$): δ 8.26 (d, J=8.4 Hz, 2H), 8.23 (br s, 1H), 7.90 (d, J=8.4 Hz, 2H), 7.86–7.84 (dd, J=8.5, 1.6 Hz, 1H), 7.69 (d, J=8.3 Hz, 1H), 7.42–7.40 (dd, J=8.1, 1.7 Hz, 1H), 7.35 (d, J=1.6 Hz, 1H), 6.96 (d, J=8.1 Hz, 1H), 6.1 (s, 2H).

Example 14

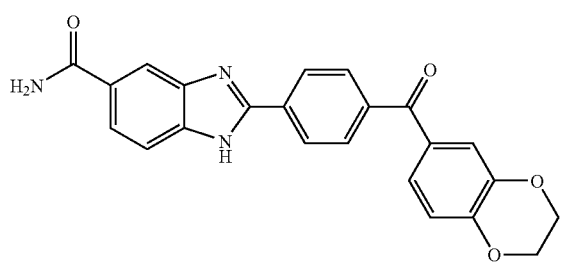

2-[4-(2,3-Dihydro-benzo[1,4]dioxine-6-carbonyl)-phenyl]-1H-benzoimidazole-5-carboxylic acid amide The title-compound was prepared as described in Example 4 substituting 2,3-dihydro-benzo[1,4]dioxine-6-carbaldehyde for 4-chloro-benzaldehyde in Step A. TLC (silica, 1% methanol saturated with ammonia/9% methanol/$CH_2Cl_2$): $R_f$=0.30. HPLC (Method A): $R_t$=7.29. MS (ESI+): mass calculated for $C_{23}H_{17}N_3O_4$, 399.1; m/z found, 400.1 [M+H]+. 1H NMR (500 MHz, $CD_3OD$): δ 8.23 (d, J=8.5 Hz, 2H), 8.21 (s, 1H), 7.87 (d, J=8.5 Hz, 2H), 7.85–7.83 (dd, J=8.5, 1.6 Hz, 1H), 7.67 (br d, J=8.4 Hz, 1H), 7.35–7.33(m, 2H), 6.96 (d, J=8.9 Hz, 1H), 4.35–4.33 (m, 2H), 4.30–4.28 (m, 2H).

Example 15

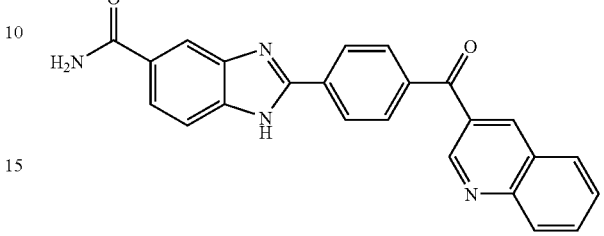

2-[4-(Quinoline-3-carbonyl)-phenyl]-1H-benzoimidazole-5-carboxylic acid amide

The title compound was prepared as described in Example 4 substituting quinoline-3-carbaldehyde for 4-chloro-benzaldehyde in Step A. TLC (silica, 1% methanol saturated with ammonia/9% methanol/$CH_2Cl_2$): $R_f$=0.20. HPLC (Method A): $R_t$=6.96. MS (ESI+): mass calculated for $C_{24}H_{16}N_4O_2$, 392.1; m/z found, 393.1 [M+H]+. 1H NMR (500 MHz, $CD_3OD$/DMSO-$d_6$): δ 9.28 (d, J=2.2 Hz, 1H), 8.80 (d, J=2.1 Hz, 1H), 8.41 (d, J=8.1 Hz, 2H), 8.24 (br s, 1H), 8.17–8.16 (dd, J=6.1, 0.8 Hz, 2H), 8.09 (d, J=8.3 Hz, 2H), 7.97–7.94 (m, 1H), 7.87–7.85 (dd, J=8.4, 1.2 Hz, 1H), 7.74 (t, J=7.1 Hz, 1H), 7.71 (br d, J=8.3 Hz, 1H).

Example 16

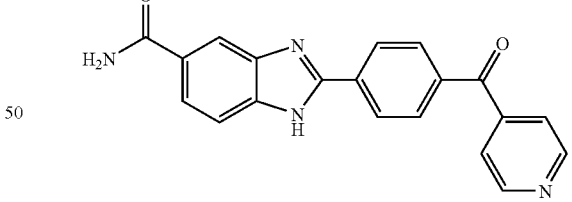

2-[4-(Pyridine-4-carbonyl)-phenyl]-1H-benzoimidazole-5-carboxylic acid amide

The title compound was prepared as described in Example 4 substituting pyridine-4-carbaldehyde for 4-chloro-benzaldehyde in Step A. TLC (silica, 1% methanol saturated with ammonia/9% methanol/$CH_2Cl_2$): $R_f$=0.25. HPLC (Method A): $R_t$=6.22. MS (ESI+): mass calculated for $C_{20}H_{14}N_4O_2$, 342.1; m/z found, 343.1 [M+H]+. 1H NMR (500 MHz, $CD_3OD$): δ 8.80 (d, J=6.0 Hz, 2H), 8.29 (d, J=8.4 Hz, 2H), 8.22 (br s, 1H), 8.01 (d, J=8.4 Hz, 2H), 7.86 (br d, J=8.3 Hz, 1H), 7.74 (d, J=6.0 Hz, 2H), 7.68 (br s, 1H).

Example 17

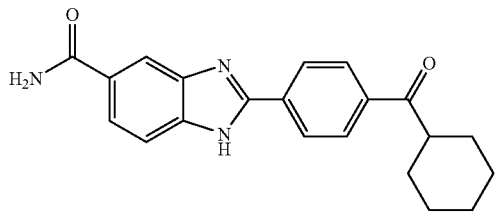

2-(4-Cyclohexanecarbonyl-phenyl)-1H-benzoimidazole-5-carboxylic acid amide

The title compound was prepared as described in Example 4 substituting cyclohexanecarbaldehyde for 4-chloro-benzaldehyde in Step A. TLC (silica, 1% methanol saturated with ammonia/9% methanol/$CH_2Cl_2$): $R_f$=0.29. HPLC (Method A): $R_t$=7.50. MS (ESI+): mass calculated for $C_{21}H_{21}N_3O_2$, 347.2, m/z found, 347.7 [M+H]$^+$. $^1$H NMR (500 MHz, $CD_3OD$): δ 8.13 (d, J=8.5 Hz, 2H), 8.12 (br s, 1H), 8.03 (d, J=8.6 Hz, 2H), 7.75–7.73 (dd, J=8.5, 1.2 Hz, 1H), 7.58 (br d, J=7.3 Hz, 1H), 3.36–3.31 (m, 1H), 1.83–1.77 (m, 2H), 1.76–1.73 (m, 2H), 1.68–1.64 (m, 1H), 1.45–1.32 (m, 4H), 1.23–1.18 (m, 1H).

Example 18

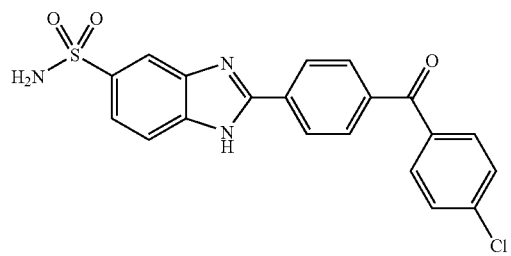

2-[4-(4-Chloro-benzoyl)-phenyl]-1H-benzoimidazole-5-sulfonic acid amide

The title compound was prepared as described in Example 1 substituting 3,4-diamino-benzenesulfonamide for 3,4-diamino-benzamide and 4-(4-chloro-benzoyl)-benzaldehyde for 4-(2-phenyl-[1,3]dioxolan-2-yl)-benzaldehyde in Step C (reaction mixture was heated to 60° C.). TLC (silica, 1% methanol saturated with ammonia/9% methanol/$CH_2Cl_2$): $R_f$=0.32. HPLC (Method A): $R_t$=8.03. MS (ESI+): mass calculated for $C_{20}H_{14}ClN_3O_3S$, 411.0; m/z found, 412.0 [M+H]$^+$. $^1$H NMR (500 MHz, DMSO-$d_6$): δ 13.48 (br s, 1H), 8.31 (d, J=8.3 Hz, 2H), 8.16 (br s, 1H), 7.88 (d, J=8.3 Hz, 2H), 7.76 (br s, 1H), 7.74 (d, J=8.5 Hz, 2H), 7.73 (br s, 1H), 7.60 (d, J=8.5 Hz, 1H), 7.25 (br s, 2H).

Example 19

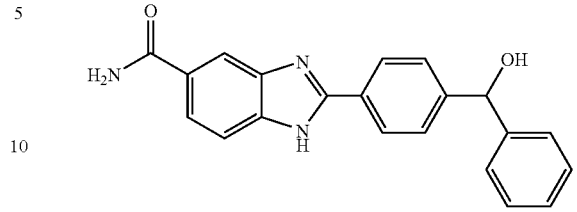

2-[4-(Hydroxy-phenyl-methyl)-phenyl]-1H-benzoimidazole-5-carboxylic acid amide

To a solution of 2-(4-benzoyl-phenyl)-1H-benzoimidazole-5-carboxylic acid amide (Example 3,18 mg, 0.05 mmol) in anhydrous methanol (2.0 mL) was added sodium borohydride (2.0 mg, 0.05 mmol) in one portion. The reaction mixture was stirred under $N_2$ for 1 h. The solvent was removed under reduced pressure, and the residue was re-dissolved in 1:1 ethyl acetate/$H_2O$ (40 mL). The solution was washed with $H_2O$ (20 mL) then brine (20 mL) and dried ($Na_2SO_4$). Solvent was removed under reduced pressure, and purification by chromatography (silica gel, 1% methanol saturated with ammonia/9% methanol/$CH_2Cl_2$) afforded 15 mg (83%) of the title compound. TLC (silica, 1% methanol saturated with ammonia/9% methanol/$CH_2Cl_2$): $R_f$=0.13. HPLC (Method A): $R_t$=6.36. MS (ESI+): mass calculated for $C_{21}H_{17}N_3O_2$, 343.1; m/z found, 344.1 [M+H]$^+$. $^1$H NMR (400 MHz, $CD_3OD$): δ 8.17 (br s, 1H), 8.07 (d, J=8.4 Hz, 2H), 7.82–7.80 (dd, J=8.4, 1.4 Hz, 1H), 7.63 (br d, J=6.7 Hz, 1H), 7.58 (d, J=8.2 Hz, 2H), 7.42–7.40 (dd, J=8.5, 1.4 Hz, 2H), 7.32 (t, J=7.5 Hz, 2H), 7.26–7.22 (m, 1H), 5.85 (s, 1H).

Example 20

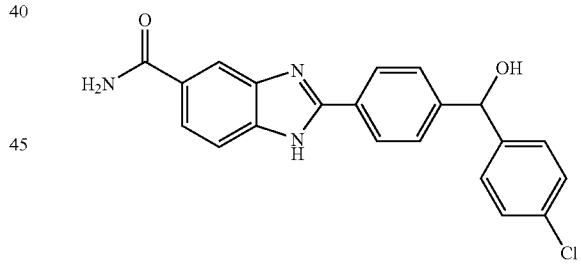

2-{4-[(4-Chloro-phenyl)-hydroxy-methyl]-phenyl}-1H-benzoimidazole-5-carboxylic acid amide The title compound was prepared as described in Example 19 from 2-[4-(4-chloro-benzoyl)-phenyl]-1H-benzoimidazole-5-carboxylic acid amide (Example 4, 22 mg, 0.06 mmol). Purification by chromatography (silica gel, 1% methanol saturated with ammonia/9% methanol/$CH_2Cl_2$) afforded 13 mg (60%) of the title compound. TLC (silica, 1% methanol saturated with ammonia/9% methanol/$CH_2Cl_2$): $R_f$=0.14. HPLC (Method A): $R_t$=7.02. MS (ESI+): mass calculated for $C_{21}H_{16}ClN_3O_2$, 377.1; m/z found, 378.1 [M+H]$^+$. $^1$H NMR (500 MHz, $CD_3OD$): δ 8.17 (br s, 1H), 8.08 (d, J=8.4 Hz, 2H), 7.81 (br d, J=7.5 Hz, 1H), 7.64 (br s, 1H), 7.57 (d, J=8.2 Hz, 2H), 7.40 (d, J=8.4 Hz, 2H), 7.33 (d, J=8.6 Hz, 2H), 5.85 (s, 1H).

Example 21

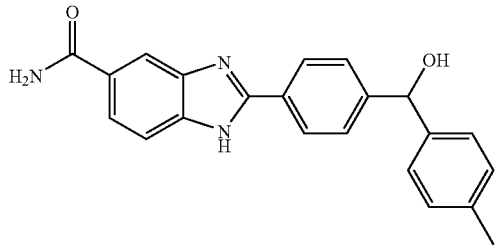

2-[4-(Hydroxy-p-tolyl-methyl)-phenyl]-1H-benzoimidazole-5-carboxylic acid amide

The title compound was prepared as described in Example 19 from 2-[4-(4-methyl-benzoyl)-phenyl]-1H-benzoimidazole-5-carboxylic acid amide (Example 5, 60 mg, 0.16 mmol). Purification by chromatography (silica gel, 1% methanol saturated with ammonia/9% methanol/$CH_2Cl_2$) afforded 55 mg (91%) of the title compound. TLC (silica, 1% methanol saturated with ammonia/9% methanol/$CH_2Cl_2$): $R_f$=0.2. HPLC (Method A): $R_t$=6.89. MS (ESI+): mass calculated for $C_{22}H_{19}N_3O_2$, 357.1; m/z found, 358.1 [M+H]$^+$. $^1$H NMR (500 MHz, $CD_3OD$): δ 8.21–8.11 (br m, 1H), 8.06 (d, J=8.3 Hz, 2H), 7.80 (br s, 1H), 7.67 (br s, 1H), 7.56 (d, J=8.2 Hz, 2H), 7.28 (d, J=8.0 Hz, 2H), 7.15 (d, J=7.9 Hz, 2H), 5.82 (s, 1H), 2.30 (s, 3H).

Example 22

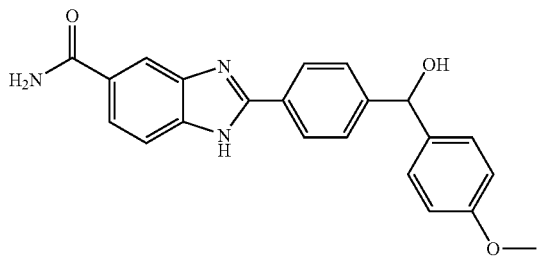

2-{4-[Hydroxy-(4-methoxy-phenyl)-methyl]-phenyl}-1H-benzoimidazole-5-carboxylic acid amide The title compound was prepared as described in Example 19 from 2-[4-(4-methoxy-benzoyl)-phenyl]-1H-benzoimidazole-5-carboxylic acid amide (Example 6, 35 mg, 0.09 mmol). Purification by chromatography (silica gel, 1% methanol saturated with ammonia/9% methanol/$CH_2Cl_2$) afforded 25 mg (71%) of the title compound. TLC (silica, 1% methanol saturated with ammonia/9% methanol/$CH_2Cl_2$): $R_f$=0.13. HPLC (Method A): $R_t$=6.57. MS (ESI+): mass calculated for $C_{22}H_{19}N_3O_3$, 373.1; m/z found, 374.1 [M+H]$^+$. $^1$H NMR (500 MHz, $CD_3OD$): δ 8.10 (br s, 1H), 7.97 (d, J=8.3 Hz, 2H), 7.71 (br d, J=7.7 Hz, 1H), 7.53 (br s, 1H), 7.47 (d, J=8.2 Hz, 2H), 7.20 (d, J=8.7 Hz, 2H), 6.79 (d, J=8.7 Hz, 2H), 5.71 (s, 1H), 3.66 (s, 3H).

Example 23

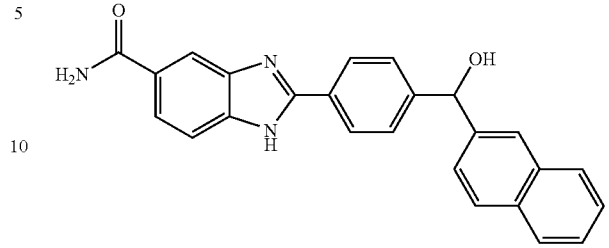

2-[4-(Hydroxy-naphthalen-2-yl-methyl)-phenyl]-1H-benzoimidazole-5-carboxylic acid amide The title compound was prepared as described in Example 19 from 2-[4-(naphthalene-2-carbonyl)-phenyl]-1H-benzoimidazole-5-carboxylic acid amide (Example 7, 60 mg, 0.15 mmol). Purification by chromatography (silica gel, 1% methanol saturated with ammonia/9% methanol/$CH_2Cl_2$) afforded 43 mg (72% of the title compound. TLC (silica, 1% methanol saturated with ammonia/9% methanol/$CH_2Cl_2$): $R_f$=0.21. HPLC (Method A): $R_t$=7.18. MS (ESI+): mass calculated for $C_{25}H_{19}N_3O_2$, 393.1; m/z found, 394.1 [M+H]$^+$. $^1$H NMR (500 MHz, $CD_3OD$): δ 8.18 (br s, 1H), 8.08 (d, J=8.4 Hz, 2H), 7.92 (s, 1H), 7.84 (d, J=8.9 Hz, 1H), 7.80 (d, J=8.5 Hz, 3H), 7.63 (d, J=8.3 Hz, 3H), 7.48–7.41 (m, 3H), 6.02 (s, 1H).

Example 24

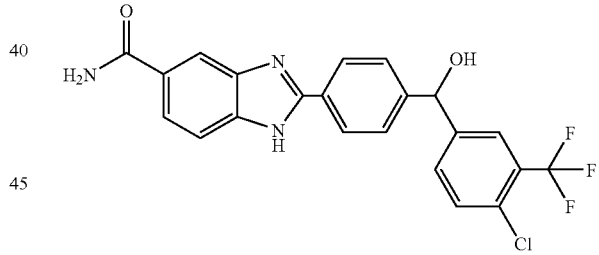

2-{4-[(4-Chloro-3-trifluoromethyl-phenyl)-hydroxy-methyl]-phenyl}-1H-benzoimidazole-5-carboxylic acid amide The title compound was prepared as described in Example 19 from 2-[4-(4-chloro-3-trifluoromethyl-benzoyl)-phenyl]-1H-benzoimidazole-5-carboxylic acid amide (Example 8, 69 mg, 0.15 mmol). Purification by chromatography (silica gel, 1% methanol saturated with ammonia/9% methanol/$CH_2Cl_2$) afforded 60 mg (87%) of the title compound. TLC (silica, 1% methanol saturated with ammonia/9% methanol/$CH_2Cl_2$): $R_f$=0.17. HPLC (Method A): $R_t$=7.5. MS (ESI−): mass calculated for $C_{22}H_{15}ClF_3N_3O_2$, 445.1; m/z found, 444.5 [M−H]$^−$. $^1$H NMR (500 MHz, $CD_3OD$): δ 8.17 (br s, 1H), 8.10 (d, J=8.4 Hz, 2H), 7.85 (d, J=1.8 Hz, 1H), 7.81 (br d, J=8.4 Hz, 1H), 7.64–7.62 (dd, J=8.3, 1.9 Hz, 2H), 7.59–7.55 (m, 3H), 5.93 (s, 1H).

Example 25

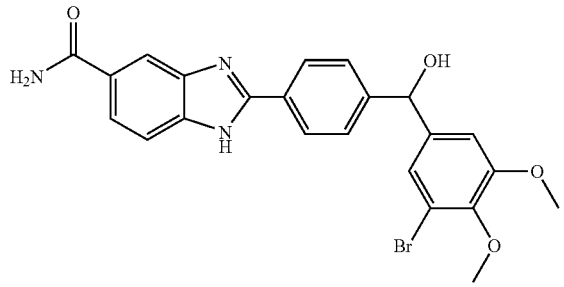

2-{4-[(3-Bromo-4,5-dimethoxy-phenyl)-hydroxy-methyl]-phenyl}-1H-benzoimidazole-5-carboxylic acid amide The title compound was prepared as described in Example 19 from 2-[4-(3-bromo-4,5-dimethoxy-benzoyl)-phenyl]-1H-benzoimidazole-5-carboxylic acid amide (Example 9, 60 mg, 0.12 mmol). Purification by chromatography (silica gel, 1% methanol saturated with ammonia/9% methanol/$CH_2Cl_2$) afforded 37 mg ($_{62}$%) of the title compound. TLC (silica, 1% methanol saturated with ammonia/9% methanol/$CH_2Cl_2$): $R_f$=0.18. HPLC (Method A): $R_t$=6.82. MS (ESI+): mass calculated for $C_{23}H_{20}BrN_3O_4$, 481.1; m/z found, 482.0/484.0 [M+H]$^+$. $^1$H NMR (500 MHz, $CD_3OD$): δ 8.17 (br s, 1H), 8.07 (d, J=8.4 Hz, 2H), 7.82–7.80 (dd, J=8.5, 1.2 Hz, 1H), 7.63 (d, J=7.6 Hz, 1H), 7.57 (d, J=8.3 Hz, 2H), 7.20(s, 1H), 7.11 (s, 1H), 6.14 (s, 1H), 3.82 (s, 3H), 3.80 (s, 3H).

Example 26

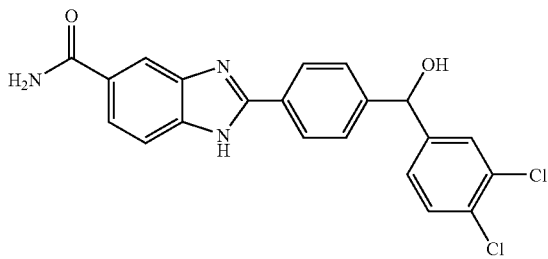

2-{4-[(3,4-Dichloro-phenyl)-hydroxy-methyl]-phenyl}-1H-benzoimidazole-5-carboxylic acid amide The title compound was prepared as described in Example 19 from 2-[4-(3,4-dichloro-benzoyl)-phenyl]-1H-benzoimidazole-5-carboxylic acid amide (Example 10, 70 mg, 0.17 mmol). HPLC (Method A): $R_t$=7.29. MS (ESI+): mass calculated for $C_{21}H_{15}Cl_2N_3O_2$, 411.1; m/z found, 412.2 [M+H]$^+$. $^1$H NMR (500 MHz, DMSO-$d_6$): δ 13.58 (br s, 1H), 8.23 (d, J=8.2 Hz, 2H), 8.16 (br s, 1H), 8.01 (br s, 1H), 7.77 (dd, J=8.1 Hz, 1H), 7.68 (d, J=1.8 Hz, 1H), 7.59 (d, J=8.3 Hz, 2H), 7.57 (d, J=8.3 Hz, 2H), 7.41–7.39 (dd, J=8.4, 1.8 Hz, 1H), 7.24 (br s, 1H), 6.36 (d, J=4.1 Hz, 1H), 5.83 (d, J=3.8 Hz, 1H).

Example 27

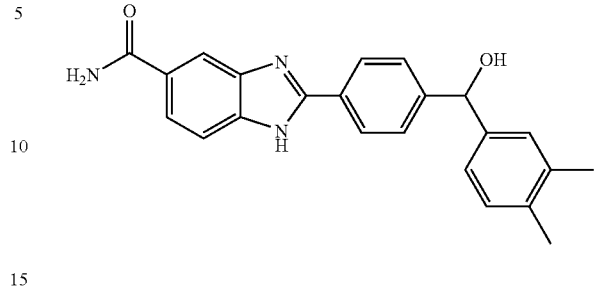

2-{4-[(3,4-Dimethyl-phenyl)-hydroxy-methyl]-phenyl}-1H-benzoimidazole-5-carboxylic acid amide The title compound was prepared as described in Example 19 from 2-[4-(3,4-dimethyl-benzoyl)-phenyl]-1H-benzoimidazole-5-carboxylic acid amide (Example 11, 60 mg, 0.16 mmol). Purification by chromatography (silica gel, 1% methanol saturated with ammonia/9% methanol/$CH_2Cl_2$) afforded 50.2 mg (84%) of the title compound. TLC (silica, 1% methanol saturated with ammonia/9% methanol/$CH_2Cl_2$): $R_f$=0.13. HPLC (Method A): $R_t$=7.09. MS (ESI+): mass calculated for $C_{23}H_{21}N_3O_2$, 371.2; m/z found, 372.2 [M+H]$^+$. $^1$H NMR (500 MHz, $CD_3OD$): δ 8.17 (br s, 1H), 8.05 (d, J=8.4 Hz, 2H), 7.81–7.79 (dd, J=8.4, 1.4 Hz, 1H), 7.62 (br d, J=7.6 Hz, 1H), 7.56 (d, J=8.1 Hz, 2H), 7.15 (s, 1H), 7.10–7.06 (m, 2H), 5.78 (s, 1H), 2.23 (s, 3H), 2.22 (s, 3H).

Example 28

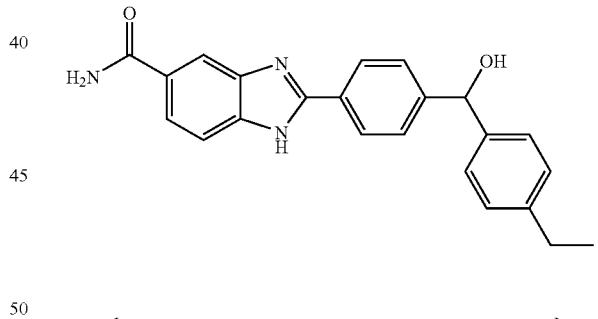

2-{4-[(4-Ethyl-phenyl)-hydroxy-methyl]-phenyl}-1H-benzoimidazole-5-carboxylic acid amide The title compound was prepared as described in Example 19 from 2-[4-(4-ethyl-benzoyl)-phenyl]-1H-benzoimidazole-5-carboxylic acid amide (Example 12, 60 mg, 0.16 mmol). Purification by chromatography (silica gel, 1% methanol saturated with ammonia/9% methanol/$CH_2Cl_2$) afforded 52 mg (87%) of the title compound. TLC (silica, 1% methanol saturated with ammonia/9% methanol/$CH_2Cl_2$): $R_f$=0.17. HPLC (Method A): $R_t$=7.17. MS (ESI+): mass calculated for $C_{23}H_{21}N_3O_2$, 371.2; m/z found, 372.1 [M+H]$^+$. $^1$H NMR (500 MHz, $CD_3OD$): δ 8.17 (br s, 1H), 8.06 (d, J=8.4 Hz, 2H), 7.81–7.79 (dd, J=8.5, 1.6 Hz, 1H), 7.62 (br d, J=8.3 Hz, 1H), 7.56. (d, J=8.1 Hz, 2H), 7.29 (d, J=8.1 Hz, 2H), 7.16 (d, J=8.2 Hz, 2H), 5.82 (s, 1H), 2.62–2.58 (q, J=7.6 Hz, 2H), 1.19 (t, J=7.6 Hz, 3H).

Example 29

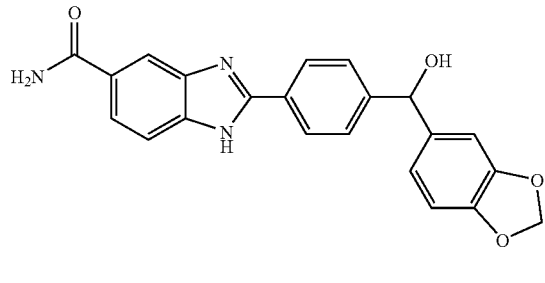

2-[4-(Benzo[1,3]dioxol-5-yl-hydroxy-methyl)-phenyl]-1H-benzoimidazole-5-carboxylic acid amide The title compound was prepared as described in Example 19 from 2-[4-(benzo[1,3]dioxole-5-carbonyl)-phenyl]-1H-benzoimidazole-5-carboxylic acid amide (Example 13, 40 mg, 0.1 mmol). Purification by chromatography (silica gel, 1% methanol saturated with ammonia/9% methanol/$CH_2Cl_2$) afforded 29 mg (71%) of the title compound. TLC (silica, 1% methanol saturated with ammonia/9% methanol/$CH_2Cl_2$): $R_f$=0.16. HPLC (Method A): $R_t$=6.78. MS (ESI+): mass calculated for $C_{22}H_{17}N_3O_4$, 387.1; m/z found, 388.1 [M+H]$^+$. $^1$H NMR (500 MHz, $CD_3OD$): δ 8.17 (br s, 1H), 8.06 (d, J=8.4 Hz, 2H), 7.82–7.80 (dd, J=8.5, 1.6 Hz, 1H), 7.63 (d, J=8.5 Hz, 1H), 7.56 (d, J=8.2 Hz, 2H), 6.89–6.87 (dd, J=8.1, 1.6 Hz, 1H), 6.86 (d, J=1.6 Hz, 1H), 6.77 (d, J=8.0 Hz, 1H), 5.91–5.89 (m, 2H), 5.77 (s, 1H).

Example 30

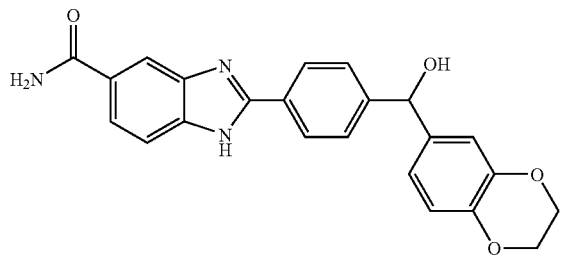

2-{4-[(2,3-Dihydro-benzo[1,4]dioxin-6-yl)-hydroxy-methyl]-phenyl}-1H-benzoimidazole-5-carboxylic acid amide The title compound was prepared as described in Example 19 from 2-[4-(2,3-dihydro-benzo[1,4]dioxine-6-carbonyl)-phenyl]-1H-benzoimidazole-5-carboxylic acid amide (Example 14, 60 mg, 0.15 mmol). Purification by chromatography (silica gel, 1% methanol saturated with ammonia/9% methanol/$CH_2Cl_2$) afforded 46.6 mg (78%) of the title compound. TLC (silica, 1% methanol saturated with ammonia/9% methanol/$CH_2Cl_2$): $R_f$=0.16. HPLC (Method A): $R_t$=6.74. MS (ESI+): mass calculated for $C_{23}H_{19}N_3O_4$, 401.1; m/z found, 402.1 [M+H]$^+$. $^1$H NMR (500 MHz, $CD_3OD$): δ 8.17 (br s, 1H), 8.06 (d, J=8.3 Hz, 2H), 7.82–7.80 (dd, J=8.4, 1.4 Hz, 1H), 7.63 (br d, J=8.0 Hz, 1H), 7.55 (d, J=8.3 Hz, 2H), 6.86(d, J=1.9 Hz, 1H), 6.84–6.82 (dd, J=8.3, 1.9 Hz, 1H), 6.77 (d, J=8.3 Hz, 1H), 5.74 (s, 1H), 4.19 (s, 4H).

Example 31

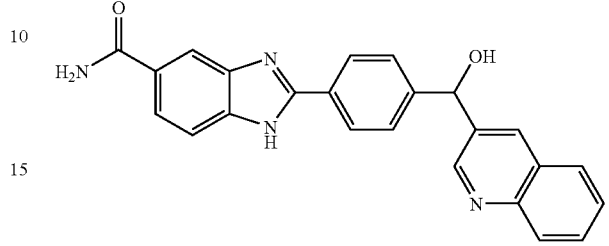

2-[4-(Hydroxy-quinolin-3-yl-methyl)-phenyl]-1H-benzoimidazole-5-carboxylic acid amide The title compound was prepared as described in Example 19 from 2-[4-(quinoline-3-carbonyl)-phenyl]-1H-benzoimidazole-5-carboxylic acid amide (Example 15, 40 mg, 0.1 mmol). Purification by chromatography (silica gel, 1% methanol saturated with ammonia/9% methanol/$CH_2Cl_2$) afforded 13.9 mg, (35%) of the title compound. HPLC (Method A): $R_t$=6.04. MS (ESI+): mass calculated for $C_{24}H_{18}N_4O_2$, 394.1; m/z found, 395.1 [M+H]$^+$. $^1$H NMR (500 MHz, $CD_3OD$): δ 8.78 (d, J=2.1 Hz, 1H), 8.26 (d, J=1.0 Hz, 1H), 8.25 (br s, 1H), 8.02 (d, J=8.4 Hz, 2H), 7.90 (d, J=8.5 Hz, 1H), 7.84 (d, J=8.2 Hz, 1H), 7.71 (d, J=8.3 Hz, 1H), 7.66–7.63 (m, 1H), 7.58 (d, J=8.3 Hz, 2H), 7.52 (br s, 1H), 7.51–7.49 (m, 1H), 6.03 (s, 1H).

Example 32

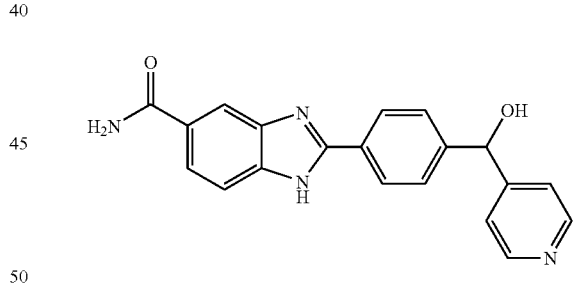

2-[4-(Hydroxy-pyridin-4-yl-methyl)-phenyl]-1H-benzoimidazole-5-carboxylic acid amide The title compound was prepared as described in Example 19 from 2-[4-(pyridine-4-carbonyl)-phenyl]-1H-benzoimidazole-5-carboxylic acid amide (Example 16, 15 mg, 0.04 mmol). Purification by chromatography (silica gel, 1% methanol saturated with ammonia/9% methanol/$CH_2Cl_2$) afforded 10.2 mg (68%) of the title compound. TLC (silica, 1% methanol saturated with ammonia/9% methanol/$CH_2Cl_2$): $R_f$=0.09. HPLC (Method A): $R_t$=5.64. MS (ESI+): mass calculated for $C_{20}H_{16}N_4O_2$, 344.1; m/z found, 345.1 [M+H]$^+$. $^1$H NMR (500 MHz, $CD_3OD$): δ 8.39 (d, J=6.2 Hz, 2H), 8.12 (br s, 1H), 8.00 (d, J=8.3 Hz, 2H), 7.75 (br s, 1H), 7.51 (d, J=8.3 Hz, 2H), 7.42 (d, J=6.0 Hz, 2H), 5.79 (s, 1H).

Example 33

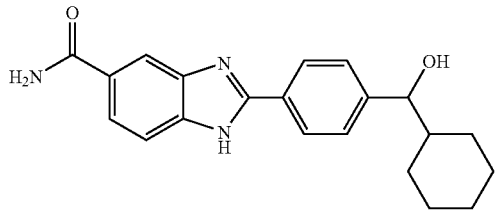

2-[4-(Cyclohexyl-hydroxy-methyl)-phenyl]-1H-benzoimidazole-5-carboxylic acid amide The title compound was prepared as described in Example 19 from 2-(4-cyclohexanecarbonyl-phenyl)-1H-benzoimidazole-5-carboxylic acid amide (Example 17, 90 mg, 0.26 mmol). Purification by chromatography (silica gel, 1% methanol saturated with ammonia/9% methanol/$CH_2Cl_2$) afforded 31 mg (34%) of the title compound. TLC (silica, 1% methanol saturated with ammonia/9% methanol/$CH_2Cl_2$): $R_f$=0.2. MS (ESI+): mass calculated for $C_{21}H_{23}N_3O_2$, 349.2; m/z found, 350.3 [M+H]$^+$. $^1$H NMR (500 MHz, $CD_3OD$): δ 8.18 (br s, 1H), 8.07 (d, J=8.3 Hz, 2H), 7.81 (d, J=8.3 Hz, 1H), 7.63 (br s, 1H), 7.49 (d, J=8.3 Hz, 2H), 4.40 (d, J=7.0 Hz, 1H), 1.99 (d, J=13.1 Hz, 1H), 1.77 (d, J=12.9 Hz, 1H), 1.69–1.60 (m, 3H), 1.41 (d, J=12.9 Hz, 1H), 1.28–1.01 (m, 5H).

Example 34

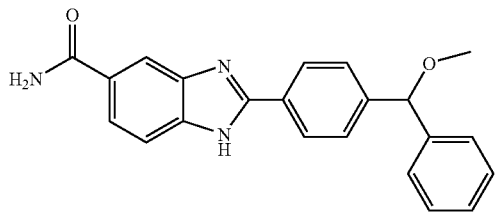

2-[4-(Methoxy-phenyl-methyl)-phenyl]-1H-benzoimidazole-5-carboxylic acid amide

To a solution of 2-[4-(hydroxy-phenyl-methyl)-phenyl]-1H-benzoimidazole-5-carboxylic acid amide (Example 19, 8.7 mg, 0.02 mmol) in chloroform (1.0 mL) was added concentrated HCl (0.1 mL). The reaction mixture was stirred at RT for 2 h. Organics were removed under reduced pressure, and purification using preparative TLC (silica, 1% methanol saturated with ammonia/9% methanol/$CH_2Cl_2$) afforded 4.2 mg (47%) of the title compound. HPLC (Method A): $R_t$=6.97. MS (ESI+): mass calculated for $C_{22}H_{19}N_3O_2$, 357.1; m/z found, 358.2 [M+H]$^+$. $^1$H NMR (400 MHz, $CD_3OD$): δ 8.18 (br s, 1H), 8.08 (d, J=8.2 Hz, 2H), 7.82 (br d, J=8.0 Hz, 1H), 7.64 (br s, 1H), 7.56 (d, J=8.3 Hz, 2H), 7.40 (d, J=8.0 Hz, 2H), 7.35 (t, J=7.5 Hz, 2H), 7.28–7.25 (m, 1H), 5.39 (s, 1H), 3.40 (s, 3H).

Example 35

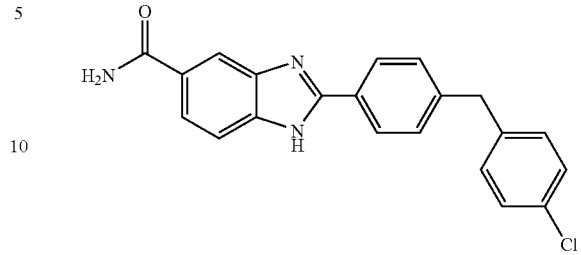

2-[4-(4-Chloro-benzyl)-phenyl]-1H-benzoimidazole-5-carboxylic acid amide

To a solution of 2-{4-[(4-chloro-phenyl)-hydroxy-methyl]-phenyl}-1H-benzoimidazole-5-carboxylic acid amide (Example 20, 50 mg, 0.13 mmol) in TFA (5.0 mL) was added sodium borohydride (211 mg, 4.2 equiv), and the reaction mixture was stirred at RT for 16 h. Water (5.0 mL) was added to the mixture, which was then adjusted to pH 9 with 1 N NaOH. The precipitate was collected by filtration and washed with $H_2O$ (20 mL). Purification by chromatography (silica gel, 1% methanol saturated with ammonia/9% methanol/$CH_2Cl_2$) afforded 39 mg (81%) of the title compound. HPLC (Method A): $R_t$=7.64. MS (ESI+): mass calculated for $C_{21}H_{16}ClN_3O$, 361.1; m/z found, 362.2 [M+H]$^+$. $^1$H NMR (500 MHz, $CD_3OD$): δ 8.23 (d, J=1.4 Hz, 1H), 8.06 (d, J=8.2 Hz, 2H), 7.94–7.92 (dd, J=8.5, 1.6 Hz, 1H), 7.74 (d, J=8.5 Hz, 1H), 7.48 (d, J=8.2 Hz, 2H), 7.31 (d, J=8.4 Hz, 2H): 7.25 (d, J=8.4 Hz, 2H), 4.09 (s, 2H).

Example 36

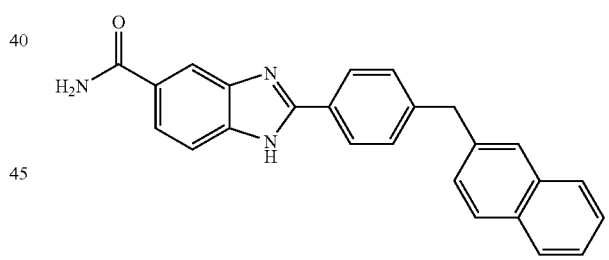

2-(4-Naphthalen-2-ylmethyl-phenyl)-1H-benzoimidazole-5-carboxylic acid amide

The title compound was prepared as described in Example 35 from 2-[4-(hydroxy-naphthalen-2-yl-methyl)-phenyl]-1H-benzoimidazole-5-carboxylic acid amide (Example 23, 20 mg, 0.05 mmol). Purification by chromatography (silica gel, 1% methanol saturated with ammonia/9% methanol/$CH_2Cl_2$) afforded 19 mg (100%) of the title compound. TLC (silica, 1% methanol saturated with ammonia/9% methanol/$CH_2Cl_2$): $R_f$=0.33. HPLC (Method A): $R_t$=7.80. MS (ESI+): mass calculated for $C_{25}H_{19}N_3O$, 377.2; m/z found, 378.1 [M+H]$^+$. $^1$H NMR (500 MHz, $CD_3OD$): δ 8.17 (dd, J=1.5, 0.5 Hz, 1H), 7.97 (d, J=8.4 Hz, 2H), 7.93–7.91 (dd, J=8.5, 1.5 Hz, 1H), 7.71–7.67 (m, 4H), 7.63 (s, 1H), 7.49 (d, J=8.4 Hz, 2H), 7.37–7.37 (m, 2H), 7.27–7.25 (dd, J=8.4, 1.6 Hz, 1H), 4.18 (s, 2H).

Example 37

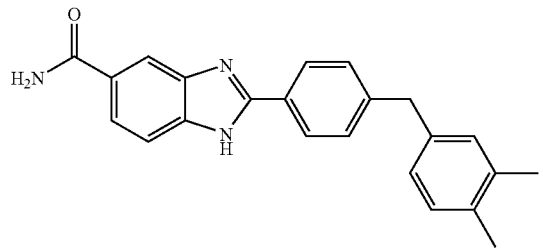

2-[4-(3,4-Dimethyl-benzyl)-phenyl]-1H-benzoimidazole-5-carboxylic acid amide

The title compound was prepared as described in Example 35 from 2-{4-[(3,4-dimethyl-phenyl)-hydroxy-methyl]-phenyl}-1H-benzoimidazole-5-carboxylic acid amide (Example 27, 14 mg, 0.03 mmol). Purification by chromatography (silica gel, 1% methanol saturated with ammonia/9% methanol/CH$_2$Cl$_2$) afforded 11.1 mg (83%) of the title compound. TLC (silica, 1% methanol saturated with ammonia/9% methanol/CH$_2$Cl$_2$): R$_f$=0.39. HPLC (Method A): R$_t$=8.11. MS (ESI+): mass calculated for C$_{23}$H$_{21}$N$_3$O, 355.2; m/z found, 356.1 [M+H]$^+$. $^1$H NMR (500 MHz, CD$_3$OD): δ 8.17 (s, 1H), 8.04 (d, J=8.2 Hz, 2H), 7.81 (br d, J=8.2 Hz, 1H), 7.63 (br s, 1H), 7.40 (d, J=8.2 Hz, 2H), 7.05 (d, J=7.7 Hz, 1H), 7.02 (s, 1H), 6.96 (d, J=7.6 Hz, 1H), 3.97 (s, 2H), 2.22 (d, J=4.1 Hz, 6H).

Example 38

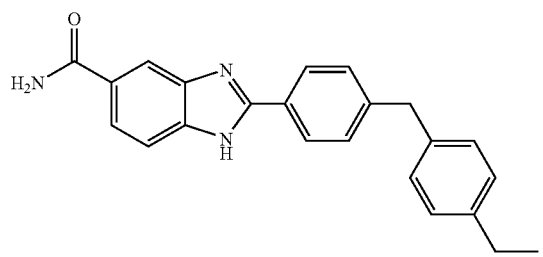

2-[4-(4-Ethyl-benzyl)-phenyl]-1H-benzoimidazole-5-carboxylic acid amide

The title compound was prepared as described in Example 35 from 2-{4-[(4-ethyl-phenyl)-hydroxy-methyl]-phenyl}-1H-benzoimidazole-5-carboxylic acid amide (Example 28, 26.5 mg, 0.07 mmol). Purification by chromatography (silica gel, 1% methanol saturated with ammonia/9% methanol/CH$_2$Cl$_2$) afforded 19 mg (76%) of the title compound. TLC (silica, 1% methanol saturated with ammonia/9% methanol/CH$_2$Cl$_2$): R$_f$=0.41. HPLC (Method A): R$_t$=7.84. MS (ESI+): mass calculated for C$_{23}$H$_{21}$N$_3$O, 355.2; m/z found, 356.1 [M+H]$^+$. $^1$H NMR (500 MHz, CD$_3$OD): δ 8.16 (d, J=1.5 Hz, 1H), 7.94 (d, J=8.4 Hz, 2H), 7.89 (dd, J=8.6, 1.6 Hz, 1H), 7.67 (d, J=8.5 Hz, 1H), 7.41 (d, J=8.4 Hz, 2H), 7.05–7.04 (m, 4H), 3.96 (s, 2H), 2.53–2.48 (q, J=7.6 Hz, 2H), 1.10 (t, J=7.6 Hz, 3H).

Example 39

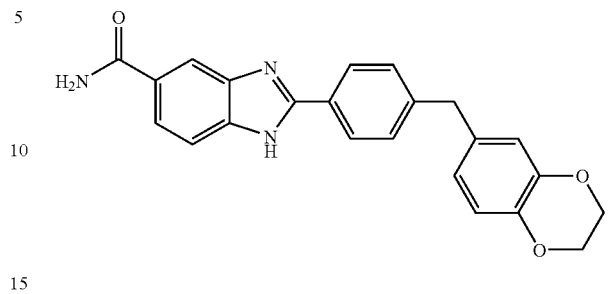

2-[4-(2,3-Dihydro-benzo[1,4]dioxin-6-ylmethyl)-phenyl]-1H-benzoimidazole-5-carboxylic acid amide The title compound was prepared as described in Example 35 from 2-{4-[(2,3-dihydro-benzo[1,4]dioxin-6-yl)-hydroxy-methyl]-phenyl}-1H-benzoimidazole-5-carboxylic acid amide (Example 30, 15.3 mg, 0.04 mmol). Purification by chromatography (silica gel, 1% methanol saturated with ammonia/9% methanol/CH$_2$Cl$_2$) afforded 12.1 mg (83%) of the title compound. TLC (silica, 1% methanol saturated with ammonia/9% methanol/CH$_2$Cl$_2$): R$_f$=0.30. HPLC (Method A): R$_t$=7.19. MS (ESI+): mass calculated for C$_{23}$H$_{19}$N$_3$O$_3$, 385.1; m/z found, 386.1 [M+H]$^+$. $^1$H NMR (500 MHz, CD$_3$OD): δ 8.10 (d, J=1.4 Hz, 1H), 7.92 (d, J=8.3 Hz, 2H), 7.79–7.77 (dd, J=8.5, 1.6 Hz, 1H), 7.59 (d, J=8.5 Hz, 1H), 7.32 (d, J=8.3 Hz, 2H), 6.65 (d, J=8.9 Hz, 1H), 6.59–6.57 (m, 2H), 4.09 (s, 1H), 3.84 (s, 2H).

Example 40

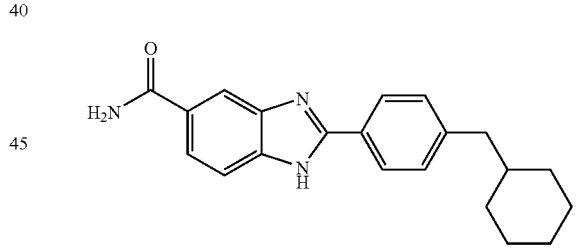

2-(4-Cyclohexylmethyl-phenyl)-1H-benzoimidazole-5-carboxylic acid amide

The title compound was prepared as described in Example 35 from 2-[4-(cyclohexyl-hydroxy-methyl)-phenyl]-1H-benzoimidazole-5-carboxylic acid amide (Example 33, 11.4 mg, 0.03 mmol). Product was isolated as a TFA salt (7.3 mg, 50%). HPLC (Method A): R$_t$=8.46. MS (ESI+): mass calculated for C$_{21}$H$_{23}$N$_3$O, 333.2, m/z found, 446.3 [M+H]$^+$+TFA. $^1$H NMR (500 MHz, CD$_3$OD): δ 8.19 (d, J=1.5 Hz, 1H), 8.08 (d, J=8.4 Hz, 2H), 7.92–7.89 (d, J=8.6, 1.5 Hz, 1H), 7.69 (d, J=8.5 Hz, 1H), 7.57 (d, J=8.4 Hz, 2H), 5.69 (d, J=7.9 Hz, 1H), 1.96–1.91 (m, 1H), 1.87–1.82 (m, 1H), 1.73–1.69 (m, 1H), 1.66–1.59 (m, 2H), 1.35–1.32 (m, 1H), 1.20–0.95 (m, 6H).

Example 41

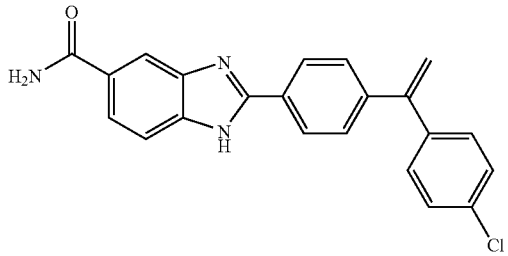

2-{4-[1-(4-Chloro-phenyl)-vinyl]-phenyl}-1H-benzoimidazole-5-carboxylic acid amide A. 1-(4-Chloro-phenyl)-1-(4-[1,3]dioxan-2-yl-phenyl)-ethanol. To a solution of 1-(4-chloro-phenyl)-ethanone (582 mg, 3.7 mmol) in anhydrous THF (25 mL), cooled to −78° C., was added 4-(1,3-dioxan-2-yl)phenylmagnesium bromide (16 mL, 0.25 M in THF) dropwise. The reaction mixture was stirred 1 h at −78° C. then was quenched with saturated aqueous NH$_4$Cl (50 mL). The resulting mixture was extracted with Et$_2$O (2×100 mL), and the combined extracts were washed with H$_2$O (100 mL) then brine (100 mL), and dried (MgSO$_4$). Solvent was removed under reduced pressure. Purification of the residue by chromatography (silica gel, 50% ethyl acetate/hexanes) afforded 627 mg (52%) of the title compound. TLC (silica, 50% ethyl acetate/hexanes): R$_f$=0.42. HPLC (Method A): R$_t$=10.16. $^1$H NMR (500 MHz, CD$_3$OD): δ 7.41 (d, J=8.3 Hz, 2H), 7.35 (d, J=8.5 Hz, 2H), 7.27 (d, J=8.7 Hz, 2H), 7.21 (d, J=8.7 Hz, 2H), 5.46 (s, 1H), 4.24–4.20 (m, 2H), 3.98–3.92 (m, 2H), 2.94 (s, 1H), 2.23–2.14 (m, 1H), 1.84 (s, 3H), 1.43–1.39 (m, 1H).

B. 4-[1-(4-Chloro-phenyl)-vinyl]-benzaldehyde. This compound was prepared as described in Example 3 substituting 1-(4-chloro-phenyl)-1-(4-[1,3]dioxan-2-yl-phenyl)-ethanol (150 mg, 0.47 mmol) for 4-(2-phenyl-[1,3]dioxolan-2-yl)-benzaldehyde in Step A. The title compound (100 mg, 88%) was used without purification in the next reaction. TLC (silica, 50% ethyl acetate/hexanes): R$_f$=0.66. HPLC (Method A): R$_t$=10.65. $^1$H NMR (500 MHz, CD$_3$OD): δ 10.02 (s, 1H), 7.86 (d, J=8.2 Hz, 2H), 7.47 (d, J=8.2 Hz, 2H), 7.32 (d, J=8.6 Hz, 2H), 7.24 (d, J=8.6 Hz, 2H), 5.58 (s, 1H), 5.57 (s, 1H).

C. 2-{4-[1-(4-Chloro-Phenyl)-vinyl]-phenyl}-1H-benzoimidazole-5-carboxylic acid amide. This compound was prepared as described in Example 1 substituting 4-[1-(4-chloro-phenyl)-vinyl]-benzaldehyde (100 mg, 0.4 mmol) for 4-(2-phenyl-[1,3]dioxolan-2-yl)-benzaldehyde in Step C. Purification by chromatography (silica gel, 1% methanol saturated with ammonia/9% methanol/CH$_2$Cl$_2$) afforded the title compound (60 mg, 39%). TLC (silica, 1% methanol saturated with ammonia/9% methanol/CH$_2$Cl$_2$): R$_f$=0.29. HPLC (Method A): R$_t$=7.89. MS (ESI+): mass calculated for C$_{22}$H$_{16}$ClN$_3$O, 373.1, m/z found, 373.6 [M+H]$^+$. $^1$H NMR (500 MHz, CD$_3$OD): δ 8.10 (br s, 1H), 8.02 (d; J=8.5 Hz, 2H), 7.74 (br d, J=8.5 Hz, 1H), 7.58 (br s, 1H), 7.42 (d, J=8.5 Hz, 2H), 7.29 (d, J=8.7 Hz, 2H), 7.24 (d, J=8.7 Hz, 2H), 5.53 (s, 1H), 5.48 (s, 1H).

Example 42

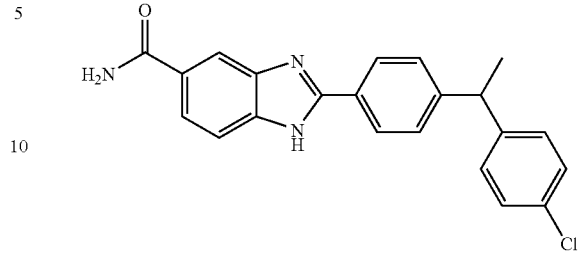

2-{4-[1-(4-Chloro-phenyl)-ethyl]-phenyl}-1H-benzoimidazole-5-carboxylic acid amide A flask containing a solution of 2-{4-[1-(4-chloro-phenyl)-vinyl]-phenyl}-1H-benzoimidazole-5-carboxylic acid amide (Example 41, 30 mg, 0.08 mmol) in 1:1 ethanol/ethyl acetate (6.0 mL) was charged with N$_2$ and evacuated (3×). Palladium on carbon (10 wt %) was added to the solution, and the flask was charged with H$_2$ and evacuated (3×), and then maintained at ~1 atm H$_2$ for 2.5 h. The flask was evacuated and then charged with N$_2$. The reaction mixture was filtered through a pad of Celite®, which was washed with ethanol (50 mL), ethyl acetate (50 mL) and then methanol (2×50 mL). The filtrate was concentrated under reduced pressure. Purification of the residue by chromatography (silica gel, 1% methanol saturated with ammonia/9% methanol/CH$_2$Cl$_2$) afforded the title compound (21 mg, 68%). TLC (silica, 1% methanol, saturated with ammonia/ 9% methanol/CH$_2$Cl$_2$): R$_f$=0.35. MS (ESI+): mass calculated for C$_{22}$H$_{18}$ClN$_3$O, 375.1, m/z found, 376.1 [M+H]$^+$. $^1$H NMR (500 MHz, CD$_3$OD): δ 8.16 (br s, 1H), 8.04 (d, J=8.4 Hz, 2H), 7.81 (d, J=8.3 Hz, 1H), 7.62 (br s, 1H), 7.43 (d, J=8.3 Hz, 2H), 7.30–7.26 (m, 4H), 4.27–4.24 (m, 1H), 1.67 (d, J=7.2 Hz, 3H).

Example 43

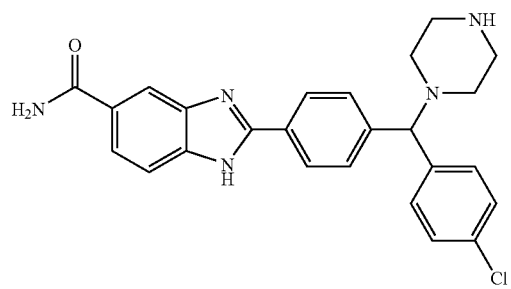

2-{4-[(4-Chloro-phenyl)-piperazin-1-yl-methyl]-phenyl}-1H-benzoimidazole-5-carboxylic acid amide To a suspension of 2-{4-[(4-chloro-phenyl)-hydroxy-methyl]-phenyl}-1H-benzoimidazole-5-carboxylic acid amide (Example 20, 20.0 mg, 0.05 mmol) in CH$_2$Cl$_2$ (10 mL) was added thionyl chloride (0.04 mL, 0.06 mmol), and the mixture was stirred at RT for 1 h. Solvent was removed under reduced pressure, and the residue was dried under high vacuum. The crude product was dissolved in acetonitrile (10 mL). Piperazine (21 mg, 0.24 mmol) was added, and the mixture was heated to reflux for 12 h. Solvent was removed under reduced pressure, and purification of the residue by chromatography (silica gel, 1% methanol saturated with ammonia/9% methanol/CH$_2$Cl$_2$) afforded 17 mg (77%) of the title compound. HPLC (Method A): R$_t$=6.44. MS (ESI−): mass calculated for C$_{25}$H$_{24}$ClN$_5$O, 445.2; m/z found, 444.6 [M−H]$^-$. $^1$H NMR (500 MHz, CD$_3$OD): δ 8.17 (br s, 1H), 8.09 (d, J=8.4 Hz, 2H), 7.82–7.80 (dd, J=8.5, 1.5 Hz, 1H), 7.66 (d, J=8.4 Hz, 2H), 7.63 (br s, 1H), 7.50 (d, J=8.5 Hz, 2H), 7.35 (d, J=8.5 Hz, 2H), 4.56 (s, 1H), 3.31–3.27 (m, 8H).

Example 44

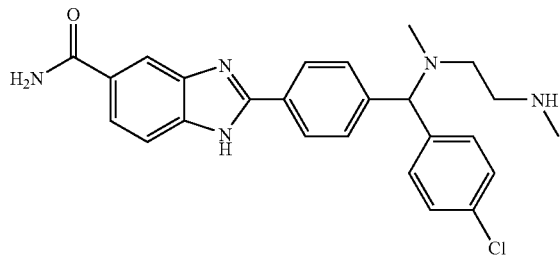

2-(4-{(4-Chloro-phenyl)-[methyl-(2-methylamino-ethyl)-amino]-methyl}-phenyl)-1H-benzoimidazole-5-carboxylic acid amide The title compound was prepared as described in Example 43 substituting N,N'-dimethyl-ethane-1,2-diamine for piperazine. HPLC (Method A): R$_t$=6.73. MS (ESI+): mass calculated for C$_{25}$H$_{26}$ClN$_5$O, 447.2; m/z found, 448.1 [M+H]$^+$. $^1$H NMR (500 MHz, CD$_3$OD): δ 8.07 (d, J=1.1 Hz, 1H), 7.96 (d, J=8.3 Hz, 2H), 7.72–7.70 (dd, J=8.5, 1.5 Hz, 1H), 7.54 (d, J=7.9 Hz, 2H), 7.52 (s, 1H), 7.38 (d, J=8.5 Hz, 2H), 7.20 (d, J=8.5 Hz, 2H), 4.40 (s, 1H), 2.63 (t, J=6.5 Hz, 2H), 2.43 (t, J=6.4 Hz, 2H), 2.26 (s, 3H), 2.10 (s, 3H).

Example 45

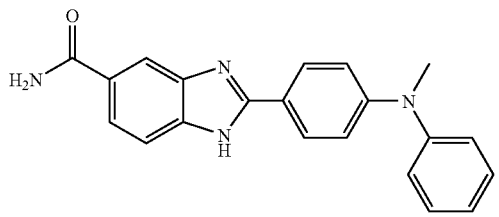

2-[4-(Methyl-phenyl-amino)-phenyl]-1H-benzoimidazole-5-carboxylic acid amide

A. (4-Bromo-phenyl)-methyl-phenyl-amine. To a cooled solution (0° C.) of methyl-diphenyl-amine (1.17 g, 6.4 mmol) in anhydrous CH$_2$Cl$_2$ (20 mL) was slowly added N-bromosuccinimide (1.15 g, 6.4 mmol) dissolved in CH$_2$Cl$_2$ (20 mL). The reaction mixture was stirred for 2 h at 0° C. and then refrigerated overnight. Solvent was removed under reduced pressure, and the residue was purified by chromatography (silica gel, 10% ethyl acetate/hexanes) to afford 1.38 g (82%) of the title compound. $^1$H NMR (500 MHz, CDCl$_3$): δ 7.32 (d, J=9.0 Hz, 2H), 7.29 (d, J=8.6 Hz, 2H), 7.06–7.04 (dd, J=8.7, 1.1 Hz, 2H), 7.03–7.02 (m, 1H), 6.83 (d, J=8.9 Hz, 2H), 3.28 (s, 3H).

B. 4-(Methyl-phenyl-amino)-benzaldehyde. This compound was prepared as described in Example 1 substituting (4-bromo-phenyl)-methyl-phenyl-amine (500 mg, 1.19 mmol) for 2-(4-bromo-phenyl)-2-phenyl-[1,3]dioxolane in Step B. Purification by chromatography (silica gel, 10% ethyl acetate/hexanes) afforded the title compound, 381 mg (94%). $^1$H NMR (500 MHz, CDCl$_3$): δ 9.76 (s, 1H), 7.69 (d, J=8.9 Hz, 2H), 7.43 (t, J=7.8 Hz, 2H), 7.28 (d, J=7.4 Hz, 1H), 7.24–7.22 (dd, J=8.4, 1.2 Hz, 2H), 6.78 (d, J=8.9 Hz, 2H), 3.39 (s, 3H).

C. 2-[4-(Methyl-phenyl-amino)-phenyl]-1H-benzoimidazole-5-carboxylic acid. This compound was prepared as described in Example 1 using 4-(methyl-phenyl-amino)-benzaldehyde (380 mg, 1.8 mmol) and 3,4-diamino-benzoic acid (273 mg, 1.8 mmol) in Step C. Crude product (528 mg, 85%) was used without further purification. HPLC (Method A): R$_t$=7.38. MS (ESI): mass calculated for C$_{21}$H$_{17}$N$_3$O$_2$, 343.1; m/z found, 344.1 [M+H]$^+$, 342.1, [M−H]$^-$.

D. 2-[4-(Methyl-phenyl-amino)-phenyl]-1H-benzoimidazole-5-carboxylic acid amide. This compound was prepared as described in Example 2 using 2-[4-(methyl-phenyl-amino)-phenyl]-1H-benzoimidazole-5-carboxylic acid (500 mg, 1.4 mmol) in Step D. Purification by chromatography (silica gel, 1% methanol saturated with ammonia/9% methanol/CH$_2$Cl$_2$) afforded 329 mg (66%) of the title compound. TLC (silica, 1% methanol saturated with ammonia/9% methanol/CH$_2$Cl$_2$): R$_f$=0.35. HPLC (Method A): R$_t$=7.07. MS (ESI): mass calculated for C$_{21}$H$_{18}$N$_4$O, 342.1, m/z found, 343.2 [M+H]$^+$, 341.2, [M−H]$^-$. $^1$H NMR (400 MHz, CD$_3$OD): δ 8.01 (s, 1H), 7.82 (d, J=8.9 Hz, 2H), 7.68–7.65 (dd, J=8.4, 1.6 Hz, 1H), 7.47 (br d, J=8.4 Hz, 1H), 7.31 (t, J=7.9 Hz, 2H), 7.14–7.12 (dd, J=8.6, 1.2 Hz, 2H), 7.09 (d, J=7.4 Hz, 1H), 6.83 (d, J=8.9 Hz, 2H), 3.27 (s, 3H).

Example 46

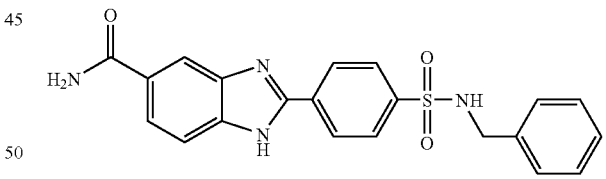

2-(4-Benzylsulfamoyl-phenyl)-1H-benzoimidazole-5-carboxylic acid amide

A. N-Benzyl-4-formyl-benzenesulfonamide. To a solution of 4-formyl-benzenesulfonyl chloride (200 mg, 0.978 mmol) and benzylamine (105 mg, 0.978 mmol) in anhydrous CH$_2$Cl$_2$ (3.3 mL) was added triethylamine (198 mg, 1.96 mmol) dropwise. The mixture was stirred at RT for 17 h, and then diluted with saturated aqueous NaHCO$_3$. The aqueous layer was extracted with ethyl acetate (×3), and the combined organic extracts were washed with brine and dried (MgSO$_4$). The solvent was removed under reduced pressure, and the residue was purified by chromatography (silica gel, 20% EtOAc/hexanes) to provide 197 mg (73%) of the title compound as a white solid. HPLC (Method C): $R_t$=6.01. MS (ESI): mass calculated for $C_{14}H_{13}NO_3S$, 275.1; m/z found, 274.2 [M−H]⁻. ¹H NMR (400 MHz, CDCl₃): δ 10.1 (s, 1H), 8.05–8.00 (m, 4H), 7.30–7.28 (m, 3H), 7.21 (dd, J=2.2, 9.6 Hz, 2H), 5.15 (bt, J=6.0 Hz, 1H), 4.23 (d, J=6.1 Hz, 2H). ¹³C NMR (100 MHz, CDCl₃): δ 191.3, 145.7, 139.2, 136.2, 130.6, 129.2, 128.5, 128.3, 128.2, 47.8.

B. 2-(4-Benzylsulfamoyl-phenyl)-1H-benzoimidazole-5-carboxylic acid amide. A solution of N-benzyl-4-formyl-benzenesulfonamide (137 mg, 0.497 mmol), 3,4-diamino-benzamide (75 mg, 0.497 mmol), and sodium metabisulfite (123 mg, 0.646 mmol) in DMF (5 mL) was heated at 60° C. for 14.5 h. After cooling to RT, the reaction mixture was poured into ice-cold saturated aqueous NH₄Cl (25 mL), and the precipitate was collected by vacuum filtration. Purification by chromatography (silica gel, 10% methanol saturated with NH₃/30% THF/60% CH₂Cl₂) afforded a purple solid, which was triturated with CH₂Cl₂ to provide 36 mg (18%) of the title compound as a gray powder. HPLC (Method C): $R_t$=4.55. MS (ESI): mass calculated for $C_{21}H_{18}N_4O_3S$, 406.1; m/z found, 407.3 [M+H]⁺. ¹H NMR (400 MHz, CD₃OD): δ 8.21 (d, J=8.6 Hz, 3H), 7.96 (d, J=8.6 Hz, 2H), 7.85 (dd, J=1.6, 8.5 Hz, 1H), 7.67 (d, J=8.5 Hz, 1H), 7.22–7.18 (m, 5H), 4.13 (s, 2H).

Example 47

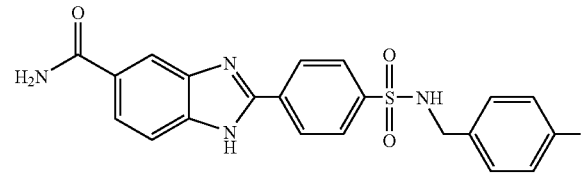

2-[4-(4-Methyl-benzylsulfamoyl)-phenyl]-1H-benzoimidazole-5-carboxylic acid amide A. 4-Formyl-N-(4-methyl-benzyl)-benzenesulfonamide. This compound was prepared as described in Example 46 substituting 4-methylbenzylamine (119 mg, 0.978 mmol) for benzylamine in Step A. The title compound was obtained as a white solid (162 mg, 57%).

B. 2-[4-(4-Methyl-benzylsulfamoyl)-phenyl]-1H-benzoimidazole-5-carboxylic acid amide. This compound was prepared as described in Example 46 substituting 4-formyl-N-(4-methyl-benzyl)-benzenesulfonamide (144 mg, 0.497 mmol) for N-benzyl-4-formyl-benzenesulfonamide in Step B. The title compound was obtained as a purple solid (38 mg, 18%). HPLC (Method C): $R_t$=4.73. MS (ESI): mass calculated for $C_{22}H_{20}N_4O_3S$, 420.1; m/z found, 421.4 [M+H]⁺. ¹H NMR (400 MHz, CD₃OD): δ 8.20 (d, J=8.4 Hz, 3H), 7.95 (d, J=8.4 Hz, 2H), 7.85 (d, J=8.3 Hz, 1H), 7.66 (bs, 1H), 7.07 (d, J=8.0 Hz, 2H), 7.01 (d, J=7.9 Hz, 2H), 4.08 (s, 2H).

Example 48

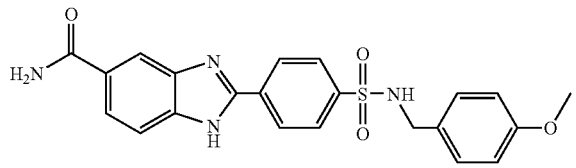

2-[4-(4-Methoxy-benzylsulfamoyl)-phenyl]-1H-benzoimidazole-5-carboxylic acid amide A. 4-Formyl-N-(4-methoxy-benzyl)-benzenesulfonamide. This compound was prepared as described in Example 46 Step A, substituting 4-methoxybenzylamine (335 mg, 2.44 mmol) for benzylamine. The title compound was obtained as a white solid (686 mg, 92%).

B. 2-[4-(4-Methoxy-benzylsulfamoyl)-phenyl]-1H-benzoimidazole-5-carboxylic acid amide. This compound was prepared as described in Example 46 Step B, substituting 4-formyl-N-(4-methoxy-benzyl)-benzenesulfonamide (202 mg, 0.66 mmol) for N-benzyl-4-formyl-benzenesulfonamide. The reaction was run at 90° C. instead of 60° C. The title compound was obtained as a yellow powder (90 mg, 31%). HPLC (Method C): $R_t$=4.48. MS (ESI): mass calculated for $C_{22}H_{20}N_4O_4S$, 436.1; m/z found, 437.1 [M+H]⁺. ¹H NMR (400 MHz, $C_2D_6SO$): δ 8.37 (d, J=8.5 Hz, 2H), 8.21 (m, 2H), 7.97 (d, J=8.5 Hz, 2H), 7.84 (d, J=9.1 Hz, 1H), 7.17 (d, J=8.7 Hz, 1H), 6.84 (d, J=8.7 Hz, 2H), 3.69 (s, 2H), 3.41 (s, 3H).

Example 49

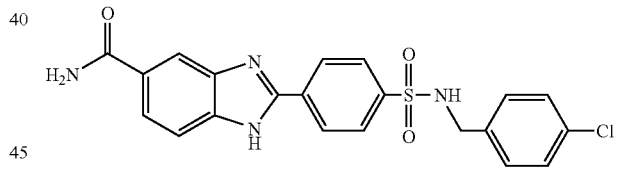

2-[4-(4-Chloro-benzylsulfamoyl)-phenyl]-1H-benzoimidazole-5-carboxylic acid amide A. N-(4-Chloro-benzyl)-4-formyl-benzenesulfonamide. This compound was prepared as described in Example 46 substituting 4-chlorobenzylamine (138 mg, 0.978 mmol) for benzylamine in Step A. The title compound was obtained as a white solid (236 mg, 78%).

B. 2-[4-(4-Chloro-benzylsulfamoyl)-phenyl]-1H-benzoimidazole-5-carboxylic acid amide. This compound was prepared as described in Example 46 substituting N-(4-chloro-benzyl)-4-formyl-benzenesulfonamide (155 mg, 0.50 mmol) for N-benzyl-4-formyl-benzenesulfonamide in Step B. The title compound was obtained as a brown powder (30 mg, 14%). HPLC (Method C): $R_t$=4.78. MS (ESI): mass calculated for $C_{21}H_{17}ClN_4O_3S$, 440.1; m/z found, 441.3 [M+H]⁺. ¹H NMR (400 MHz, CD₃OD): δ 8.13–8.11 (m, 3H), 7.86 (d, J=8.5 Hz, 2H), 7.75 (dd, J=1.6, 8.5 Hz, 1H), 7.58 (d, J=8.5 Hz, 1H), 7.10 (s, 4H), 4.01 (s, 2H).

Example 50

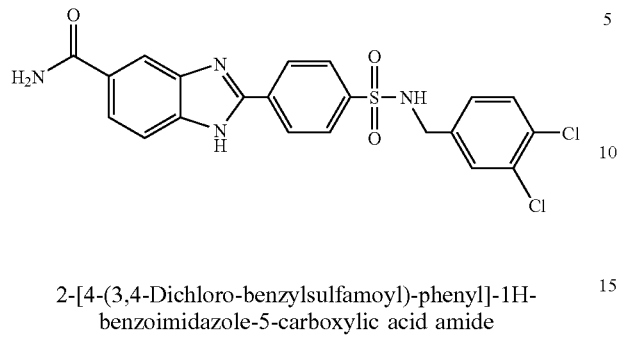

2-[4-(3,4-Dichloro-benzylsulfamoyl)-phenyl]-1H-benzoimidazole-5-carboxylic acid amide A. N-(3,4-Dichloro-benzyl)-4-formyl-benzenesulfonamide. This compound was prepared as described in Example 46 substituting 3,4-dichlorobenzylamine (172 mg, 0.978 mmol) for benzylamine in Step A. The title compound was obtained as a white solid, 216 mg (64%).

B. 2-[4-(3,4-Dichloro-benzylsulfamoyl)-phenyl]-1H-benzoimidazole-5-carboxylic acid amide. This compound was prepared as described in Example 46 substituting N-(3,4-dichloro-benzyl)-4-formyl-benzenesulfonamide (171 mg, 0.497 mmol) for N-benzyl-4-formyl-benzenesulfonamide in Step B. The title compound was obtained as a gray powder (59 mg, 25%). HPLC (Method C): $R_t$=4.91. MS (ESI): mass calculated for $C_{21}H_{16}C_{12}N_4O_3S$, 474.0; m/z found, 475.3 [M+H]$^+$. $^1$H NMR (400 MHz, CD$_3$OD): δ 8.24–8.22 (m, 3H), 7.95 (d, J=8.5 Hz, 2H), 7.86 (d, J=9.3 Hz, 1H), 7.69 (d, J=8.5 Hz, 1H), 7.37–7.32 (m, 2H), 7.16 (d, J=2.0 Hz, 1H), 4.14 (s, 2H).

Example 51

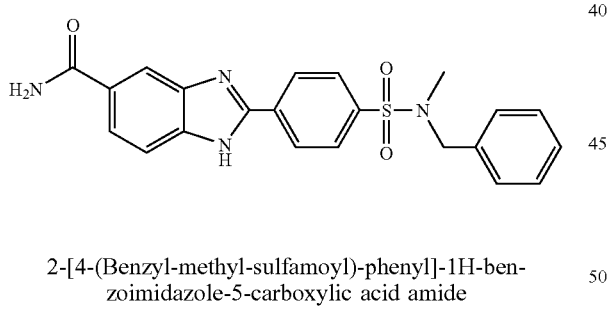

2-[4-(Benzyl-methyl-sulfamoyl)-phenyl]-1H-benzoimidazole-5-carboxylic acid amide A. N-Benzyl-4-formyl-N-methyl-benzenesulfonamide. This compound was prepared as described in Example 46, Step A, substituting N-methylbenzylamine (296 mg, 2.44 mmol) for benzylamine. The title compound was obtained as a white solid (675 mg, 96%).

B. 2-[4-(Benzyl-methyl-sulfamoyl)-phenyl]-1H-benzoimidazole-5-carboxylic acid amide. This compound was prepared as described in Example 46 Step B, substituting N-benzyl-4-formyl-N-methyl-benzenesulfonamide (171 mg, 0.497 mmol) for N-benzyl-4-formyl-benzenesulfonamide. The reaction was run at 90° C. instead of 60° C. The title compound was obtained as an off-white powder (37 mg, 13%). HPLC (Method C): $R_t$=4.84. MS (ESI): mass calculated for $C_{22}H_{20}N_4O_3S$, 420.1; m/z found, 421.1 [M+H]$^+$. $^1$H NMR (400 MHz, C$_2$D$_6$SO): δ 8.47 (d, J=8.5 Hz, 2H), 8.23 (bs, 1H), 8.07 (d, J=8.5 Hz, 3H), 7.85 (d, J=8.5 Hz, 1H), 7.69 (d, J=8.5 Hz, 1H), 7.39–7.32 (m, 5H), 4.22 (s, 2H), 2.61 (s, 3H).

Example 52

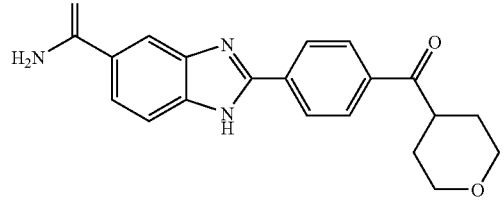

2-[4-(Tetrahydro-pyran-4-carbonyl)-phenyl]-1H-benzoimidazole-5-carboxylic acid amide The title compound was prepared as described in Example 4 substituting tetrahydro-pyran-4-carbaldehyde for 4-chloro-benzaldehyde in Step A. TLC (silica, 1% methanol saturated with ammonia/9% methanol/CH$_2$Cl$_2$): $R_f$=0.27. HPLC (Method A): $R_t$6.27. MS (ESI+): mass calculated for $C_{20}H_{19}N_3O_3$, 349.1; m/z found, 350.1 [M+H]$^+$. $^1$H NMR (500 MHz, CD$_3$OD): δ 8.17 (d, J=8.4 Hz, 3H), 8.10 (d, J=8.4 Hz, 2H), 7.82–7.80 (dd, J=8.4, 1.3 Hz, 1H), 7.63 (br d, J=8.1 Hz, 1H), 4.00–3.97 (m, 2H), 3.68–3.58 (m, 3H), 1.79–1.70 (m, 4H).

Example 53

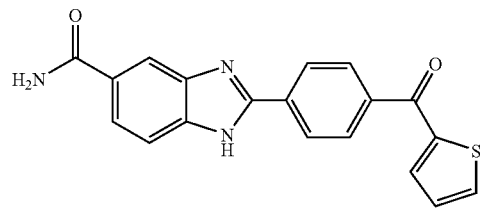

2-[4-(Thiophene-2-carbonyl)-phenyl]-1H-benzoimidazole-5-carboxylic acid amide

The title compound was prepared as described in Example 4 substituting thiophene-2-carbaldehyde for 4-chloro-benzaldehyde in Step A. TLC (silica, 1% methanol saturated with ammonia/9% methanol/CH$_2$Cl$_2$): $R_f$=0.26. HPLC (Method A): $R_t$=6.90. MS (ESI+): mass calculated for $C_{19}H_{13}N_3O_2S$, 347.0; m/z found, 348.0 [M+H]$^+$. $^1$H NMR (500 MHz, CD$_3$OD): δ 8.17 (d, J=8.4 Hz, 2H), 8.12 (br s, 1H), 7.92 (d, J=8.4 Hz, 2H), 7.87–7.86 (dd, J=5.0, 1.0 Hz, 1H), 7.75 (d, J=8.3 Hz, 1H), 7.68–7.67 (dd, J=3.8, 1.0 Hz, 1H), 7.58 (br s, 1H), 7.18–7.16 (dd, J=4.9, 3.8 Hz, 1H).

Example 54

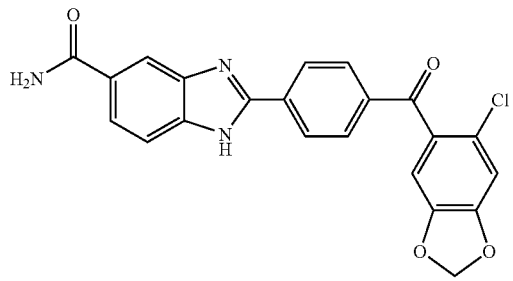

2-[4-(6-Chloro-benzo[1,3]dioxole-5-carbonyl)-phenyl]-1H-benzoimidazole-5-carboxylic acid amide The title compound was prepared as described in Example 4 substituting 6-chloro-benzo[1,3]dioxole-5-carbaldehyde for 4-chloro-benzaldehyde in Step A. TLC (silica, 1% methanol saturated with ammonia/9% methanol/$CH_2Cl_2$): $R_f$=0.37. HPLC (Method A): $R_t$=7.47. MS (ESI+): mass calculated for $C_{22}H_{14}ClN_3O_4$, 419.1; m/z found, 420.2, 422.2 [M+H]$^+$. $^1$H NMR (500 MHz, $CD_3OD$): δ 8.15 (d, J=8.5 Hz, 2H), 8.14 (br s, 1H), 7.85 (d, J=8.6 Hz, 1H), 7.75 (d, J=8.4 Hz, 1H), 7.59 (br s, 1H), 6.93 (s, 1H), 6.86 (s, 1H), 6.02 (s, 2H).

Example 56

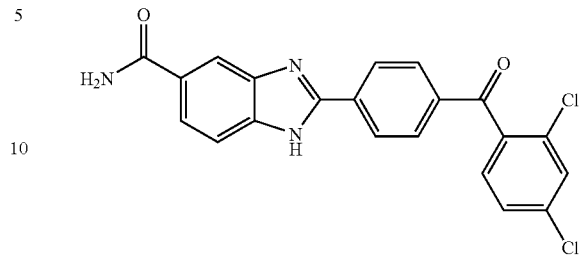

2-[4-(2,4-Dichloro-benzoyl)-phenyl]-1H-benzoimidazole-5-carboxylic acid amide

The title compound was prepared as described in Example 4 substituting 2,4-dichloro-benzaldehyde for 4-chloro-benzaldehyde in Step A. TLC (silica, 1% methanol saturated with ammonia/9% methanol/$CH_2Cl_2$): $R_f$=0.28. HPLC (Method A): $R_t$=7.91. MS (ESI+): mass calculated for $C_{21}H_{13}Cl_2N_3O_2$, 409.0; m/z found, 410.1, 412.2 [M+H]$^+$. $^1$H NMR (500 MHz, $CD_3OD$): δ 8.17 (d, J=8.6 Hz, 2H), 8.12 (br s, 1H), 7.85 (d, J=8.6 Hz, 2H), 7.76–7.74 (dd, J=8.5, 1.5 Hz, 1H), 7.59 (br d, J=8.3 Hz, 1H), 7.56 (d, J=1.9 Hz, 1H), 7.45–7.43 (dd, J=8.2, 1.9 Hz, 1H), 7.40 (d, J=8.2 Hz, 1H).

Example 55

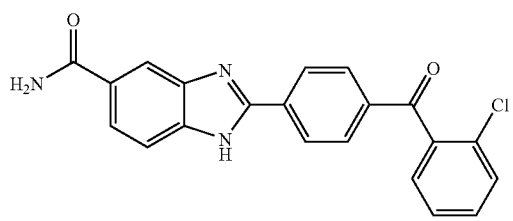

2-[4-(2-Chloro-benzoyl)-phenyl]-1H-benzoimidazole-5-carboxylic acid amide

The title compound was prepared as described in Example 4 substituting 2-chloro-benzaldehyde for 4-chloro-benzaldehyde in Step A. TLC (silica, 1% methanol saturated with ammonia/9% methanol/$CH_2Cl_2$): $R_f$=0.31. HPLC (Method A): $R_t$=7.44. MS (ESI+): mass calculated for $C_{21}H_{14}ClN_3O_2$, 375.1; m/z found, 376.3 [M+H]$^+$. $^1$H NMR (500 MHz, $CD_3OD$): δ 8.16 (d, J=8.4 Hz, 2H), 8.11 (br s, 1H), 7.85 (d, J=8.6 Hz, 2H), 7.75 (br s, 1H), 7.59 (br s, 1H), 7.49–7.47 (m, 2H), 7.46–7.35 (m, 2H).

Example 57

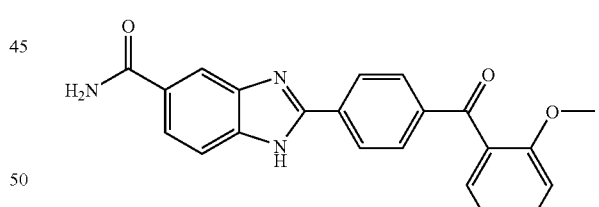

2-[4-(2-Methoxy-benzoyl)-phenyl]-1H-benzoimidazole-5-carboxylic acid amide

The title compound was prepared as described in Example 4 substituting 2-methoxy-benzaldehyde for 4-chloro-benzaldehyde in Step A. HPLC (Method A): $R_t$=7.16. MS (ESI+): mass calculated for $C_{22}H_{17}N_3O_3$, 371.1; m/z found, 372.3 [M+H]$^+$. $^1$H NMR (500 MHz, $CD_3OD$): δ 8.09 (br s, 1H), 8.06 (d, J=8.6 Hz, 2H), 7.75 (d, J=8.6 Hz, 2H), 7.73–7.71 (dd, J=8.5, 1.6 Hz, 1H), 7.54 (d, J=8.4 Hz, 1H), 7.45–7.42 (m, 1H), 7.27–7.26 (dd, J=7.5, 1.7 Hz, 1H), 7.02 (d, J=8.3 Hz, 1H), 6.99–6.96 (m, 1H), 3.59 (s, 3H).

Example 58

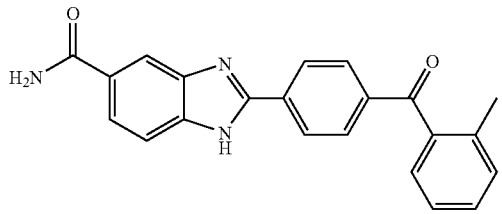

2-[4-(2-Methyl-benzoyl)-phenyl]-1H-benzoimidazole-5-carboxylic acid amide

The title compound was prepared as described in Example 4 substituting 2-methyl-benzaldehyde for 4-chloro-benzaldehyde in Step A. TLC (silica, 1% methanol saturated with ammonia/9% methanol/CH$_2$Cl$_2$): R$_f$=0.26. HPLC (Method A): R$_t$=7.43. MS (ESI+): mass calculated for C$_{22}$H$_{17}$N$_3$O$_2$, 355.1; m/z found, 356.3 [M+H]$^+$. $^1$H NMR (500 MHz, CD$_3$OD): δ 8.15 (d, J=8.6 Hz, 2H), 8.14 (br s, 1H), 7.84 (d, J=8.6 Hz, 2H), 7.76–7.74 (dd, J=8.5, 1.3 Hz, 1H), 7.60 (br s, 1H), 7.39–7.36 (m, 1H), 7.29–7.22 (m, 3H), 2.23 (s, 3H).

Example 59

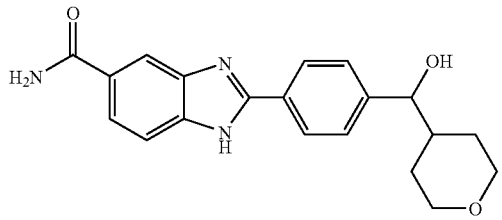

2-{4-[Hydroxy-(tetrahydro-pyran-4-yl)-methyl]-phenyl}-1H-benzoimidazole-5-carboxylic acid amide The title compound was prepared as described in Example 19 from 2-[4-(tetrahydro-pyran-4-carbonyl)-phenyl]-1H-benzoimidazole-5-carboxylic acid amide (Example 52, 50 mg, 0.14 mmol). Purification by chromatography (silica gel, 1% methanol saturated with ammonia/9% methanol/CH$_2$Cl$_2$) afforded 38 mg (76%) of the title compound. TLC (silica, 1% methanol saturated with ammonia/9% methanol/CH$_2$Cl$_2$): R$_f$=0.06. HPLC (Method A): R$_t$=5.76. MS (ESI+): mass calculated for C$_{20}$H$_{21}$N$_3$O$_3$, 351.1; m/z found, 352.2 [M+H]$^+$. $^1$H NMR (500 MHz, CD$_3$OD): δ 8.08 (br s, 1H), 7.99 (d, J=8.2 Hz, 2H), 7.72 (d, J=8.3 Hz, 1H), 7.54 (br s, 1H), 7.43 (d, J=8.3 Hz, 2H), 4.33 (d, J=7.0 Hz, 1H), 3.89–3.86 (dd, J=11.4, 3.8 Hz, 1H), 3.79–3.76 (dd, J=11.3, 3.3 Hz, 1H), 3.31–3.26 (m, 2H), 1.83–1.74 (m, 2H), 1.40–1.25 (m, 2H), 1.15–1.12 (d, J=12.6 Hz, 1H).

Example 60

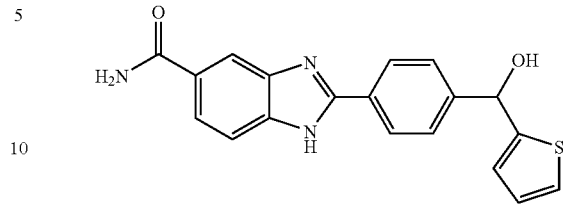

2-[4-(Hydroxy-thiophen-2-yl-methyl)-phenyl]-1H-benzoimidazole-5-carboxylic acid amide The title compound was prepared as described in Example 19 from 2-[4-(thiophene-2-carbonyl)-phenyl]-1H-benzoimidazole-5-carboxylic acid amide (Example 53, 19 mg, 0.04 mmol). Purification by chromatography (silica gel, 1% methanol saturated with ammonia/9% methanol/CH$_2$Cl$_2$) afforded 11 mg (78%) of the title compound. TLC (silica, 1% methanol saturated with ammonia/9% methanol/CH$_2$Cl$_2$): R$_f$=0.17. HPLC (Method A): R$_t$=6.48. MS (ESI+): mass calculated for C$_{19}$H$_5$N$_3$O$_2$S, 349.1; m/z found, 350.0 [M+H]$^+$. $^1$H NMR (500 MHz, CD$_3$OD): δ 8.07 (br s, 1H), 8.01 (d, J=8.3 Hz, 2H), 7.72 (br d, J=7.9 Hz, 1H), 7.54 (d, J=8.3 Hz, 3H), 7.23–7.22 (dd, J=3.9, 2.4 Hz, 1H), 6.85–6.83 (m, 3H).

Example 61

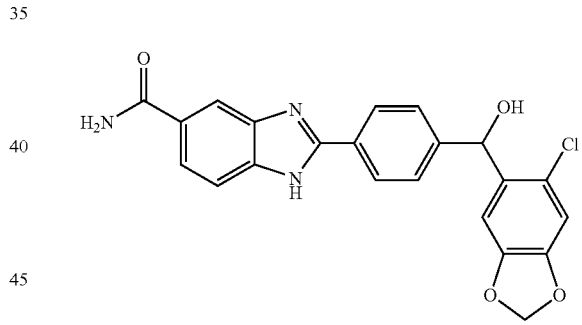

2-{4-[(6-Chloro-benzo[1,3]dioxol-5-yl)-hydroxy-methyl]-phenyl}-1H-benzoimidazole-5-carboxylic acid amide The title compound was prepared as described in Example 19 from 2-[4-(6-chloro-benzo[1,3]dioxole-5-carbonyl)-phenyl]-1H-benzoimidazole-5-carboxylic acid amide (Example 54, 150 mg, 0.35 mmol). Purification by chromatography (silica gel, 1% methanol saturated with ammonia/9% methanol/CH$_2$Cl$_2$) afforded 136 mg (91%) of the title compound. TLC (silica, 1% methanol saturated with ammonia/9% methanol/CH$_2$Cl$_2$): R$_f$=0.21. HPLC (Method A): R$_t$=6.88. MS (ESI+): mass calculated for C$_{22}$H$_{16}$ClN$_3$O$_4$, 421.1; m/z found, 422.2, 424.2 [M+H]$^+$. $^1$H ,NMR (500 MHz, CD$_3$OD): δ 8.06 (br s, 1H), 7.96 (d, J=8.4 Hz, 2H), 7.71 (dd, J=8.4, 1.4 Hz, 1H), 7.53 (br s, 1H), 7.45 (d, J=8.2 Hz, 2H), 6.97 (s, 1), 6.75 (s, 1H), 6.06 (s, 1H), 5.88 (s, 1H), 5.85 (s, 1H).

Example 62

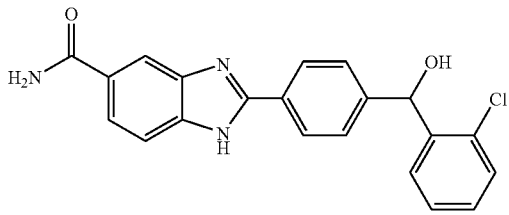

2-{4-[(2-Chloro-phenyl)-hydroxy-methyl]-phenyl}-1H-benzoimidazole-5-carboxylic acid amide The title compound was prepared as described in Example 19 from 2-[4-(2-Chloro-benzoyl)-phenyl]-1H-benzoimidazole-5-carboxylic acid amide (Example 55, 125 mg, 0.3 mmol). Purification by chromatography (silica gel, 1% methanol saturated with ammonia/9% methanol/$CH_2Cl_2$) afforded 114 mg (91%) of the title compound. TLC (silica, 1% methanol saturated with ammonia/9% methanol/$CH_2Cl_2$): $R_f$=0.19. HPLC (Method A): $R_t$=6.83. MS (ESI+): mass calculated for $C_{21}H_{16}ClN_3O_2$, 377.1; m/z found, 378.3, 380.2 $[M+H]^+$. $^1$H NMR (500 MHz, $CD_3OD$): δ 8.06 (br s, 1H), 7.95 (d, J=8.2 Hz, 2H), 7.70 (d, J=8.3 Hz, 1H), 7.59 (d, J=7.8 Hz, 1H), 7.52 (br s, 1H), 7.45 (d, J=8.2 Hz, 2H), 7.27–7.24 (m, 2H), 7.17–7.14 (m, 1H), 6.14 (s, 1H).

Example 63

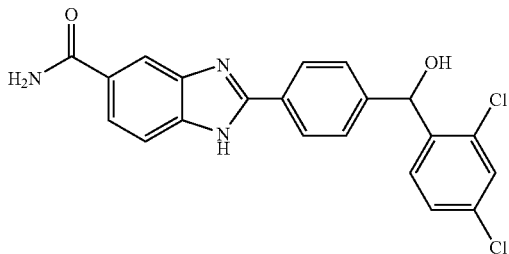

2-{4-[(2,4-Dichloro-phenyl)-hydroxy-methyl]-phenyl}-1H-benzoimidazole-5-carboxylic acid amide The title compound was prepared as described in Example 19 from 2-[4-(2,4-dichloro-benzoyl)-phenyl]-1H-benzoimidazole-5-carboxylic acid amide (Example 56, 75 mg, 0.16 mmol). Purification by chromatography (silica gel, 1% methanol saturated with ammonia/9% methanol/$CH_2Cl_2$) afforded 61 mg (81%) of the title compound. TLC (silica, 1% methanol saturated with ammonia/9% methanol/$CH_2Cl_2$): $R_f$=0.27. HPLC (Method A): $R_t$=7.24. MS (ESI+): mass calculated for $C_{21}H_{15}Cl_2N_3O_2$, 411.1; m/z found, 412.2, 414.2 $[M+H]^+$. $^1$H NMR (500 MHz, $CD_3OD$): δ 8.07 (br s, 1H), 7.96 (d, J=8.4 Hz, 2H), 7.71–7.69 (dd, J=8.5, 1.6 Hz, 1H), 7.59 (d, J=8.5 Hz, 1H), 7.53 (br d, J=8.3 Hz, 1H), 7.44 (d, J=8.3 Hz, 2H), 7.32 (d, J=2.1 Hz, 1H), 7.29–7.27 (dd, 2=8.5, 2.1 Hz, 1H), 6.07 (s, 1H).

Example 64

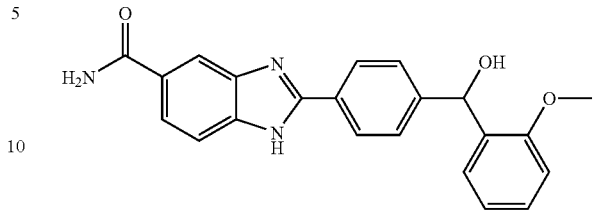

2-{4-[Hydroxy-(2-methoxy-phenyl)-methyl]-phenyl}-1H-benzoimidazole-5-carboxylic acid amide The title compound was prepared as described in Example 19 from 2-[4-(2-methoxy-benzoyl)-phenyl]-1H-benzoimidazole-5-carboxylic acid amide (Example 57, 120 mg, 0.3 mmol). Purification by chromatography (silica gel, 1% methanol saturated with ammonia/9% methanol/$CH_2Cl_2$) afforded 101 mg (84%) of the title compound. TLC (silica, 1% methanol saturated with ammonia/9% methanol/$CH_2Cl_2$): $R_f$=0.13 HPLC (Method A): $R_t$=6.69. MS (ESI+): mass calculated for $C_{22}H_{19}N_3O_3$, 373.1; m/z found, 374.3 $[M+H]^+$. $^1$H NMR (500 MHz, $CD_3OD$): δ 8.07 (br s, 1H), 7.93 (d, J=8.3 Hz, 2H), 7.70 (br d, J=8.2 Hz, 1H), 7.52 (br s, 1H), 7.45 (d, J=8.3 Hz, 2H), 7.40–7.38 (dd, J=7.6, 1.5 Hz, 1H), 7.16–7.13 (m, 1H), 6.88–6.84 (m, 2H), 6.10 (s, 1H), 3.70 (s, 3H).

Example 65

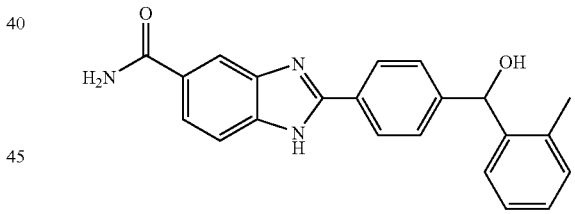

2-[4-(Hydroxy-o-tolyl-methyl)-phenyl]-1H-benzoimidazole-5-carboxylic acid amide

The title compound was prepared as described in Example 19 from 2-[4-(2-methyl-benzoyl)-phenyl]-1H-benzoimidazole-5-carboxylic acid amide (Example 58, 100 mg, 0.28 mmol). Purification by chromatography (silica gel, 1% methanol saturated with ammonia/9% methanol/$CH_2Cl_2$) afforded 78 mg (78%) of the title compound. TLC (silica, 1% methanol saturated with ammonia/9% methanol/$CH_2Cl_2$): $R_f$=0.16. HPLC (Method A): $R_t$=6.74. MS (ESI+): mass calculated for $C_{22}H_{19}N_3O_2$, 357.1; m/z found, 358.3 $[M+H]^+$. $^1$H NMR (500 MHz, $CD_3OD$): δ 8.06 (br s, 1H), 7.95 (d, J=8.3 Hz, 2H), 7.70 (d, J=8.3 Hz, 1H), 7.52 (br s, 1H), 7.39 (d, J=8.2 Hz, 2H), 7.35 (d, J=7.4 Hz, 1H), 7.11–7.02 (m, 3H), 5.93 (s, 1H), 2.17 (s, 3H).

Example 66

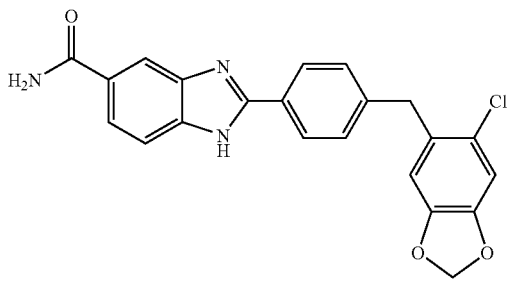

2-[4-(6-Chloro-benzo[1,3]dioxol-5-ylmethyl)-phenyl]-1H-benzoimidazole-5-carboxylic acid amide The title compound was prepared as described in Example 35 from 2-{4-[(6-chloro-benzo[1,3]dioxol-5-yl)-hydroxymethyl]-phenyl}-1H-benzoimidazole-5-carboxylic acid amide (Example 61, 53 mg, 0.12 mmol). Purification by chromatography (silica gel, 1% methanol saturated with ammonia/9% methanol/$CH_2Cl_2$) afforded 34 mg (68%) of the title compound. TLC (silica, 1% methanol saturated with ammonia/9% methanol/$CH_2Cl_2$): $R_f$=0.38. HPLC (Method A): $R_t$=7.28. MS (ESI+): mass calculated for $C_{22}H_{16}ClN_3O_3$, 405.1, m/z found, 406.2, 408.3 [M+H]$^+$. $^1$H NMR (500 MHz, $CD_3OD$): δ 8.18 (br s, 1H), 7.95 (d, J=8.3 Hz, 2H), 7.93 (d, J=1.6 Hz, 1H), 7.70 (d, J=8.6 Hz, 1H), 7.42 (d, J=8.4 Hz, 2H), 6.82 (s, 1H), 6.74 (s, 1H), 5.88 (s, 2H), 4.06 (s, 2H).

Example 67

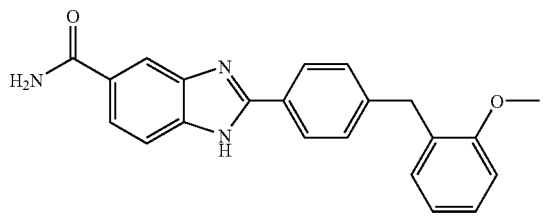

2-[4-(2-Methoxy-benzyl)-phenyl]-1H-benzoimidazole-5-carboxylic acid amide

The title compound was prepared as described in Example 35 from 2-{4-[hydroxy-(2-methoxy-phenyl)-methyl]-phenyl}-1H-benzoimidazole-5-carboxylic acid amide (Example 64, 30 mg, 0.08 mmol). Purification by chromatography (silica gel, 1% methanol saturated with ammonia/9% methanol/$CH_2Cl_2$) afforded 20 mg (71%) of the title compound. HPLC (Method A): $R_t$=7.46. MS (ESI+): mass calculated for $C_{22}H_{19}N_3O_2$, 357.1, m/z found, 358.3 [M+H]$^+$. $^1$H NMR (500 MHz, $CD_3OD$): δ 8.06 (br s, 1H), 7.88 (d, J=8.4 Hz, 2H), 7.71–7.69 (dd, J=8.5, 1.7 Hz, 1H), 7.51 (d, J=8.4 Hz, 1H), 7.26 (d, J=8.4 Hz, 2H), 7.12–7.08 (td, J=8.2, 1.7 Hz, 1H), 7.05–7.03 (dd, J=7.4, 1.6 Hz, 1H), 6.84 (d, J=8.2 Hz, 1H), 6.79–6.76 (td, J=7.4, 1.5 Hz, 1H), 3.91 (s, 2H), 3.69 (s, 3H).

Example 68

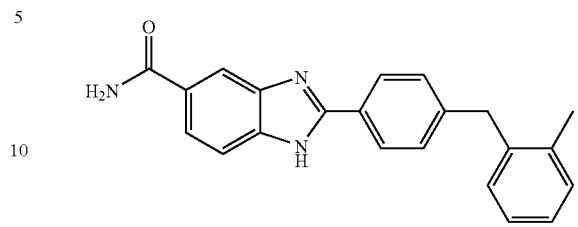

2-[4-(2-Methyl-benzyl)-phenyl]-1H-benzoimidazole-5-carboxylic acid amide

The title compound was prepared as described in Example 35 from 2-[4-(hydroxy-o-tolyl-methyl)-phenyl]-1H-benzoimidazole-5-carboxylic acid amide (Example 65, 11 mg, 0.03 mmol). Product was isolated as a TFA salt (7 mg, 70%). HPLC (Method A): $R_t$=7.93. MS (ESI+): mass calculated for $C_{22}H_{19}N_3O$, 341.1, m/z found, 342.3 [M+H]$^+$. $^1$H NMR (500 MHz, $CD_3OD$): δ 8.06 (br s, 1H), 7.91 (d, J=8.3 Hz, 2H), 7.71 (d, J=8.2 Hz, 1H), 7.53 (br s, 1H), 7.20 (d, J=8.4 Hz, 2H), 7.08–7.02 (m, 4H), 3.99 (s, 2H), 2.13 (S, 3H).

Example 69

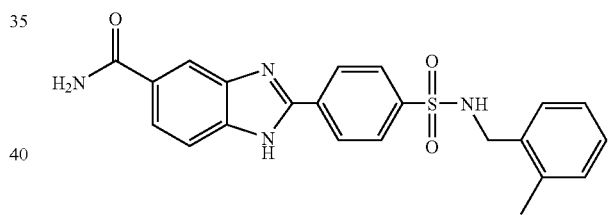

2-[4-(2-Methyl-benzylsulfamoyl)-phenyl]-1H-benzoimidazole-5-carboxylic acid amide A. 4-Formyl-N-(2-methyl-benzyl)-benzenesulfonamide. This compound was prepared as described in Example 46 substituting 2-methylbenzylamine (119 mg, 0.978 mmol) for benzylamine in Step A. The title compound was obtained as a white solid, 260 mg (92%).

B. 2-[4-(2-Methyl-benzylsulfamoyl)-phenyl]-1H-benzoimidazole-5-carboxylic acid amide. This compound was prepared as described in Example 46 substituting 4-formyl-N-(2-methyl-benzyl)-benzenesulfonamide (172 mg, 0.662 mmol) for N-benzyl-4-formyl-benzenesulfonamide in Step B. The title compound was obtained as a beige solid, 81 mg (29%). HPLC (Method C): $R_t$=4.61. MS (ESI): mass calculated for $C_{22}H_{20}N_4O_3S$, 420.1; m/z found, 421.1 [M+H]$^+$. $^1$H NMR (400 MHz, DMSO-$d_6$): δ 8.41 (d, J=8.4 Hz, 2H), 8.11 (bm, 3H), 7.86 (d, J=8.1 Hz, 1H), 7.69 (bs, 1H), 7.37 (bs, 1H), 7.23 (d, J=6.8 Hz, 1H), 7.16 (m, 3H), 4.03 (s, 2H), 2.24 (s, 3H).

Example 70

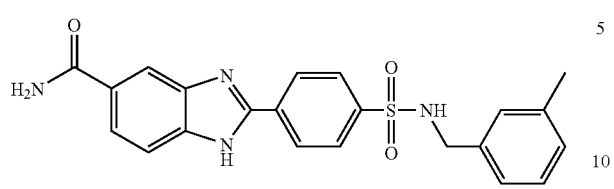

2-[4-(3-Methyl-benzylsulfamoyl)-phenyl]-1H-benzoimidazole-5-carboxylic acid amide A. 4-Formyl-N-(3-methyl-benzyl)-benzenesulfonamide. This compound was prepared as described in Example 46 substituting 3-methylbenzylamine (119 mg, 0.978 mmol) for benzylamine in Step A. The title compound was obtained as a white solid, 250 mg (88%).

B. 2-[4-(3-Methyl-benzylsulfamoyl)-phenyl]-1H-benzoimidazole-5-carboxylic acid amide. This compound was prepared as described in Example 46 substituting 4-formyl-N-(3-methyl-benzyl)-benzenesulfonamide (172 mg, 0.662 mmol) for N-benzyl-4-formyl-benzenesulfonamide in Step B. The title compound was obtained as a beige solid, 72 mg (26%). HPLC (Method C): $R_f$=4.63. MS (ESI): mass calculated for $C_{22}H_{20}N_4O_3S$, 420.1; m/z found, 421.1 [M+H]$^+$. $^1$H NMR (400 MHz, DMSO-d$_6$): δ 8.36 (d, J=8.5 Hz, 2H), 8.04 (bs, 1H), 7.96 (d, J=8.5 Hz, 2H), 7.83 (dd, J=8.5, 1.4 Hz, 1H), 7.67 (d, J=8.5 Hz, 1H), 7.33 (bs, 1H), 7.16 (t, J=7.7 Hz, 1H), 7.03 (bm, 3H), 4.03 (s, 2H), 2.21 (s, 3H).

Example 71

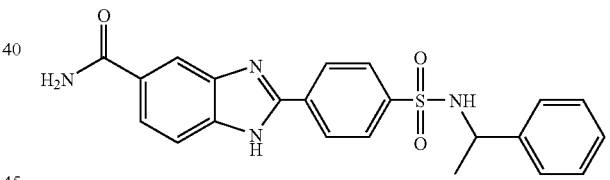

2-[4-(1,3-Dihydro-isoindole-2-sulfonyl)-phenyl]-1H-benzoimidazole-5-carboxylic acid amide A. 4-(1,3-Dihydro-isoindole-2-sulfonyl)-benzaldehyde. This compound was prepared as described in Example 46 substituting isoindoline (117 mg, 0.978 mmol) for benzylamine in Step A. The title compound was obtained as a white solid, 253 mg (90%).

B. 2-[4-(1,3-Dihydro-isoindole-2-sulfonyl)-phenyl]-1H-benzoimidazole-5-carboxylic acid amide. This compound was prepared as described in Example 46 substituting 4-(1,3-dihydro-isoindole-2-sulfonyl)-benzaldehyde (190 mg, 0.662 mmol) for N-benzyl-4-formyl-benzenesulfonamide in Step B. The title compound was obtained as a yellow powder, 122 mg (44%). HPLC (Method C): $R_f$=4.69. MS (ESI): mass calculated for $C_{22}H_{18}N_4O_3S$, 418.5; m/z found, 419.1 [M+H]$^+$. $^1$H NMR (400 MHz, DMSO-d$_6$): δ 8.41 (d, J=8.5 Hz, 2H), 8.07 (d, J=8.5 Hz, 1H), 8.03 (bs, 1H), 7.81 (bd, J=8.1 Hz, 1H), 7.65 (bs, 1H), 7.33 (bs, 1H), 7.25 (m, 5H), 4.65 (s, 4H).

Example 72

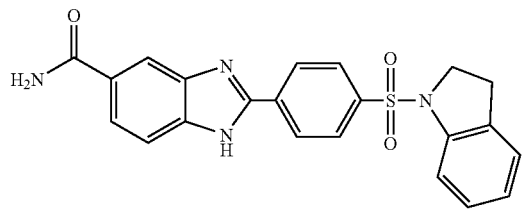

2-[4-(2,3-Dihydro-indole-1-sulfonyl)-phenyl]-1H-benzoimidazole-5-carboxylic acid amide A. 4-(2,3-Dihydro-indole-2-sulfonyl)-benzaldehyde. This compound was prepared as described in Example 46 substituting indoline (117 mg, 0.978 mmol) for benzylamine in Step A. The title compound was obtained as a tan solid, 250 mg (89%).

B. 2-[4-(2,3-Dihydro-indole-2-sulfonyl)-phenyl]-1H-benzoimidazole-5-carboxylic acid amide. This compound was prepared as described in Example 46 substituting 4-(2,3-dihydro-indole-2-sulfonyl)-benzaldehyde (202 mg, 0.703 mmol) for N-benzyl-4-formyl-benzenesulfonamide in Step B. The title compound was obtained as a beige powder, 130 mg (44%). HPLC (Method C): $R_f$=4.80. MS (ESI): mass calculated for $C_{22}H_{18}N_4O_3S$, 418.5; m/z found, 419.1 [M+H]$^+$. $^1$H NMR (400 MHz, DMSO-d$_6$): δ 8.36 (d, J=8.2 Hz, 2H), 8.22 (s, 1H), 8.04 (m, 3H), 7.84 (d, J=8.4 Hz, 1H), 7.67 (d, J=8.4 Hz, 1H), 7.54 (d, J=8.0 Hz, 1H), 7.36 (s, 1H), 7.20 (m, 2H), 7.01 (m, 1H), 4.01 (t, J=8.2 Hz, 2H), 2.94 (t, J=8.1 Hz, 2H).

Example 73

(±)-2-[4-(1-Phenyl-ethylsulfamoyl)-phenyl]-1H-benzoimidazole-5-carboxylic acid amide A. (±) 4-Formyl-N-(1-phenyl-ethyl)-benzenesulfonamide. This compound was prepared as described in Example 46 substituting (±)-α-methylbenzylamine (119 mg, 0.978 mmol) for benzylamine in Step A. The title compound was obtained as a white solid, 223 mg (79%).

B. (±)-2-[4-(1-Phenyl-ethylsulfamoyl)-phenyl]-1H-benzoimidazole-5-carboxylic acid amide. This compound was prepared as described in Example 46 substituting (±) 4-Formyl-N-(1-phenyl-ethyl)-benzenesulfonamide (198 mg, 0.686 mmol) for N-benzyl-4-formyl-benzenesulfonamide in Step B. The title compound was obtained as a beige powder, 96 mg (33%). HPLC (Method C): $R_f$=4.49. MS (ESI): mass calculated for $C_{22}H_{20}N_4O_3S$, 420.5; m/z found, 421.1 [M+H]$^+$. $^1$H NMR (400 MHz, DMSO-d$_6$): δ 8.39 (d, J=8.2 Hz, 1H), 8.28 (d, J=8.5 Hz, 2H), 8.15 (bs, 1H), 7.86 (d, J=8.5 Hz, 3H), 7.75 (bs, 1H), 7.40 (bs, 1H), 7.19 (m, 5H), 4.46 (q, J=7.1 Hz, 1H), 1.28 (d, J=6.9 Hz, 3H).

Example 74

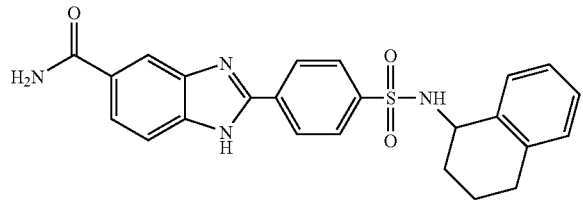

(±)-2-[4-(1,2,3,4-Tetrahydro-naphthalen-1-ylsulfamoyl)-phenyl]-1H-benzoimidazole-5-carboxylic acid amide A. (±) 4-Formyl-N-(1,2,3,4-tetrahydro-naphthalen-1-yl)-benzenesulfonamide. This compound was prepared as described in Example 46 substituting (±)-1,2,3,4-tetrahydro-naphthylamine (144 mg, 0.978 mmol) for benzylamine in Step A. The title compound was obtained as a white solid, 210 mg (68%).

B. (±)-2-[4-(1,2,3,4-Tetrahydro-naphthalen-1-ylsulfamoyl)-phenyl]-1H-benzoimidazole-5-carboxylic acid amide. This compound was prepared as described in Example 46 substituting (±) 4-formyl-N-(1,2,3,4-tetrahydro-naphthalen-1-yl)-benzenesulfonamide (209 mg, 0.662 mmol) for N-benzyl-4-formyl-benzenesulfonamide in Step B. The title compound was obtained as a beige powder, 94 mg (32%). HPLC (Method C): $R_f$=4.80. MS (ESI): mass calculated for $C_{24}H_{22}N_4O_3S$, 446.5; m/z found, 447.1 [M+H]$^+$. $^1$H NMR (400 MHz, DMSO-d$_6$): δ 8.43 (d, J=8.5 Hz, 2H), 8.24 (bm, 2H), 8.08 (d, J=8.5 Hz, 2H), 8.05 (m, 1H), 7.84 (d, J=8.4 Hz, 1H), 7.72 (bm, 1H), 7.34 (bs, 1H), 7.09 (m, 4H), 4.51 (bd, J=3.4 Hz, 1H), 2.65 (bm, 2H), 1.79 (bm, 1H), 1.61 (bm, 3H).

Example 75

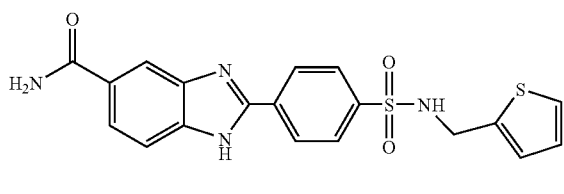

2-{4-[(Thiophen-2-ylmethyl)-sulfamoyl]-phenyl}-1H-benzoimidazole-5-carboxylic acid amide A. 4-Formyl-N-thiophen-2-ylmethyl-benzenesulfonamide. This compound was prepared as described in Example 46 substituting (2-aminomethyl)thiophene (111 mg, 0.978 mmol) for benzylamine in Step A. The title compound was obtained as a white solid, 201 mg (73%).

B. 2-{4-[(Thiophen-2-ylmethyl)-sulfamoyl]-phenyl}-1H-benzoimidazole-5-carboxylic acid amide. This compound was prepared as described in Example 46 substituting 4-formyl-N-thiophen-2-ylmethyl-benzenesulfonamide (186 mg, 0.662 mmol) for N-benzyl-4-formyl-benzenesulfonamide in Step B. The title compound was obtained as a beige powder, 114 mg (42%). HPLC (Method C): $R_f$=4.40. MS (ESI): mass calculated for $C_{19}H_{16}N_4O_3S_2$, 412.5; m/z found, 413.0 [M+H]$^+$. $^1$H NMR (400 MHz, DMSO-d$_6$): δ 8.39 (d, J=8.5 Hz, 2H), 8.30 (bs, 1H), 8.15 (bs, 1H), 7.99 (d, J=8.5 Hz, 2H), 7.85 (d, J=8.4 Hz, 1H), 7.67 (bm, 1H), 7.40 (dd, J=5.0, 1.3 Hz, 1H), 7.36 (bs, 1H), 6.94 (d, J=2.4 Hz, 1H), 6.91 (dd, J=5.0, 3.5 Hz, 1H), 4.29 (s, 2H).

Example 76

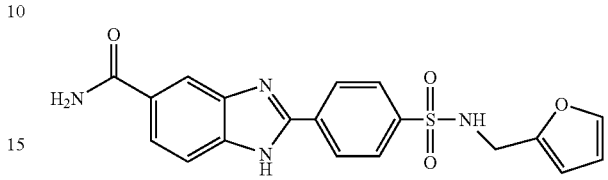

2-{4-[(Furan-2-ylmethyl)-sulfamoyl]-phenyl}-1H-benzoimidazole-5-carboxylic acid amide A. 4-Formyl-N-furan-2-ylmethyl-benzenesulfonamide. This compound was prepared as described in Example 46 substituting furfurylamine (95 mg, 0.978 mmol) for benzylamine in Step A. The title compound was obtained as a white solid, 203 mg (78%).

B. 2-{4-[(Furan-2-ylmethyl)-sulfamoyl]-phenyl}-1H-benzoimidazole-5-carboxylic acid amide. This compound was prepared as described in Example 46 substituting 4-formyl-N-furan-2-ylmethyl-benzenesulfonamide (176 mg, 0.662 mmol) for N-benzyl-4-formyl-benzenesulfonamide in Step B. The title compound was obtained as a beige powder, 118 mg (45%). HPLC (Method C): $R_f$=4.24. MS (ESI): mass calculated for $C_{19}H_{16}N_4O_4S$, 396.4; m/z found, 397.1 [M+H]$^+$. $^1$H NMR (400 MHz, DMSO-d$_6$): δ 8.36 (d, J=8.5 Hz, 2H), 8.22 (bs, 1H), 8.05 (bs, 1H), 7.94 (d, J=8.5 Hz, 2H), 7.84 (d, J=8.3 Hz, 1H), 7.68 (bm, 1H), 7.49 (d, J=0.91 Hz, 1H), 7.35 (bm, 1H), 6.30 (dd, J=3.0, 1.9 Hz, 1H), 6.20 (d, J=3.0 Hz, 1H), 4.10 (s, 2H).

Example 77

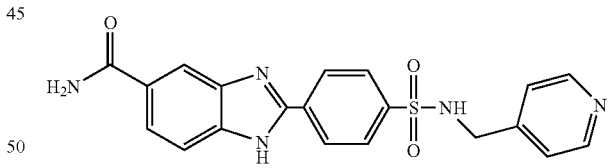

2-{4-[(Pyridin-4-ylmethyl)-sufamoyl]-phenyl}-1H-benzoimidazole-5-carboxylic acid amide A. 4-Formyl-N-pyridin-4-ylmethyl-benzenesulfonamide. This compound was prepared as described in Example 46 substituting (4-aminomethyl)pyridine (106 mg, 0.978 mmol) for benzylamine in Step A. The title compound was obtained as a yellow solid, 219 mg (81%).

B. 2-{4-[(Pyridin-4-ylmethyl)-sulfamoyl]-phenyl}-1H-benzoimidazole-5-carboxylic acid amide. This compound was prepared as described in Example 46 substituting 4-formyl-N-pyridin-4-ylmethyl-benzenesulfonamide (190 mg, 0.688 mmol) for N-benzyl-4-formyl-benzenesulfonamide in Step B. The title compound was obtained as a beige powder, 88 mg (31%). HPLC (Method C): $R_t$=3.57. MS (ESI): mass calculated for $C_{20}H_{17}N_5O_3S$, 407.5; m/z found, 408.1 [M+H]$^+$. $^1$H NMR (400 MHz, DMSO-$d_6$): δ 8.48 (m, 3H), 8.38 (bd, J=6.2 Hz, 2H), 8.32 (bs, 1H), 8.05 (bm, 4H), 7.86 (m, 2H), 7.63 (bm, 1H), 7.35 (bm, 1H), 7.30 (d, J=5.7 Hz, 2H), 4.14 (bd, J=5.6 Hz, 2H).

Example 78

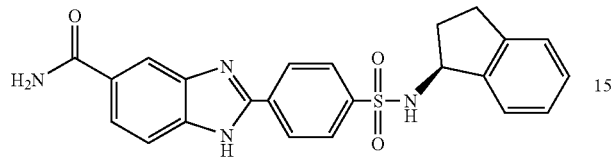

2-[4-((S)-Indan-1-ylsulfamoyl)-phenyl]-1H-benzoimidazole-5-carboxylic acid amide A. 4-Formyl-N-indan-(S)-1-yl-benzenesulfonamide. This compound was prepared as described in Example 46 substituting S-(+)-1-aminoindane (130 mg, 0.978 mmol) for benzylamine in Step A. The title compound Was obtained as a white solid, 242 mg (82%).

B. 2-[4-(S)-Indan-1-ylsulfamoyl)-phenyl]-1H-benzoimidazole-5-carboxylic acid amide. This compound was prepared as described in Example 46 substituting 4-formyl-N-indan-(S)-1-yl-benzenesulfonamide (199 mg, 0.662 mmol) for N-benzyl-4-formyl-benzenesulfonamide in Step B. The title compound was obtained as a beige powder, 74 mg (26%). HPLC (Method C): $R_t$=4.68. MS (ESI): mass calculated for $C_{23}H_{20}N_4O_3S$, 432.5; m/z found, 433.1 [M+H]$^+$. $^1$H NMR (400 MHz, DMSO-$d_6$): δ 8.43 (d, J=8.3 Hz, 2H), 8.23 (bm, 2H), 8.09 (d, J=8.3 Hz, 2H), 8.06 (m, 1H), 7.84 (d, J=8.3 Hz, 1H), 7.69 (m, 1H), 7.35 (bs, 1H), 7.16 (m, 4H), 4.79 (bm, 1H), 2.82 (m, 1H), 2.69 (m, 1H), 2.10 (m, 1H), 1.66 (m, 1H).

Example 79

Determination of Compound Inhibition of Human Cds1 Activity

For the determination of human Cds1 activity in the presence of Cds1 inhibitory compounds, such compounds were incubated in an aqueous mixture at pH 7.4 containing 50 mM HEPES, 100 mM NaCl, 10 mM $MgCl_2$, 5 nM recombinant human Cds1, 10 μM synthetic peptide substrate SGLYRSPSMPENLNRPR having an N-terminal biotin, 1 μM adenosine triphosphate, 50 μCi/mL of [γ-$^{33}$P] adenosine triphosphate, and a protease inhibitor mixture. The reaction mixtures were incubated at 37° C. for 3 h. The peptide substrate was captured from the reaction mixture by incubating the reaction mixture with streptavidin conjugated to agarose beads and 50 mM adenosine triphosphate. The agarose beads were washed repeatedly with a 0.1% solution of Tween®-20 in phosphate-buffered saline, pH 7.4. Enzyme activity at different Cds1 inhibitory compound concentrations was determined by measuring the amount of radioactive phosphate bound to the substrate peptide by scintillation counting. Results are expressed as $IC_{50}$ in Table 1 below.

TABLE 1

| Cds1 Inhibition | |
|---|---|
| Example | $IC_{50}$ (nM) |
| 1 | 55 |
| 2 | 66 |
| 3 | 64 |
| 4 | 43 |
| 5 | 33 |
| 6 | 43 |
| 7 | 7 |
| 8 | 11 |
| 9 | 34 |
| 10 | 7 |
| 11 | 17 |
| 12 | 13 |
| 13 | 36 |
| 14 | 39 |
| 15 | 38 |
| 16 | 240 |
| 17 | 32 |
| 18 | 192 |
| 19 | 29 |
| 20 | 9 |
| 21 | 16 |
| 22 | 33 |
| 23 | 5 |
| 24 | 4 |
| 25 | 71 |
| 26 | 8 |
| 27 | 7 |
| 28 | 13 |
| 29 | 23 |
| 30 | 47 |
| 31 | 9 |
| 32 | 164 |
| 33 | 98 |
| 34 | 42 |
| 35 | 4 |
| 36 | 5 |
| 37 | 5 |
| 38 | 12 |
| 39 | 26 |
| 40 | 171 |
| 41 | 3 |
| 42 | 5 |
| 43 | 264 |
| 44 | 113 |
| 45 | 38 |
| 46 | 56 |
| 47 | 112 |
| 48 | 150 |
| 49 | 66 |
| 50 | 99 |
| 51 | 290 |
| 52 | 182 |
| 53 | 77 |
| 54 | 54 |
| 55 | 49 |
| 56 | 18 |
| 57 | 170 |
| 58 | 40 |
| 59 | 1100 |
| 60 | 42 |
| 61 | 40 |
| 62 | 80 |
| 63 | 14 |
| 64 | 272 |
| 65 | 114 |
| 66 | 41 |
| 67 | 45 |
| 68 | 42 |
| 69 | 42 |
| 70 | 50 |
| 71 | 9 |
| 72 | 18 |
| 73 | 181 |
| 74 | 16 |
| 75 | 19 |

TABLE 1-continued

Cds1 Inhibition

| Example | IC$_{50}$ (nM) |
|---|---|
| 76 | 37 |
| 77 | 134 |
| 78 | 10 |

Example 80

Determination of the Effect of Cds1 Inhibitory Compounds on Radiation-induced Apoptosis in Isolated Primary Cells Spleen cells were isolated from C57/BL6 mice as follows: spleens were disrupted by grinding between two frosted glass slides, and cells were passed through a cell strainer. Erythrocytes were lysed by incubation in ammonium chloride solution followed by careful washing, of cells in isotonic medium. The spleen cells were plated in 60 mm petri dishes at $5 \times 10^6$ cells/mL in RPMI medium containing 10% fetal calf serum and Cds1, inhibitor. One hour after plating of cells with compound, the cells were dosed with 0.5–1 Gy from a $^{137}$Cs γ-radiation source. Determination of apoptotic cells by Annexin V staining was performed using the Annexin V-FITC Apoptosis Detection Kit™ (Cat# PF032 Oncogene Research Products) according to the manufacturer's instructions. Briefly, 6–24 h after irradiation, the cells were washed with buffered isotonic salt solution and suspended at $1 \times 10^6$ cells/mL in binding buffer (10 mM HEPES pH 7.4, 150 mM NaCl, 2.5 mM CaCl$_2$, 1 mM MgCl$_2$, 4% bovine serum albumin) containing 80 ng/mL Annexin V labelled with FITC and 0.4 μg/mL anti-B220 antibody labelled with allophycocyanin. The cells were then pelleted and resuspended in binding buffer containing 0.6 μg/mL propidium iodide. The stained cells were analyzed on a FACS machine (Fluorescence Activated Cell Sorter™, Becton Dickinson). The fraction of viable, non-apoptotic cells was determined by quantifying the number of cells that did not stain with propidium iodide or Annexin V versus the total number of cells. Fractions of non-apoptotic B-cells or total cells were determined separately based on staining with the B220 antibody mentioned above.

Example 81

Determination of Effect of Cds1 Inhibitors on Radiation-induced Caspase Activity in Human CD4$^+$ T-cells Human CD4$^+$ T-cells were isolated from the blood of healthy donors as follows. Whole heparinized blood was layered over Ficoll-Paque (Amersham Pharmacia Biotech, Uppsala, Sweden) and centrifuged 20 min at 560 g. Mononuclear cells were harvested and subjected to positive selection with anti-human CD4-coated MACS MicroBeads (Miltenyi, Auburn, Calif.). Purified CD4$^+$ T-cells were transferred to growth medium (RPMI with 10% fetal calf serum, 50% IU/mL penicillin and 50 μg/mL streptomycin). The cells were dispensed to wells of 96-well tissue culture plates at 200,000 cells/well. Either a Cds1 inhibitory compound in DMSO or the same volume of vehicle was added to each well. The reaction mixtures were incubated at 37° C. for 1 h, exposed to 10 Gy of γ-radiation, and then incubated for 24 h. The CD4$^+$ T-cells were harvested by centrifugation and lysed to release caspase-3. Caspase-3 and caspase-7 specific fluorogenic peptide substrate Acetyl-Asp-Glu-Val-Asp-(7-amino-4-methyl-coumarin) was added to each sample (final concentration=100 μM). Three hours after the addition of peptide, the caspase activity of each sample was determined fluorometrically using a Millipore Cytofluor fluorescent plate reader ($\lambda_{ex}$=360 nm, $\lambda_{em}$=460 nm).

Example 82

Determination of the Effect of Cds1 Inhibitory Compounds on Radiation-induced Apoptosis in Human CD4$^+$ T-cells Human CD4$^+$ T-cells were isolated from the blood of healthy donors and cultured as described in Example 54. The cells were dispensed to wells of 96-well tissue culture plates at 200,000 cells/well. Either a Cds1 inhibitory compound in DMSO or the same volume of vehicle was added to each well. The reaction mixtures were incubated at 37° C. for 1 h, exposed to 10 Gy of γ-radiation, and then incubated for 24 h. Determination of apoptotic cells by Annexin V staining was performed as described in Example 53.

Example 83

Determination of the Effect of Cds1 Inhibitory Compounds on Radiation-induced Apoptosis in Splenocytes in vivo Female C57/BL mice, 6–8 weeks of age, are dosed by oral gavage or by injection with Cds1 inhibitory compound before and at regular intervals after radiation exposure. One to three hours after first compound dose, the animals are irradiated with γ-rays administered to the whole animal at a dose between 0.5 and 4 Gy. At times between 4 and 24 h after irradiation, the animals are sacrificed, and the tissues of interest are excised. Cell apoptosis is quantified using Annexin V staining as described in Example 53. Apoptosis can be studied in a variety of tissues. In some cases other methods for quantification of apoptosis than the method described in Example 53 may be more appropriate. Thus, apoptosis can also be determined by detection of DNA degradation by TUNEL staining, as described by Darzynkiewicz and Bedner (In *Analysis of Apoptotic Cells by Flow and Laser Scanning Cytometry*; Reed, J. C., Ed.; Methods of Enzymology, Vol. 322; Academic Press: San Diego, 2000; 18–39). Briefly, cells or tissues are fixed with formaldehyde and permeabilized with ethanol, and DNA ends are then labelled by attaching nucleotide derivatives such as BrdUTP using the enzyme terminal deoxynucleotidyl transferase. DNA ends can then be detected by incubating the cells or tissues with fluorescently-labelled antibodies reactive with BrdU. Quantification can be done by laser scanning cytometry, by visual microscopical examination or by FACS.

F. OTHER EMBODIMENTS

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A compound of formula (I):

wherein
W is —COOH or —(CO)NH$_2$;
Q is CH;
R$_a$ and R$_b$ are independently selected from —H and halogen;
R$_c$ is absent or is independently selected from the group consisting of —OH, —CF$_3$, —C$_{1-4}$alkyl, —OC$_{1-4}$alkyl, —NO$_2$ and halo;
Z is >C=O
A is phenyl, optionally mono-, di- or tri-substituted with R$_p$;
R$_p$ is selected from the group consisting of —OH, —C$_{1-6}$alkyl, —OC$_{1-6}$alkyl, —C$_{3-6}$cycloalkyl, —OC$_{3-6}$cycloalkyl, —CN, —NO$_2$, —N(R$_y$)R$_z$ (wherein R$_y$ and R$_z$ are independently selected from —H or —C$_{1-6}$alkyl, or may be taken together with the nitrogen of attachment to form an otherwise aliphatic hydrocarbon ring, said ring having 5 to 7 members, optionally having one carbon replaced with >O, =N—, >NH or >N(C$_{1-4}$alkyl) and optionally having one or two unsaturated bonds in the ring), —(C=O)N(R$_y$)R$_z$, —(N—R$_t$)COR$_t$ (wherein R$_t$ is independently —H or —C$_{1-6}$alkyl), —(N—R$_t$)SO$_2$C$_{1-6}$alkyl, —(C=O)C$_{1-6}$alkyl, —(S=(O)$_n$)—C$_{1-6}$alkyl (wherein n is selected from 0, 1 or 2), —SO$_2$N(R$_y$)R$_z$, —SCF$_3$, halo, —CF$_3$, —OCF$_3$, —COOH, —C$_{1-6}$alkylCOOH, —COOC$_{1-6}$alkyl and —C$_{1-6}$alkylCOOC$_{1-6}$alkyl;
and enantiomers, diastereomers and pharmaceutically acceptable salts, esters or amides thereof.

2. The compound of claim 1 wherein W is —(CO)NH$_2$.

3. The compound of claim 1 wherein Q is CH.

4. The compound of claim 1 wherein R$_a$ and R$_b$ are —H, —Cl or —F.

5. The compound of claim 1 wherein R$_a$ is —H and R$_b$ is —Cl or —F.

6. The compound of claim 1 wherein R$_a$ and R$_b$ are —H.

7. The compound of claim 1 wherein R$_c$ is absent or is selected from the group consisting of —OH, —CH$_3$, —CH$_2$CH$_3$, —F, —Cl, —Br, —I, —CF$_3$ and —OCH$_3$.

8. The compound of claim 1 wherein R$_c$ is selected from the group consisting of —F, —Cl, —CH$_3$ and —OCH$_3$.

9. The compound of claim 1 wherein R$_c$ is absent.

10. The compound of claim 1 wherein A, including the R$_p$ substituent, is selected from the group consisting of phenyl, 4-chloro phenyl, 4-methyl-3-chloro phenyl, 4-chloro-3-trifluoromethyl phenyl, 3,4-dichloro phenyl, 3-chloro-4-fluoro phenyl, 2-fluoro-5-trifluoromethyl, phenyl, 4-chloro-3-fluoro phenyl, 3,4-dimethyl phenyl, 4-trifluoromethyl phenyl, 4-bromo phenyl, 4-fluoro-3-methyl phenyl, 3-chloro phenyl, 5-chloro-2-methyl phenyl, 3-trifluoromethyl phenyl, 4-methoxy phenyl, 4-methyl 3,4-dimethyl phenyl, 2-fluoro-3-trifluoromethyl phenyl, 2-chloro-4-methyl phenyl, 4-ethyl phenyl, 4-fluoro phenyl, 3,4-dimethoxy phenyl, 3,4-dimethoxy-5-bromo phenyl, 3-(dimethylamino) phenyl, 4-nitro phenyl, 4-cyano phenyl, 2-methoxy-4-methyl phenyl, 4-trifluoromethoxy phenyl, 2-chloro phenyl, 4-morpholino phenyl, 3-chloro phenyl, 2,3-dichloro phenyl, benzo[1,3]dioxolyl, benzo[1,4]dioxinyl, 4-amino phenyl, 4-hydroxy phenyl, 4-bromo-3-hydroxy phenyl, 4-chloro-2-hydroxy phenyl, 4-chloro-3-hydroxy phenyl, 2,4-dichloro phenyl, 4-bromo-3-methoxy phenyl and 4-iodo phenyl.

11. The compound of claim 1 wherein A, including the R$_p$ substituent, is selected from the group consisting of phenyl, 4-chlorophenyl, 4-methylphenyl, 4-methoxyphenyl, 4-chloro-3-trifluoromethylphenyl, 3-bromo-4,5-dimethoxyphenyl, 3,4-dichlorophenyl, 3,4-dimethylphenyl, 4-ethylphenyl, 2-chlorophenyl, 2,4-dichlorophenyl, 2-methoxyphenyl, 2-methylphenyl and 3-methylphenyl.

12. The compound of claim 1 wherein R$_p$ is selected from the group consisting of —OH, —CH$_3$, —CH$_2$CH$_3$, —OCH$_3$, —OCH$_2$CH$_3$, —OCH(CH$_3$)$_2$, cyclopropyl, cyclobutyl, cyclopentyl, cyclohexyl, —Ocyclopentyl, —Ocyclohexyl, —CN, —NO$_2$, —C(O)NH$_2$, —C(O)N(CH$_3$)$_2$, —C(O)NH(CH$_3$), —NHCOCH$_3$, —NCH$_3$COCH$_3$, —NHSO$_2$CH$_3$, —NCH$_3$SO$_2$CH$_3$, —C(O)CH$_3$, —SOCH$_3$, —SO$_2$CH$_3$, —SO$_2$NH$_2$, —SO$_2$NHCH$_3$, —SO$_2$N(CH$_3$)$_2$, —SCF$_3$, —F, —Cl, —Br, I, —CF$_3$, —OCF$_3$, —COOH, —COOCH$_3$, —COOCH$_2$CH$_3$, —NH$_2$, —NHCH$_3$, —N(CH$_3$)$_2$, —N(CH$_2$CH$_3$)$_2$, —NCH$_3$(CH(CH$_3$)$_2$), imidazolidin-1-yl, 2-imidazolin-1-yl, pyrazolidin-1-yl, piperidin-1-yl, 2- or 3-pyrrolin-1-yl, 2-pyrazolinyl, morpholin-4-yl, thiomorpholin-4-yl, piperazin-1-yl, pyrrolidin-1-yl, homopiperidin-1-yl.

13. The compound of claim 1 wherein R$_p$ is selected from the group consisting of —H, —OH, —OCH$_3$, —OCF$_3$, —CH$_3$, —CH$_2$CH$_3$, —CF$_3$, —F, —Cl, —Br, —I, —NH$_2$, —N(CH$_3$)$_2$, morpholin-4-yl, —NO$_2$, —CN, —C(O)NH$_2$, —COOH, —NHSO$_2$CH$_3$, —SO$_2$NH$_2$.

14. The compound of claim 1 selected from the group consisting of:
2-(4-Benzoyl-phenyl)-1H-benzoimidazole-5-carboxylic acid amide;
2-[4-(4-Chloro-benzoyl)-phenyl]-1H-benzoimidazole-5-carboxylic acid amide;
2-[4-(4-Methyl-benzoyl)-phenyl]-1H-benzoimidazole-5-carboxylic acid amide;
2-[4-(4-Methoxy-benzoyl)-phenyl]-1H-benzoimidazole-5-carboxylic acid amide;
2-[4-(4-Chloro-3-trifluoromethyl-benzoyl)-phenyl]-1H-benzoimidazole-5-carboxylic acid amide;
2-[4-(3-Bromo-4,5-dimethoxy-benzoyl)-phenyl]-1H-benzoimidazole-5-carboxylic acid amide;
2-[4-(3,4-Dichloro-benzoyl)-phenyl]-1H-benzoimidazole-5-carboxylic acid amide;
2-[4-(3,4-Dimethyl-benzoyl)-phenyl]-1H-benzoimidazole-5-carboxylic acid amide;
2-[4-(4-Ethyl-benzoyl)-phenyl]-1H-benzoimidazole-5-carboxylic acid amide;
2-[4-(2-Chloro-benzoyl)-phenyl]-1H-benzoimidazole-5-carboxylic acid amide;
2-[4-(2,4-Dichloro-benzoyl)-phenyl]-1H-benzoimidazole-5-carboxylic acid amide;
2-[4-(2-Methoxy-benzoyl)-phenyl]-1H-benzoimidazole-5-carboxylic acid amide;
2-[4-(2-Methyl-benzoyl)-phenyl]-1H-benzoimidazole-5-carboxylic acid amide.

15. The compound of claim 1 selected from the group consisting of: 2-[4-(4-Methyl-benzoyl)-phenyl]-1H-benzoimidazole-5-carboxylic acid amide; 2-[4-(4-Chloro-3-trifluoromethyl-benzoyl)-phenyl]-1H-benzoimidazole-5-carboxylic acid amide; 2-[4-(3-Bromo-4,5-dimethoxybenzoyl)-phenyl]-1H-benzoimidazole-5-carboxylic acid amide; 2-[4-(3,4-Dichloro-benzoyl)-phenyl]-1H-benzoimidazole-5-carboxylic acid amide; 2-[4-(3,4-Dimethyl-benzoyl)-phenyl]-1H-benzoimidazole-5-carboxylic acid amide; 2-[4-(4-Ethyl-benzoyl)-phenyl]-1H-benzoimidazole-5-carboxylic acid amide.

16. The compound of claim 1:
2-[4-(3,4-Dichloro-benzoyl)-phenyl]-1H-benzoimidazole-5-carboxylic acid amide.

17. A pharmaceutical composition comprising a pharmaceutically acceptable carrier and a Cds-1 inhibiting amount of a compound of the formula:

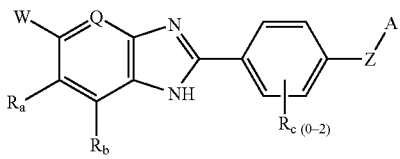

wherein

W is —COOH or —(CO)NH$_2$;

Q is CH;

R$_a$ and R$_b$ are independently selected from —H and halogen;

R$_c$ is absent or is independently selected from the group consisting of —OH, —CF$_3$, —C$_{1-4}$alkyl, —OC$_{1-4}$alkyl, —NO$_2$ and halo;

Z is >C═O

A is phenyl, optionally mono-, di- or tri-substituted with R$_p$;

R$_p$ is selected from the group consisting of —OH, —C$_{1-6}$alkyl, —OC$_{1-6}$alkyl, —C$_{3-6}$cycloalkyl, —OC$_{3-6}$cycloalkyl, —CN, —NO$_2$, —N(R$_y$)R$_z$ (wherein R$_y$ and R$_z$ are independently selected from —H or —C$_{1-6}$alkyl, or may be taken together with the nitrogen of attachment to form an otherwise aliphatic hydrocarbon ring, said ring having 5 to 7 members, optionally having one carbon replaced with >O, ═N—, >NH or >N(C$_{1-4}$alkyl) and optionally having one or two unsaturated bonds in the ring), —(C═O)N(R$_y$)R$_z$, —(N—R$_t$)COR$_t$ (wherein R$_t$ is independently —H or —C$_{1-6}$alkyl), —(N—R$_t$)SO$_2$C$_{1-6}$alkyl, —(C═O)C$_{1-6}$alkyl, —(S═(O)$_n$)—C$_{1-6}$alkyl (wherein n is selected from 0, 1 or 2), —SO$_2$N(R$_y$)R$_z$, —SCF$_3$, halo, —CF$_3$, —OCF$_3$, —COOH, —C$_{1-6}$alkylCOOH, —COOC$_{1-6}$alkyl and —C$_{1-6}$alkylCOOC$_{1-6}$alkyl;

and enantiomers, diastereomers and pharmaceutically acceptable salts, esters or amides thereof.

* * * * *